US012491205B2

(12) United States Patent
Ounzain et al.

(10) Patent No.: US 12,491,205 B2
(45) Date of Patent: Dec. 9, 2025

(54) METHODS AND COMPOSITIONS FOR CONTROLLING CARDIAC FIBROSIS AND REMODELING

(71) Applicant: UNIVERSITÉ DE LAUSANNE, Lausanne (CH)

(72) Inventors: Samir Ounzain, Lausanne (CH); Thierry Pedrazzini, Le Mont-sur-Lausanne (CH)

(73) Assignee: UNIVERSITÉ DE LAUSANNE, Lausanne (CH)

( * ) Notice: Subject to any disclaimer, the term of this patent is extended or adjusted under 35 U.S.C. 154(b) by 304 days.

(21) Appl. No.: 16/623,967

(22) PCT Filed: Jun. 19, 2018

(86) PCT No.: PCT/EP2018/066206
§ 371 (c)(1),
(2) Date: Dec. 18, 2019

(87) PCT Pub. No.: WO2018/234283
PCT Pub. Date: Dec. 27, 2018

(65) Prior Publication Data

US 2020/0197432 A1 Jun. 25, 2020

(30) Foreign Application Priority Data

Jun. 19, 2017 (EP) .................................... 17176725

(51) Int. Cl.

| | |
|---|---|
| ***C12N 15/113*** | (2010.01) |
| ***A61K 31/7088*** | (2006.01) |
| ***C12N 9/22*** | (2006.01) |
| *C12Q 1/68* | (2018.01) |

(52) U.S. Cl.
CPC ............ *A61K 31/7088* (2013.01); *C12N 9/22* (2013.01); *C12N 15/113* (2013.01); *C12N 2310/11* (2013.01); *C12N 2310/113* (2013.01); *C12N 2310/141* (2013.01); *C12N 2310/20* (2017.05)

(58) Field of Classification Search
CPC .... A61K 31/7088; C12N 9/22; C12N 15/113; C12N 2310/11; C12N 2310/141; C12N 2310/20
See application file for complete search history.

(56) References Cited

U.S. PATENT DOCUMENTS

2018/0044672 A1* 2/2018 Zehendner ........... C12Q 1/6883
2019/0048337 A1* 2/2019 Hsu ......................... C12N 9/22

FOREIGN PATENT DOCUMENTS

WO 2015092020 A2 6/2015
WO 2015162161 A1 10/2015
WO WO-2015148860 A1 * 10/2015 ........... C12N 15/113

OTHER PUBLICATIONS

Ounzain, S., et al., "Genome-wide profiling of the cardiac transcriptome after myocardial infarction identifies novel heart-specific long non-coding RNAs," European Heart Journal, 36(6): 353-368 (2014).
Ounzain, Samir and Pedrazzini, Thierry, "The promise of enhancer-associated long noncoding RNAs in cardiac regeneration," Trends in Cardiovascular Medicine, 25(7): 592-602 (2015).
Piccoli, M.T., et al., "Non-coding RNAs as modulators of the cardiac fibroblast phenotype," Journal of Molecular and Cellular Cardiology, 92: 75-81 (2016).
Kumarswamy, R., et al., "Circulating Long Noncoding RNA, LIPCAR, Predicts Survival in Patients With Heart Failure," Circulation Research,114(10): 1569-1575 (2014).
Ounzain, S., et al., "CARMEN, a human enhancer-associated long noncoding RNA controlling cardiac specification, differentiation and homeostasis," Journal of Molecular and Celluar Cardiology, 89: 98-112 (2015).
Micheletti R., "Role of long non-coding RNAs in the stressed heart." Whisper: a novel cardiac fibroblast-enriched lncRNA that Modulate fibrosis in the failing heart, http:/serval.unil.ch/notice/serval:BIB_39C8BACF7BF0 (2016).
Micheletti, R., et al., "The long noncoding RNA Wisper controls cardiac fibrosis and remodeling," Sci Transl Med., 9(395): 1-38 (2017).
International Search Report for PCT Application No. PCT/EP2018/066206 dated Aug. 2, 2018.
International Written Opinion for PCT Application No. PCT/EP2018/066206 dated Aug. 2, 2018.

* cited by examiner

*Primary Examiner* — Sean Mcgarry
(74) *Attorney, Agent, or Firm* — Harness Dickey & Pierce P.L.C.

(57) ABSTRACT

The present invention provides methods and compositions for controlling cardiac fibrosis and heart remodeling in a subject via modulating the expression of one or more lncRNA associated with cardiac-specific super-enhancers (SEs).

5 Claims, 12 Drawing Sheets

Specification includes a Sequence Listing.

Fig.3a
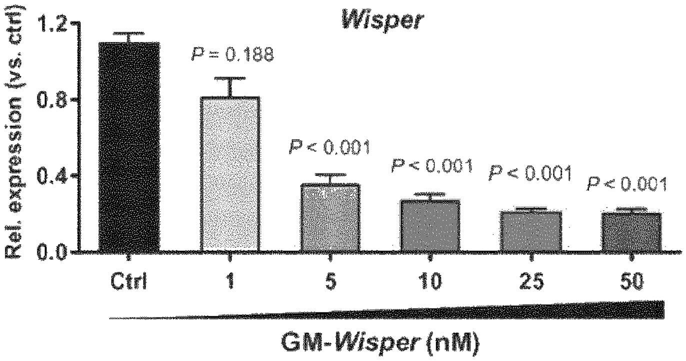
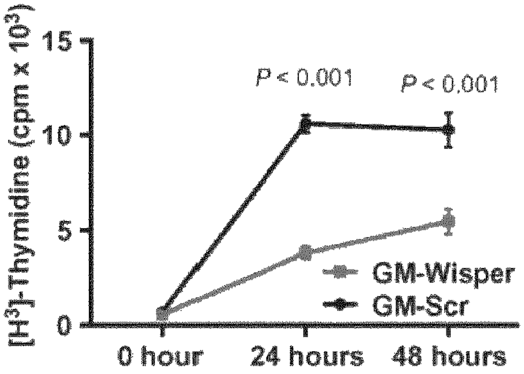
Fig.3c
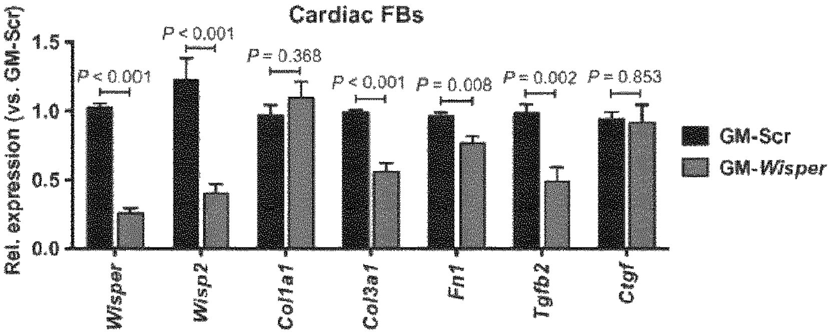
Fig.3b
Fig.3d
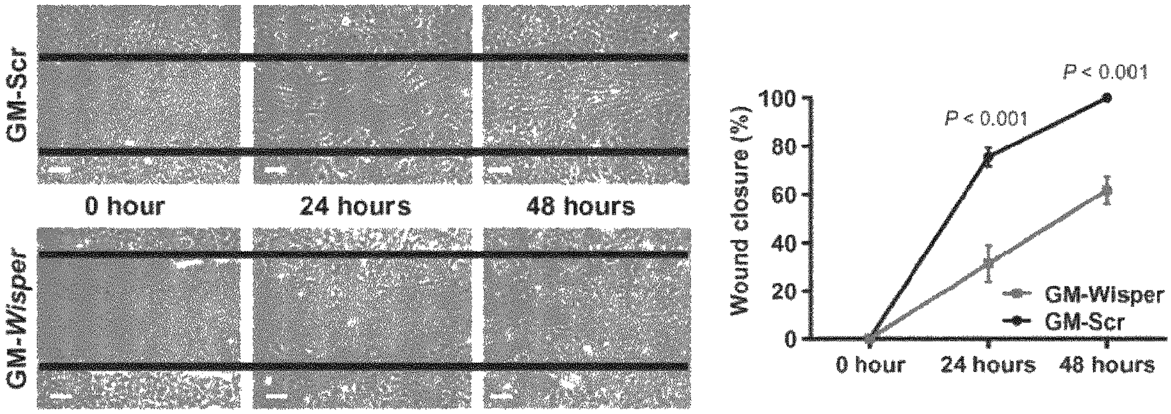

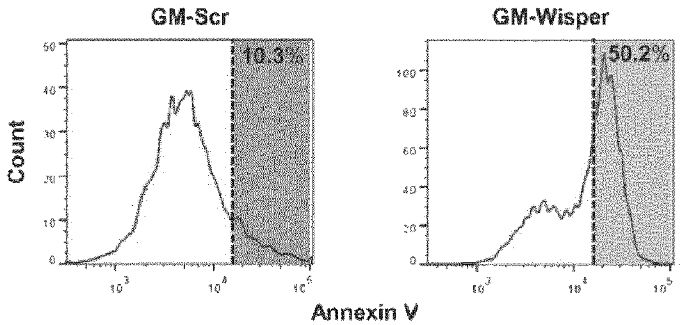
Fig.3e
Fig.3f
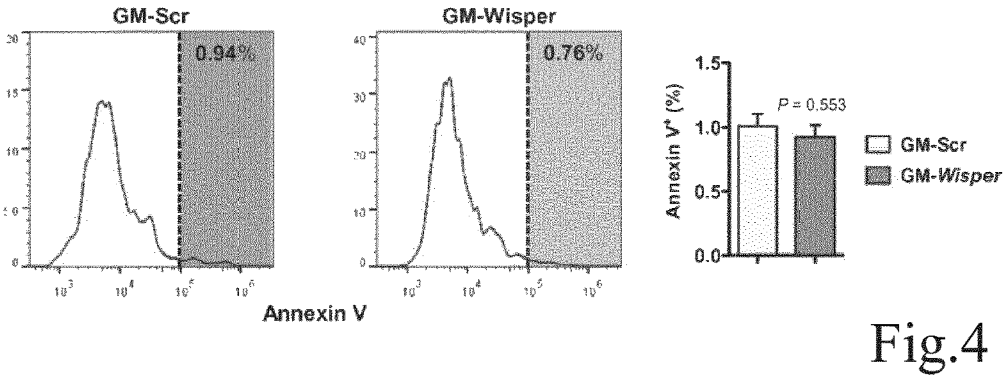
Fig.4
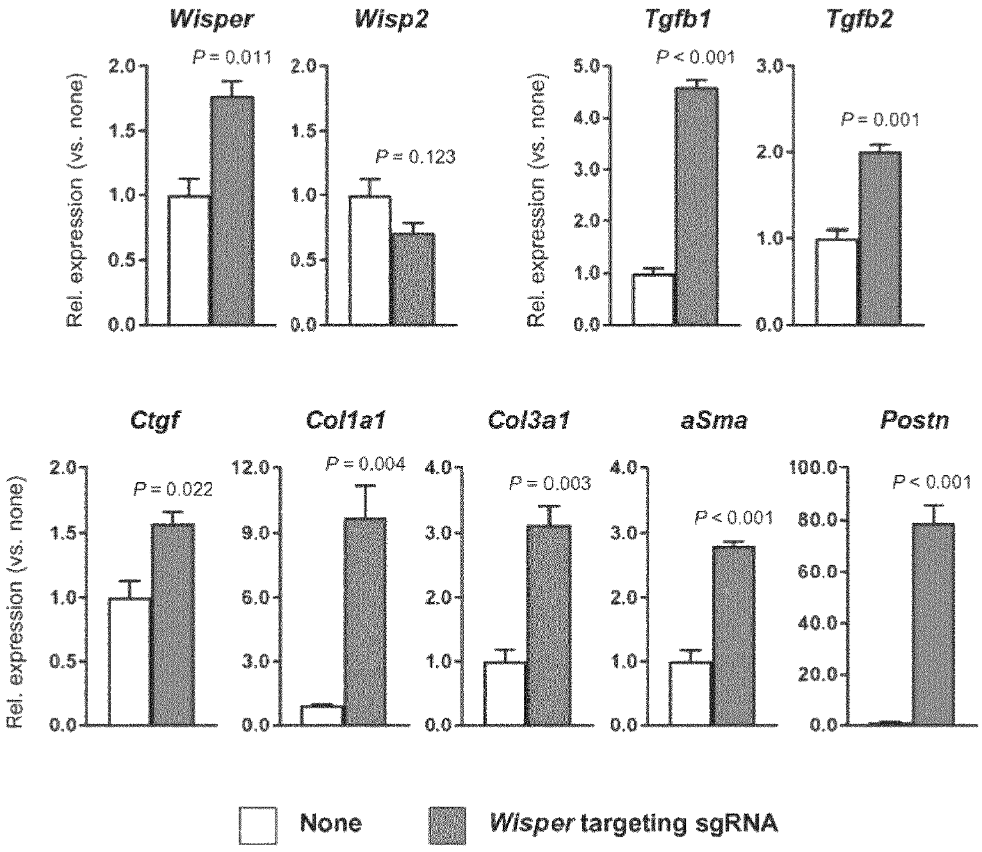

Fig.5a
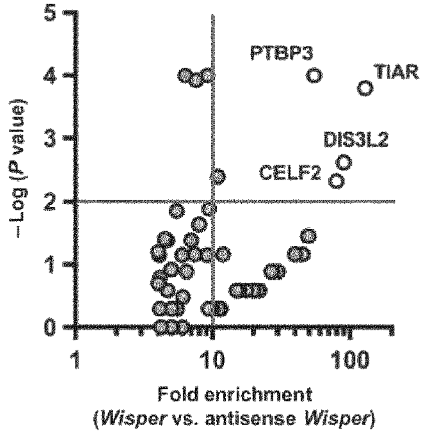
Fig.5b
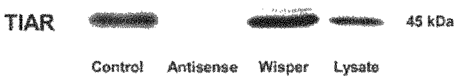
Fig.5c
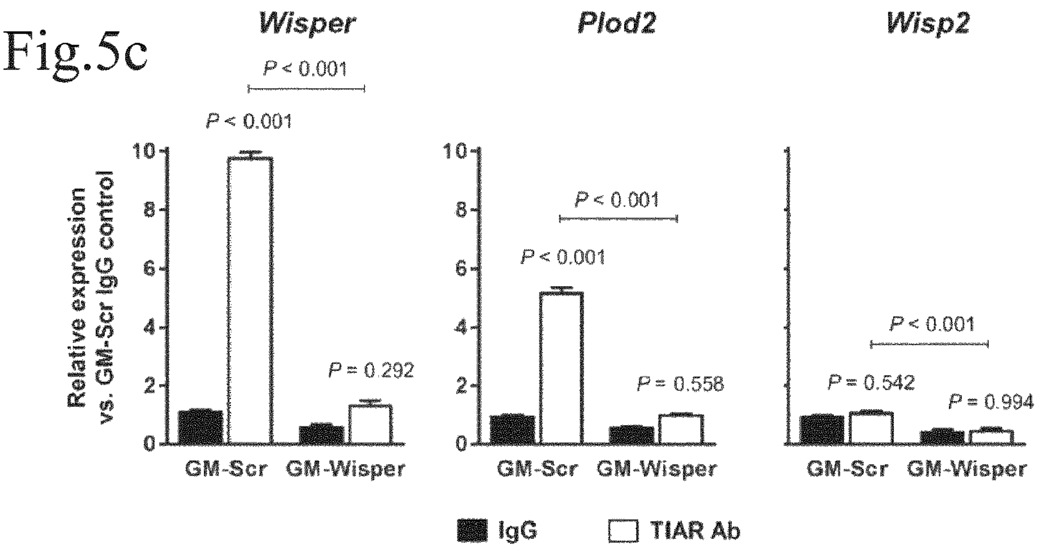
Fig.5d
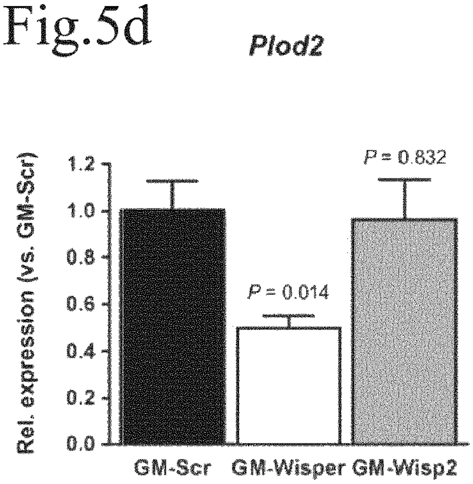
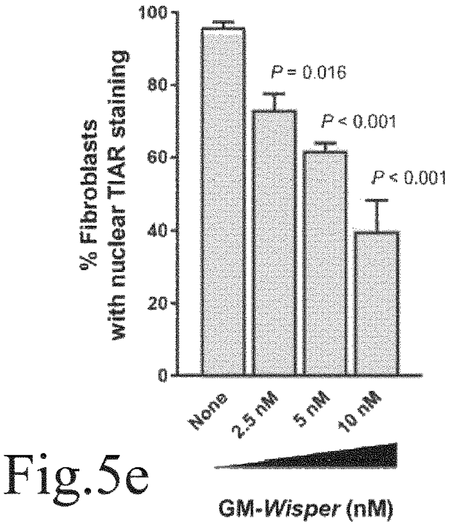
Fig.5e

METHODS AND COMPOSITIONS FOR CONTROLLING CARDIAC FIBROSIS AND REMODELING

CROSS-REFERENCE TO RELATED PATENT APPLICATIONS

This patent application is a U.S. National Phase Application of International Patent Application No. PCT/EP2018/066206 filed on 19 Jun. 2018, which claims priority to European Patent Application No. 17176725.4 filed on 19 Jun. 2017, both of which are hereby incorporated by reference in their entirety.

REFERENCE TO AN ELECTRONIC SEQUENCE LISTING

This application contains references to nucleic acid sequences and/or amino acid sequences which have been submitted as the sequence listing .txt file entitled "SEQUENCE_LISTING_CORRECTION_51377_WO.txt", file size 161,044 Bytes (B), created on 18 Dec. 2019. The aforementioned sequence listing is hereby incorporated by reference in its entirety.

FIELD OF THE INVENTION

The present invention provides methods and compositions for controlling cardiac fibrosis and heart remodeling in a subject via modulating the expression of one or more lncRNA associated with cardiac-specific super-enhancers (SEs).

BACKGROUND OF THE INVENTION

Acute myocardial infarction (MI) due to coronary artery disease typically leads to maladaptive myocardial remodeling and heart failure (HF) (1, 2). HF places a major economic and clinical burden on the industrialized world, accounting for more than 400,000 deaths and more than 20 billion dollars in annual healthcare costs in the US alone (3). Initial translational research has focused on the contracting cells of the heart, the cardiomyocytes (CMs), as a target in therapies aimed at restoring cardiac function. This was despite a wide appreciation that acute and chronic injuries trigger tissue remodeling, which invariably results in and is as a consequence of the development of cardiac fibrosis (1). The destruction of the myocardium after infarction is compensated for by the excessive production of extracellular matrix and the formation of a collagen-rich fibrotic scar. Scar formation, tissue remodeling and progressive interstitial fibrosis lead to a severe loss of function and ultimately HF (1, 2). Moreover, cross-linking enzymes and posttranslational modifications can alter collagen fibrils. This has important implications for matrix synthesis and degradation, which ultimately determine the onset of diastolic dysfunction (4). Despite this clinical importance, very few therapeutic modalities are available to prevent the development of HF. Anti-fibrotic drugs include blockers of the renin-angiotensin-aldosterone system (RAAS) and mineralocorticoid receptor antagonists but are inefficient in the vast majority of fibrotic diseases (5).

Current medications typically slow the progression of the disease rather than prevent or reverse it, which could be achieved if cardiac fibroblasts (CFs) were the primary cell target (6). There is therefore an urgent need to develop alternative therapeutic strategies—for instance, targeting fibroblast differentiation into myofibroblasts or alteration of collagen cross-linking. To achieve this, a deeper characterization of the CF gene program and its associated cellular processes is required to identify specific regulatory molecules and targets (7, 8).

Activation and differentiation of CFs into myofibroblasts initiates the pathological process in the diseased heart. Myofibroblasts synthesize and secrete soluble pro-collagen I and III, which are processed by metalloproteinases, cross-linked by lysyl oxidases and hydroxylases, and assembled into dense fibers. The ability of myofibroblasts to resist apoptosis and secrete large quantities of pro-fibrotic signaling molecules contributes to the overall pathogenesis of HF (1, 6). Like all differentiated cells, CF identity is hardwired by specific gene regulatory networks (GRNs) (7). These GRNs are controlled by core transcription factors (TFs), proteins that interact in a combinatorial manner at cis-regulatory sequences on DNA to regulate downstream programs dictating cell identity and behavior (9, 10). Enhancers, regions of DNA which can be bound by TFs, represent the key information processing units within the genome, and integrate developmental, temporal, spatial and environmental cues (11). In addition, enhancers may assemble together, generating large enhancer clusters named super-enhancers (SEs) (10, 12, 13). These SEs possess important regulatory characteristics, including exquisite cell/tissue-specificity, and appear to be crucial for the maintenance of cell identity. Interestingly, these elements are enriched in single nucleotide polymorphisms (SNPs) linked to common traits and diseases specific to the tissues that harbor them (12).

With the recognition that the mammalian genome is predominantly non protein-coding (15), the classical protein-centric view of GRN regulation appears to have been premature. RNA-sequencing approaches have revealed that the majority of the noncoding genome is actively transcribed, generating thousands of small and long regulatory noncoding RNAs (ncRNAs) (15).

Although the implication of microRNAs in the development of stress- and age-induced cardiac fibrosis is well-documented (16-18), the more abundant and more diverse long ncRNA (lncRNA) group remains to be comprehensively characterized during heart remodeling. Despite increasing implications in CM hypertrophy and function (19-22), the involvement of lncRNAs in regulating cardiac fibrosis needs to be demonstrated (23). LncRNAs are able to regulate GRN activity via a disparate array of transcriptional and post-transcriptional mechanisms (24). Active enhancers are transcribed into non-coding RNAs, and SEs tend to produce more RNAs than typical enhancers (25-27). Enhancer-associated lncRNAs are important for trapping transcription factor proteins on DNA, modifying the local chromatin environment, and organizing nuclear three-dimensional topologies to ensure the correct activation of target gene programs (27, 28).

The Inventors recently characterized the long noncoding transcriptome in a murine model of MI and identified hundreds of novel heart-enriched lncRNAs (29). Interestingly, the vast majority of these transcripts were associated with active heart-specific enhancers (29, 30), especially those dynamically modulated post-MI. Some of these transcripts were conserved in human and shown to be differentially expressed in cardiac disease including aortic stenosis (AOS) and dilated cardiomyopathy (DCM) (29). The Inventors identified Wisper (WIsp2 SuPer-Enhancer associated RNA) as a CF-enriched lncRNA that regulates cardiac fibrosis. Of crucial importance, WISPER is conserved in human, and its expression in the human heart correlates with collagen content and the severity of cardiac fibrosis. Modulating the expression of this lncRNA highlights the potential for CF-specific SE-associated lncRNAs as therapeutic targets for the amelioration of cardiac fibrosis and ultimately HF.

SUMMARY OF THE INVENTION

The present invention provides a method for treating and/or preventing a cardiac disease in a subject in need thereof comprising modulating the expression of one or more lncRNA associated with cardiac-specific super-enhancers (SEs).

Also provided is a gene delivery vector comprising i) an endonuclease, and ii) at least one single guide RNA (sgRNA), or crRNA and tracrRNA, targeting a regulatory sequence of an lncRNA associated with cardiac-specific super-enhancers (SEs) or a genomic DNA sequence encoding an lncRNA associated with cardiac-specific super-enhancers (SEs).

Further provided is a method of treating and/or preventing a cardiac disease in a subject in need thereof, said method comprising i) targeting a regulatory sequence of an lncRNA associated with cardiac-specific super-enhancers (SEs) in a cell ex vivo by contacting said cell with the gene delivery vector of the invention, wherein the at least one single guide RNA (sgRNA), or crRNA and tracrRNA, directs the endonuclease to and hybridizes to said regulatory sequence, thereby modulating the expression of one or more lncRNA associated with cardiac-specific super-enhancers (SEs), and ii) introducing said cell into the subject, thereby treating and/or preventing said cardiac disease.

Further provided is a method of treating and/or preventing a cardiac disease in a subject in need thereof, said method comprising i) targeting a genomic DNA sequence encoding an lncRNA associated with cardiac-specific super-enhancers (SEs) in a cell ex vivo by contacting said cell with the gene delivery vector of the invention, wherein the at least one single guide RNA (sgRNA), or crRNA and tracrRNA, directs the endonuclease to and hybridizes to said genomic DNA sequence, thereby modulating the expression of one or more lncRNA associated with cardiac-specific super-enhancers (SEs), and ii) introducing said cell into the subject, thereby treating and/or preventing said cardiac disease.

Further provided is a composition comprising a gene delivery vector of the invention.

Further provided are pharmaceutical compositions comprising i) a gene delivery vector of the invention, or ii) a cell or population of cells as described herein or iii) a nucleic acid encoding an miRNA, siRNA, piRNA, hnRNA, snRNA, esiRNA, shRNA, or antisense oligonucleotide of the invention, optionally with one or more pharmaceutically acceptable excipient or carrier.

Also provided is a method of treating and/or preventing a cardiac disease comprising administering a pharmaceutical composition of the invention to a subject in need thereof.

Further provided is a single guide RNA (sgRNA), or crRNA and tracrRNA, targeting a regulatory sequence of one or more lncRNA associated with cardiac-specific super-enhancers (SEs) or a genomic DNA sequence encoding an lncRNA associated with cardiac-specific super-enhancers (SEs).

Further provided is a cell or a population of cells comprising one or more nucleic acid(s) encoding i) an sgRNA, or crRNA and tracrRNA, of the invention1, or ii) an nucleic acid encoding an miRNA, siRNA, piRNA, hnRNA, snRNA, esiRNA, shRNA, or antisense oligonucleotide of the invention, or iii) a gene delivery vector of the invention.

Further contemplated in the present invention are nucleic acids encoding

- i) a single guide RNA (sgRNA), or crRNA and tracrRNA, targeting a regulatory sequence of one or more lncRNA associated with cardiac-specific super-enhancers (SEs), or
- ii) a single guide RNA (sgRNA), or crRNA and tracrRNA, targeting a genomic DNA sequence encoding an lncRNA associated with cardiac-specific super-enhancers (SEs), or
- iii) an miRNA, siRNA, piRNA, hnRNA, snRNA, esiRNA, shRNA, or antisense oligonucleotide targeting a regulatory sequence of one or more lncRNA associated with cardiac-specific super-enhancers (SEs), or
- iv) an miRNA, siRNA, piRNA, hnRNA, snRNA, esiRNA, shRNA, or antisense oligonucleotide targeting a genomic DNA sequence encoding an lncRNA associated with cardiac-specific super-enhancers (SEs).

Also provided is a method for controlling cardiac fibrosis and/or heart remodeling in a subject comprising modulating the expression of one or more lncRNA associated with cardiac-specific super-enhancers (SEs).

The invention further contemplates kits for the treatment and/or prevention of a cardiac disease.

DESCRIPTION OF THE FIGURES

FIG. 3. Wisper controls cardiac fibroblast behavior and survival. (A) Wisper expression in adult cardiac fibroblast (CFs) following GapmeR transfection at increasing concentrations. Bars represent means normalized to control±SEM (n≥6). P values determined by Student's t test. (B) Gene expression measured by qRT-PCR in adult CFs (B) following transfection with GapmeRs (10 nM; 48 h; n≥5) targeting Wisper (GM-Wisper) or scrambled GapmeRs (GM-Scr). P values determined by two-way ANOVA (Fisher's test). (C) Proliferation of adult CFs (C) following GapmeR transfection (10 nM) quantified by [$H^3$]-Thymidine incorporation. Data are expressed as mean cpm±SEM (n≥3). P values determined by two-way ANOVA (Bonferroni's test). (D) Migration of adult CFs (D) following GapmeR transfection (10 nM) measured using a wound closure assay. Representative pictures are shown. Scale bar: 100 M. Graphs show the percentage of wound closure at each time point±SEM (n≥3). P values determined by two-way ANOVA (Bonferroni's test). (E) Representative FACS analysis of annexin V-positive adult lung fibroblasts (E) following GapmeR transfection (10 nM). Graphs show the percentage of apoptotic cells±SEM (n=3). P values determined by Student's t test.

FIG. 4. Regulation of cardiac fibroblast gene programs by Wisper. Expression of relevant fibrosis-related genes measured by qRT-PCR in P19CL6 cells following CRISPR-on-mediated Wisper induction (Wisper targeting sgRNA; grey bar) as compared to control (None; white bar). Mean±SEM (n=3). P values determined by Student's t test.

FIG. 5. Wisper is associated with TIA1-related protein and regulates Lysyl hydroxylase 2 expression. (A) Proteins enriched following pulldown using biotinylated Wisper, and identified by mass spectrometry. The x-axis shows the protein enrichment in the Wisper group as compared to the control antisense Wisper group; the y-axis shows the −log P value determined by Fisher's test.) (B) Protein quantification of TIAR by western blotting in the pulled-down protein fraction. Purified TIAR is used as positive control. Graph shows means±SEM (n=3). P values determined by Student's t test. (C) Quantification of RNA following immunoprecipitation using a IgG directed against TIAR or a control IgG. Protein lysate was produced from CFs following transfection with GapmeRs targeting Wisper (GM-Wisper) or scrambled GapmeRs (GM-Scr), (10 nM, 48 h). Graph shows means±SEM (n=6). P values determined by two-way ANOVA (Fisher's test). (D) Plod2 expression in adult CFs following GM-Wisper, GM-Wisp2 or GM-Scr transfection (10 nM, 48 h). Bars represent means±SEM (n=3). P values determined by one-way ANOVA. (E) Percentage of cardiac fibroblasts with nuclear TIAR staining following GM-Wisper treatment at various doses. Bars represent means±SEM (n>6). P values calculated by two-way ANOVA (Fisher's test).

DESCRIPTION OF THE INVENTION

Figure 1:
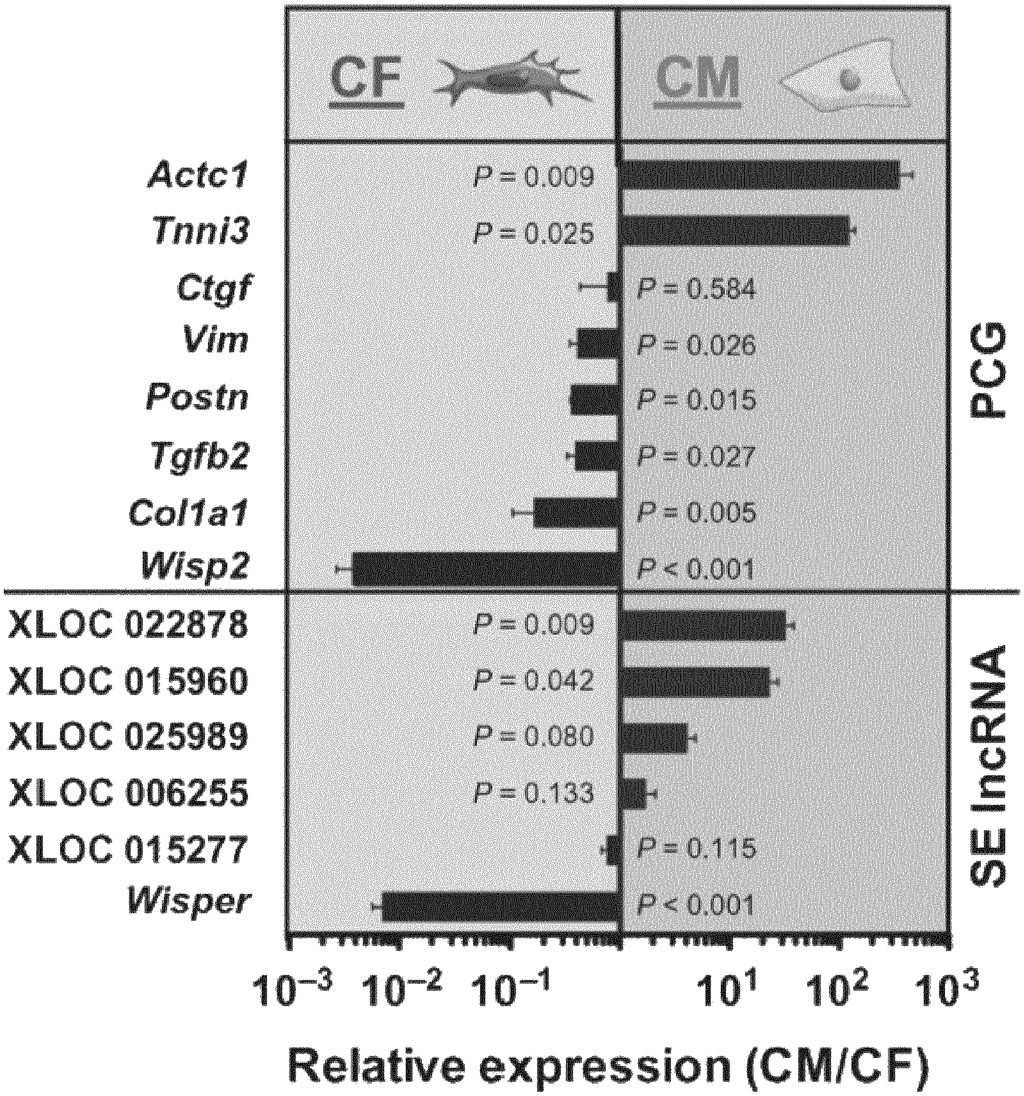
FIG. 1. Identification of super-enhancer-associated lncRNAs. qRT-PCR analysis of super-enhancer-associated lncRNAs (SE-lncRNA) and protein coding gene (PCG) expression in cardiomyocytes and fibroblasts isolated from neonatal mouse hearts. Data represent fold change ratio (CM/CF) mean±SEM (n=3). P value determined by Student's t test.

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application.

Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term “comprise/comprising” is generally used in the sense of include/including, that is to say permitting the presence of one or more features or components.

As used in the specification and claims, the singular form “a”, “an” and “the” include plural references unless the context clearly dictates otherwise.

As used herein, “at least one” means “one or more”, “two or more”, “three or more”, etc.

As used herein the terms “subject”/“subject in need thereof”, or “patient”/“patient in need thereof” are well-recognized in the art, and, are used interchangeably herein to refer to a mammal, including dog, cat, rat, mouse, monkey, cow, horse, goat, sheep, pig, camel, and, most preferably, a human. In some cases, the subject is a subject in need of treatment or a subject with a disease or disorder. However, in other aspects, the subject can be a normal subject. The term does not denote a particular age or sex. Thus, adult and newborn subjects, whether male or female, are intended to be covered. Preferably, the subject is a human, most preferably a human suffering from a cardiac disease (e.g. cardiac fibrosis after MI) or a human that might be at risk of suffering from a cardiac disease (e.g. MI).

The terms “nucleic acid”, “polynucleotide,” and “oligonucleotide” are used interchangeably and refer to any kind of deoxyribonucleotide (e.g. DNA, cDNA, . . . ) or ribonucleotide (e.g. RNA, mRNA, . . . ) polymer or a combination of deoxyribonucleotide and ribonucleotide (e.g. DNA/RNA) polymer, in linear or circular conformation, and in either single—or double—stranded form. These terms are not to be construed as limiting with respect to the length of a polymer and can encompass known analogues of natural nucleotides, as well as nucleotides that are modified in the base, sugar and/or phosphate moieties (e.g. phosphorothioate backbones). In general, an analogue of a particular nucleotide has the same base-pairing specificity; i.e., an analogue of A will base-pair with T.

The term “vector”, as used herein, refers to a viral vector or to a nucleic acid (DNA or RNA) molecule such as a plasmid or other vehicle, which contains one or more heterologous nucleic acid sequence(s) (such as nucleic acid sequence(s) encoding the sgRNA, TRACR and CrRNA, CAS9 nickase, and is designed for transfer between different host cells. The terms “expression vector”, “gene delivery vector” and “gene therapy vector” refer to any vector that is effective to incorporate and express one or more nucleic acid(s), in a cell, preferably under the regulation of a promoter. A cloning or expression vector may comprise additional elements, for example, regulatory and/or post-transcriptional regulatory elements in addition to a promoter.

The term “about,” particularly in reference to a given quantity, is meant to encompass deviations of plus or minus ten (10) percent.

After MI, activated CFs and associated ECM production assume crucial roles during the acute and chronic phases of the adaptive response of the heart to new hemodynamic conditions (1). However, maladaptive changes in ECM dynamics lead to the long term disruption of myocardial architecture and function, eventually leading to heart failure. Excessive ECM deposition and its adverse effects are potentially modifiable (5, 34); indeed, a reduction in the development of fibrosis can be observed in humans treated with therapeutics aimed at limiting pathological remodeling of the diseased heart (5). Due to the non-targeted nature of these approaches, beneficial effects on fibrosis are relatively modest. Nonetheless, these agents improved clinical outcomes providing a strong rationale for the development of highly specific therapeutics directly targeting the CF population.

While focusing on the enhancer landscape and their associated transcripts, the Inventors surprisingly discovered the evolutionary conserved super-enhancer (SE)-associated lncRNAs. One of them, which was named Wisper, is a polyadenylated and multiexonic, CF-enriched transcript. Although the human genome encodes thousands of polyadenylated multiexonic lncRNAs, their functional and translational importance in controlling pathological remodeling and fibrosis remain largely unexplored.

Preferably, the one or more lncRNA associated with cardiac-specific super-enhancers (SEs) of the invention are human CF-enriched transcripts. Most preferably, the one or more lncRNA associated with cardiac-specific super-enhancers (SEs) of the invention are selected from the group comprising Wisper, Sparc, ColW5A1, Cyr61, Smad7 and a combination of one or more thereof. More preferably, the lncRNA associated with cardiac-specific super-enhancers (SEs) is Wisper.

The inventors have shown that Wisper depletion leads to a global transcriptional reprogramming of the networks controlling proliferation, migration, apoptosis and differentiation solely in CFs. Considering its distribution within both the cytoplasm and nucleus, Wisper could exert its action via both cis- and trans-regulatory functions, presumably—but without wishing to be bound by the theory-via interaction with nuclear and cytoplasmic RNA binding proteins. In this context, the Inventors identified TIAR as a Wisper-associated protein. TIAR plays important role in strengthening alternative 5' splice sites (49). PLOD2 has two splice variants with the long form containing an additional exon, whose inclusion is controlled by TIAR. TIAR has been therefore implicated in tissue fibrosis via its capacity to promote production of the long pro-fibrotic PLOD2 form (44). The short form is not expressed in the heart. Moreover, both Wisper and Plod2 bind TIAR, and downregulation of Wisper in CFs decreases TIAR/Piod2 interaction and Plod2 expression, suggesting that Wisper regulates Plod2 mRNA posttranscriptional processing and its cellular concentrations via controlling Plod2 association with TIAR. Interestingly, PLOD2 has also been shown to induce collagen synthesis independently of its action on crosslinking and stabilization of the matrix (50), further supporting a central role for TIAR and PLOD2 in fibrosis. In addition, TIAR is a multifunctional protein that dictates many aspects of RNA metabolism. TIAR functionally interacts with noncoding RNAs, including lncRNAs (51, 52). LncRNA-mediated regulation of TIAR is therefore emerging as a common mechanism to confer context and cell specificity to an otherwise ubiquitously acting system. In particular, TIAR has been implicated in the control of cell proliferation and apoptosis. Remarkably, the GO terms associated with the transcriptional programs following Wisper knockdown are highly reminiscent to the GO terms associated with modulated genes in response to TIAR knockdown (53). In this context, Wisper functions in part by controlling TIAR shuttling into the nucleus (45). Blocking nuclear translocation of TIAR in Wisper-depleted cells is therefore expected to produce global effects on fibroblast gene programs. Three other proteins were identified by mass spectrometry following Wisper pulldown. PTBP3, DIS3L2 and CELF2 demonstrate relevant functions as regulators of differentiation, proliferation and apoptosis (41-43). Their roles in cardiac fibroblasts, and in particular in the development of fibrosis, have not been investigated. These candidates warrant therefore further characterization. It is important to note, however, that many lncRNAs are associated with RNA processing factors involved in maturation of the primary transcripts via post-transcriptional modification. Association of these proteins with a multiexonic lncRNA such as Wisper might also reflect the need for this transcript to be appropriately processed for ensuring its functions. In this regard, TIAR, while being a splicing factor, is the only protein of this small group with a demonstrated link to fibrosis.

The extent of gene reprogramming in fibroblast following Wisper knockdown demonstrate that Wisper exerts several important functions, some of them being probably independent of TIAR. The Inventors examined therefore expression of genes topologically associated within the Wisper locus. Among those, Wisp2 is co-modulated with Wisper during fibroblast differentiation and after Wisper knockdown, suggesting that Wisper could directly control its proximal coding gene in cis. However, several pieces of evidence indicate that concomitant expression of Wisper and Wisp2 does not necessarily reflect cis-regulation. Although Wisper knockdown in mouse CFs in vitro induces Wisp2 downregulation, this effect is not observed in human CFs. In addition, the expression signature after Wisp2 loss of function in CFs is distinct from that observed after Wisper knockdown, suggesting that Wisper effects are not mediated via Wisp2. Moreover, CRISPR-on-mediated induction of Wisper expression at its site of transcription does not activate Wisp2 expression. Finally, Wisp2 is highly expressed in the lungs where modest Wisper expression is observed. The reason for Wisp2 being highly expressed in this organ is possibly related to the presence in its promoter of binding sites for transcription factors that are known to induce lung-specific gene programs. In the heart, Wisp2 has recently been implicated in the therapeutic regression of cardiac fibrosis (31). Wisp2 appears to act therefore more as a compensatory molecule that limits the extent of fibrosis rather than a promoter of fibrosis. We believe therefore that Wisp2 downregulation in the heart occurs secondary to Wisper depletion as a direct consequence of the induced beneficial impact on cardiac fibrosis.

Unlike most tissues in which myofibroblasts undergo apoptosis or revert back to a quiescent state in the absence of pathological stress, this does not occur in the heart. However, GapmeR-mediated depletion of Wisper prior to MI attenuates pathological fibrosis and remodeling. Nevertheless, preventive Wisper depletion also negatively impacts the acute wound healing process, resulting in cardiac rupture and increased mortality. Loss of CFs in the stressed heart affects the matrix that is key for the homeostatic maintenance of myocardial integrity (6). CFs produce the collagenous matrix that prevents myofiber slippage and sustains ventricular chamber geometry under normal conditions; interfering with this process results in weakening of the ventricular wall and susceptibility to rupture. Along the same lines, it is likely that massive doses of anti-Wisper GapmeRs destabilize the delicate architecture of the normal heart, leading to cardiac dysfunction.

The detrimental effects of the Wisper GapmeR treatment during the acute phase could be overcome when using a therapeutic protocol in which GapmeRs were administered 2 days post-infarction. Wisper knockdown during this clinically relevant window of time did not negatively affect acute wound healing while still blunting pathological fibrosis, reducing remodeling and improving cardiac function at 7 and 28 days post-infarction. These data coupled with the observation that human WISPER expression is correlated with fibrosis in AOS patients support translation into clinical scenarios. Clearance of activated CFs from the diseased heart appears to be a highly efficient process leading to progressive reduction of pathological fibrosis and diminished incidence of HF (5, 6). One could also envisage Wisper being targeted in the context of unchecked reactive fibrosis in the myocardium independently of the underlying disease etiology. This could be of high clinical relevance as myocardial fibrosis persists in patients with HF even when treated according to current guidelines, and correlates with mortality. An important finding in the present study is the apparent cardiac specificity of Wisper expression. Under basal conditions, Wisper is clearly a cardiac fibroblast-enriched transcript. Cardiac TF binding sites in the SE element provides an explanation for this interesting feature. Finally, our data also demonstrate that lncRNA associated with cardiac-specific super-enhancers (SEs) like Wisper are potentially highly sensitive markers for pathological fibrosis. Considering the ability to detect lncRNAs circulating in human plasma (55), measurement of circulating WISPER concentrations might provide a noninvasive means to monitor cardiac remodeling. Interestingly, we have previously analyzed a series of novel lncRNAs including Wisper, and correlated their expression with echocardiographic traits after infarction, supporting the notion that these transcripts may represent interesting marker candidates (29, 66). Altogether, the identification of this CF-specific regulatory molecule represents therefore an important step toward the development of targeted anti-fibrotic therapeutic approaches and diagnostic tools.

The present invention thus concerns a method for treating and/or preventing a cardiac disease in a subject in need thereof, said method comprising modulating the expression of one or more lncRNA associated with cardiac-specific super-enhancers (SEs).

The term "treatment" or "treating" means any administration of a composition, pharmaceutical composition, therapeutic agent, compound, etc., of the disclosure to a subject for the purpose of:

(i) inhibiting the disease, that is, arresting the development of clinical symptoms; and/or (ii) relieving the disease, that is, causing the regression of clinical symptoms.

As used herein, the term "prevention" or "preventing" means any administration of a composition, pharmaceutical composition, therapeutic agent, compound, etc., of the disclosure to a subject for the purpose of:

(i) preventing the disease, that is, causing the clinical symptoms of the disease not to develop; In the context of the present invention, the disease is a cardiac disease, preferably a cardiac fibrosis.

The expression of the one or more lncRNA associated with cardiac-specific super-enhancers (SEs) can be either upregulated or downregulated. Preferably, the expression of the one or more lncRNA associated with cardiac-specific super-enhancers (SEs) is modulated by repressing or activating the transcription of said lncRNAs.

Any suitable method for modulating the expression of one or more lncRNA associated with cardiac-specific super-enhancers (SEs) may be used that results in either upregulation or downregulation of said expression. Examples of methods include RNAi mediated knock-down using antisense oligonucleotides (ASOs) and gene editing systems.

Any nuclease of the gene editing system known in the art, such as a meganuclease, zinc finger nuclease (ZFNs), transcription activator-like effector-based nuclease (TALEN), CPF1 is also intended to be within the scope of the present invention.

ASOs may be directed against any cis-regulatory or trans-regulatory sequences, or fragments thereof, or variants thereof, of the one or more lncRNA of the invention. Alternatively, ASOs may also be directed against a genomic sequence encoding an lncRNA of the invention.

Examples of ASOs include, e.g., miRNA, siRNA, piRNA, snRNA or a modified ASO such as GapmeRs.

The terms “microRNA,” “miRNA,” and MiR” are interchangeable and refer to endogenous or artificial non-coding RNAs that are capable of regulating gene expression. It is believed that miRNAs function via RNA interference. The terms “siRNA” and “short interfering RNA” are interchangeable and refer to single-stranded or double-stranded RNA molecules that are capable of inducing RNA interference. SiRNA molecules typically have a duplex region that is between 18 and 30 base pairs in length.

The terms “piRNA” and “Piwi-interacting RNA” are interchangeable and refer to a class of small RNAs involved in gene silencing. PiRNA molecules typically are between 26 and 31 nucleotides in length.

The terms “snRNA” and “small nuclear RNA” are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against one or more lncRNAs.

Examples of modified ASOs include the GapmeRs. As used herein, a GapmeR is a chimeric antisense oligonucleotide that contains a central block of deoxynucleotide monomers sufficiently long to induce RNase H cleavage. Usually, the GapmeRs of the invention are directed against one or more lncRNA sequences. Preferably, the GapmeR is selected from the group comprising SEQ ID No. 12, SEQ ID No. 14 or a combination thereof.

Preferably, the expression of one or more lncRNA is upregulated or downregulated by using a gene editing system such as, e.g. the CRISPR-based gain/loss-of-function system. Usually, the CRISPR-based gain/loss-of-function system comprises at least one single guide RNA (sgRNA), or crRNA and tracrRNA, and a structure-guided endonuclease such as an RNA-guided endonuclease.

Any suitable naturally occurring, or engineered, RNA-guided endonuclease can be employed as long as it is effective for binding a target DNA and it may be selected from the non-limiting group comprising Cas9, Cpf1, and FEN-1. Preferably, the RNA-guided endonuclease is Cas9.

The CRISPR/Cas9 system has become a remarkably flexible tool for genome manipulation over the years. A unique feature of Cas9 endonuclease is its ability to bind target DNA independently of its ability to cleave target DNA.

Within the context of this disclosure, the Cas9 endonuclease is preferably a modified Cas9 endonuclease such as, e.g. an enzymatically dead Cas9. Specifically, both RuvC- and HNH-nuclease domains can be rendered inactive by point mutations (e.g. D10A and H840A in SpCas9), resulting in a nuclease dead Cas9 molecule that cannot cleave target DNA. However, the dead Cas9 molecule retains the ability to bind to target DNA based on the sgRNA targeting sequence, which sgRNA sequence is comprised in CRISPR-based gain/loss-of-function system.

In one aspect, the enzymatically dead Cas9 is tagged with one or more transcriptional repressor or one or more transcriptional activator (see (68) which is incorporated herein by reference).

In another aspect, the enzymatically dead Cas9 is tagged with one or more epitope that is/are recognized by one or more antibody-activator/repressor effector. This enzymatically tagged dead Cas9 can then target the regulatory sequence resulting in robust transcription repression or activation of downstream target gene encoding the lncRNA of the invention.

Usually and within the context of the invention, the regulatory sequence is a promoter or enhancer region which is either a cis- or a trans-acting regulatory sequence. Preferably, said regulatory sequence is selected from the non-limiting group comprising the proximal Wisper enhancer (SEQ ID No. 1), the proximal Wisper promoter (SEQ ID No. 2), the Wisper super-enhancer (SEQ ID No. 3), the Wisper downstream cis sequence (SEQ ID No. 4), the Smad7 cis-regulatory sequence (SEQ ID No. 5), the Cyr61 cis-regulatory sequence (SEQ ID No. 6), the Col15A1 cis-regulatory sequence (SEQ ID No. 7), the Sparc cis-regulatory sequence (SEQ ID No. 8), or fragments thereof, or variants thereof, and a combination of one or more thereof. Most preferably, the regulatory sequence is selected from the non-limiting group comprising the proximal Wisper enhancer (SEQ ID No. 1), the proximal Wisper promoter (SEQ ID No. 2), the Wisper super-enhancer (SEQ ID No. 3), the Wisper downstream cis sequence (SEQ ID No. 4), or fragments thereof, or variants thereof, and a combination of one or more thereof.

The at least one single guide RNA (sgRNA), or crRNA and tracrRNA, usually recognizes a target sequence comprising 16 to 25 nucleotides.

As described below, the target sequence is a DNA regulatory sequence of an lncRNA associated with cardiac-specific super-enhancers (SEs). Alternatively, the target sequence is a DNA, e.g. genomicDNA, encoding for an incRNA associated with cardiac-specific super-enhancers (SEs). Preferably, the lncRNA associated with cardiac-specific super-enhancers (SEs) is Wisper.

Any suitable engineered sgRNA, or crRNA and tracrRNA, can be employed as long as it is effective for recognizing a target DNA of the invention. The design of such sgRNA, or crRNA and tracrRNA is within the skill of ordinary artisans. The sgRNA can, e.g. be the sgRNA MS2 described herein as set forth in SEQ ID No. 13.

Usually, the method for treating and/or preventing a cardiac disease in a subject in need thereof comprises the step of administering a gene delivery vector or an acid nucleic as described herein.

“Administering”, as it applies in the present invention, refers to contact of an effective amount of a gene delivery vector or an acid nucleic of the invention, to the subject.

Administering a nucleic acid of the invention, such as ASOs (e.g. miRNA, siRNA, piRNA, snRNA) or modified ASOs (GapmeRs) to a cell comprises transducing, transfecting, electroporating, translocating, fusing, phagocytosing, shooting or ballistic methods, etc., i.e., any means by which a nucleic acid can be transported across a cell membrane.

Another aspect of the invention concerns a gene delivery vector comprising i) an endonuclease of the invention, and ii) at least one single guide RNA (sgRNA), or crRNA and tracrRNA, recognizing a target sequence comprising 16 to 25 nucleotides.

Any suitable vector can be employed that is effective for introduction of one or more nucleic acid(s) into cells. Preferably, the gene delivery vector of the invention is a viral vector, such as a *lenti*- or baculo- or preferably adeno-viral/adeno-associated viral (AAV) vectors, but other means of delivery or vehicles are known (such as yeast systems, microvesicles, gene guns/means of attaching vectors to gold nanoparticles) and are provided, in some aspects, one or more of the viral or plasmid vectors may be delivered via liposomes, nanoparticles, exosomes, microvesicles, or a gene-gun. Most preferably, the gene delivery vector is selected from the group comprising an adeno-associated virus (AAV) and a lentivirus. Lentivirus of 1st, 2nd, and 3rd generation are also envisioned and are known in the art.

The type of AAV surface protein determines the target tissue. Preferably, any adeno-associated virus (AAV) serotype or engineered AAV is envisioned. Most preferably, the AAV will be selected from the group comprising AAV6 and AAV9, due to their broad tissue specificity and expression levels. AAV9 particularly has a minimal inflammatory response, thereby reducing the side effects. The viral particles will usually be administered by injection into the bloodstream. AAV6 can also be used with cultured patient-derived cells. This will be useful, e.g. when using the approach in iPSCs or ES cells as described in the present disclosure.

Preferably, the endonuclease is a Cas9 endonuclease, most preferably a modified Cas9 endonuclease such as, e.g. an enzymatically dead Cas9.

In one aspect, the enzymatically dead Cas9 is optionally tagged with one or more transcriptional repressor or one or more transcriptional activator depending on whether the expression, i.e. the transcription, of the one or more lncRNA of the invention is to be repressed or activated. Transcription repression by dCas9 can be improved by fusing dCas9 with different repressor domains including, e.g. MAX-interacting protein 1 (MXIl), Kruppel-associated box (KRAB) domain or four concatenated mSin3 domains (SID4X), to either amino or carboxyl termini. On the other hand, transcription activation can be improved by fusing dCas9 with different activator domains including, e.g., multiple repeats of the herpes simplex VP16 activation domain (VP64 or VP160) or the nuclear factor-xB (NF-κB) transactivating subunit activation domain (p65AD) (see (67) Dominguez et al., 2016 which is incorporated herein by reference).

In another aspect, the enzymatically dead Cas9 is optionally tagged with one or more epitope that is/are recognized by one or more antibody-activator/repressor effector. This enzymatically tagged dead Cas9 can then target the regulatory sequence resulting in robust transcription repression or activation of downstream target gene encoding the lncRNA of the invention.

Usually, said "target sequence" is a regulatory sequence of an lncRNA associated with cardiac-specific super-enhancers (SEs). Typically, this target sequence will be selected from the lncRNA regulatory sequences listed in Table 1.

A further aspect of the invention relates to a method of treating and/or preventing a cardiac disease in a subject in need thereof, said method comprising (a) targeting a regulatory sequence of an lncRNA associated with cardiac-specific super-enhancers (SEs) in a cell ex vivo by contacting said cell with a gene delivery vector of the invention, wherein the at least one single guide RNA (sgRNA), or crRNA and tracrRNA, directs a structure-guided endonuclease of the invention, such as a Cas9 endonuclease, and (b) introducing said cell into the subject, thereby treating and/or preventing said cardiac disease.

Preferably, the Cas9 is a modified Cas9 endonuclease such as, e.g. an enzymatically dead Cas9. Most preferably, said Cas9 (e.g. an enzymatically dead Cas9) is modified for transcriptional activation and/or repression and hybridizes to regulatory sequence, thereby modulating the expression of one or more lncRNA associated with cardiac-specific super-enhancers (SEs), Preferably, the cardiac disease is cardiac fibrosis.

The invention further relates to pharmaceutical compositions.

In one aspect, the pharmaceutical composition comprises a gene delivery vector of the invention, preferably in an effective amount. The pharmaceutical composition may further comprise one or more pharmaceutically acceptable excipient or carrier.

In another aspect, the pharmaceutical composition comprises a nucleic acid (e.g. an ASO or a modified ASO such as a GapmeR) of the invention, preferably in an effective amount. The pharmaceutical composition may further comprise one or more pharmaceutically acceptable excipient or carrier.

An "effective amount", when it refers to an active principle of a pharmaceutical composition of the invention, is an amount sufficient to effect beneficial or desired results, such as an amount that inhibits the activity of an lncRNA, for example by interfering with transcription. An effective amount can be administered in one or more administrations, applications, or dosages.

In a further aspect, the pharmaceutical composition comprises a nucleic acid (e.g. an ASO or a modified ASO) targeting an lncRNA associated with cardiac-specific super-enhancers (SEs). Most preferably, said one or more antisense oligonucleotide targets Wisper and is a modified antisense oligonucleotide (GapmeR) having a sequence as set forth in SEQ ID No 12 or 14 or a combination thereof.

A "Pharmaceutically acceptable excipient or carrier" refers to an excipient that may optionally be included in the compositions of the invention and that causes no significant adverse toxicological effects to the patient. It usually refers to a diluent, adjuvant, or vehicle with which the active principle is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. A thorough discussion of pharmaceutically acceptable excipients is available in REMINGTON'S PHARMACEUTICAL SCIENCES (Mack Pub. Co., N.J. 1991) which is incorporated by reference herein.

"Pharmaceutically acceptable salt", e.g. of a nucleic acid of the invention, includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

Another aspect of the invention concerns a method of treating and/or preventing a cardiac disease comprising administering a pharmaceutical composition of the invention to a subject in need thereof. Preferably, a pharmaceutical composition of the invention is administered in a therapeutically effective dose or amount. A pharmaceutical composition of the invention can be administered alone or in combination with one or more additional therapeutic agents.

By "therapeutically effective dose or amount" is intended an amount of a therapeutic agent that, when administered as described herein, brings about a positive therapeutic response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein. Preferably, the cardiac disease is cardiac fibrosis.

The actual dose to be administered will vary depending upon the therapeutic agent (gene delivery vector or nucleic acid), age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Generally, a therapeutically effective amount of a nucleic acid of the invention, will range from about 0.50 mg to 5 grams daily, more preferably from about 5 mg to 2 grams daily, even more preferably from about 7 mg to 1.5 grams daily.

In certain aspects, multiple therapeutically effective doses of each of at least one nucleic acid and at least one additional therapeutical agent will be administered according to a daily dosing regimen, or intermittently. For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. By "twice-weekly" or "two times per week" is intended that two therapeutically effective doses of the agent in question is administered to the subject within a 7 day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7 day period, allowing for a minimum of 48 hours between doses and a maximum of 72 hours between doses. For purposes of the present invention, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved. The agents can be administered by any acceptable route of administration as noted herein below.

In case the pharmaceutical composition of the invention comprises a GapmeR targeting an lncRNA associated with cardiac-specific super-enhancers (SEs), then it will preferably be administered 1-5 days post-infarction, preferably 2-4 days post-infarction, most preferably 2 days post-infarction.

When the pharmaceutical composition comprising a GapmeR of the invention is to be administered for preventing a cardiac disease, then said pharmaceutical composition of the invention will preferably be administered before the risk of myocardial infarction.

More preferably, said one or more antisense oligonucleotide targets Wisper and is a modified antisense oligonucleotide (GapmeR) having a sequence as set forth in SEQ ID No 12 or 14.

A therapeutic agent of the invention can be administered prior to, concurrent with, or subsequent to at least one additional therapeutic agent. If provided at the same time as the additional therapeutic agent, the active agent can be provided in the same or in a different composition. Thus, the agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising an active agent and at least one therapeutically effective dose of a pharmaceutical composition comprising at least one additional therapeutic agent according to a particular dosing regimen. Administration of the separate pharmaceutical compositions can be at the same time (i.e., simultaneously) or at different times (i.e., sequentially, in either order, on the same day, or on different days), so long as the therapeutic effect of the combination of these substances is caused in the subject undergoing therapy.

In other aspects of the invention, the pharmaceutical composition of the invention is a sustained-release formulation, or a formulation that is administered using a sustained-release device. Such devices are well known in the art, and include, for example, transdermal patches, and miniature implantable pumps that can provide for drug delivery over time in a continuous, steady-state fashion at a variety of doses to achieve a sustained-release effect with a non-sustained-release pharmaceutical composition. The pharmaceutical compositions of the invention may be administered using the same or different routes of administration in accordance with any medically acceptable method known in the art. Suitable routes of administration include parenteral administration, such as subcutaneous (SC), intraperitoneal (IP), intramuscular (IM), intravenous (IV), or infusion, oral and pulmonary, nasal, topical, transdermal, and suppositories. Where the composition is administered via pulmonary delivery, the therapeutically effective dose is adjusted such that the soluble level of the agent is equivalent to that obtained with a therapeutically effective dose that is administered parenterally, for example SC, IP, IM, or IV. In some embodiments of the invention, the pharmaceutical composition is administered by IM or SC injection, particularly by IM or SC injection locally to the region where the therapeutic agent or agents used in the cardiac therapy protocol are administered.

Factors influencing the respective amount of the various compositions to be administered include, but are not limited to, the mode of administration, the frequency of administration (i.e., daily, or intermittent administration, such as twice- or thrice-weekly), the particular disease undergoing therapy, the severity of the disease, the history of the disease, whether the individual is undergoing concurrent therapy with another therapeutic agent, and the age, height, weight, health, and physical condition of the individual undergoing therapy. Generally, a higher dosage of this therapeutic agent is preferred with increasing weight of the subject undergoing therapy. Agent can be administered between one day and months post stress/injury. Furthermore administration can be executed in patients suffering with established interstitial fibrosis as present in end-stage heart failure.

Alternatively, the one or more nucleic acid(s) encoding e.g. the sgRNA and/or the endonuclease, the ASOs or modified ASOs, can also be delivered in the form of RNA.

To enhance expression and reduce possible toxicity, the one or more nucleic acid(s) in the form of RNA, can be modified to include one or more modified nucleoside e.g. using pseudo-U or 5-Methyl-C. Optionally, said one or more nucleic acid(s) can be under the regulation of regulatory elements in addition to a promoter.

Any suitable promoter or enhancer may be used that results in expression of one or more nucleic acid(s) into cells. Preferably, the expression of the sgRNA will be driven by a promoter preferably positioned upstream, e.g. contiguous to and upstream, such H1 or a U6 promoter, of the sequence encoding said sgRNA. Other tissue-specific promoters can be envisioned, particularly when cardiac tissue or cardiac cells are targeted.

In one aspect, the promoter is an inducible promoter that can be turned on or off at certain stages of development of an organism or in a particular tissue. Preferably, the inducible promoter will be selected from the group comprising promoters whose activity is modified in response to heavy-metal ions, isopropyl-ß-D-thiogalactoside, hormones, progesterone antagonists or antibiotics. Most preferably, the inducible promoter will be selected from the group comprising Tetracycline or doxycycline (dox)-inducible promoter.

Preferable mammalian cultured cell lines, embryonic stem (ES) cells, induced pluripotent stem cells (iPSCs) will be selected—or will be derived from—heart cells such as, e.g. cardiac fibroblasts, myocytes, endothelial cells, and vascular smooth muscle cells.

The present invention further concerns a pharmaceutical composition as described herein for use in the treatment and/or prevention of a cardiac disease. Preferably, the cardiac disease is cardiac fibrosis.

The present invention further contemplates the use of a pharmaceutical composition as described herein in the preparation of a medicament for the treatment and/or prevention of a cardiac disease of the invention.

The invention also contemplates kits for the treatment and/or prevention of a cardiac disease. In one aspect of the invention, the kit comprises i) a first gene delivery vector comprising an endonuclease of the invention, and ii) a second gene delivery vector comprising at least one single guide RNA (sgRNA), or crRNA and tracrRNA, recognizing a target sequence comprising 16 to 25 nucleotides. Alternatively, the endonuclease of the invention and the at least one single guide RNA (sgRNA), or crRNA and tracrRNA, recognizing a target sequence comprising 16 to 25 nucleotides of the invention are comprised in one single gene delivery vector.

In another aspect, the invention further contemplates a kit for the treatment and/or prevention of a cardiac disease comprising a pharmaceutical composition comprises a nucleic acid (e.g. an ASO or a modified ASO) targeting an lncRNA associated with cardiac-specific super-enhancers (SEs).

In a further aspect, the invention contemplates is a kit for the treatment and/or prevention of a cardiac disease comprising a cell of the invention.

The kits of the invention may also comprise a container and a label or package insert on or associated with the container. Suitable containers include, for example, bottles, vials, syringes, etc. The containers may be formed from a variety of materials such as glass or plastic. The container holds a composition which is effective for treating the disease of disorder of the invention and may have a sterile access port (for example the container may be an intravenous solution bag or a vial having a stopper pierceable by a hypodermic injection needle). Alternatively, or additionally, the kits may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The label or package insert may comprise instructions for use thereof. Instructions included may be affixed to packaging material or may be included as a package insert. While the instructions are typically written or printed materials they are not limited to such. Any medium capable of storing such instructions and communicating them to an end user is contemplated by this disclosure.

The present invention further contemplates a method for controlling cardiac fibrosis and/or heart remodeling in a subject, said method comprising modulating the expression of one or more lncRNA associated with cardiac-specific super-enhancers (SEs) as disclosed herein.

The present invention further contemplates a method of treating and/or preventing a cardiac disease comprising modifying, a target sequence comprising 16 to 25 nucleotides of interest in a single cell or a population of cells, and reintroducing the modified single cell or population of cells into the patient in need thereof.

Preferably, a biopsy or other tissue or biological fluid sample comprising the single cell or the population of cells (e.g. an embryo) may be necessary. Stem cells such as ES cells or pluripotent stem cell that can be generated directly from adult cells, such as iPSCs, are particularly preferred in this regard. Usually, the cell is mammalian cultured cell lines, embryonic stem (ES) cells, and/or induced pluripotent stem cells (iPSCs) and will be selected—or will be derived from—heart cells such as, e.g. cardiac fibroblasts, myocytes, endothelial cells, and vascular smooth muscle cells.

The modified single cell or population of cells is/are then reintroduced into the patient in need thereof by any route of administration and/or delivery methods known in the art as described below.

A further aspect of the invention contemplates a cell or a population of cells comprising one or more nucleic acid(s) encoding i) an sgRNA), or crRNA and tracrRNA, of the invention1, or ii) an nucleic acid encoding an miRNA, siRNA, piRNA, hnRNA, snRNA, esiRNA, shRNA, or antisense oligonucleotide of the invention, or iii) a gene delivery vector of the invention.

Further contemplated in the present invention are nucleic acids encoding v) a single guide RNA (sgRNA), or crRNA and tracrRNA, targeting a regulatory sequence of one or more lncRNA associated with cardiac-specific super-enhancers (SEs), or vi) a single guide RNA (sgRNA), or crRNA and tracrRNA, targeting a genomic DNA sequence encoding an lncRNA associated with cardiac-specific super-enhancers (SEs), or vii) an miRNA, siRNA, piRNA, hnRNA, snRNA, esiRNA, shRNA, or antisense oligonucleotide targeting a regulatory sequence of one or more lncRNA associated with cardiac-specific super-enhancers (SEs), viii) or an miRNA, siRNA, piRNA, hnRNA, snRNA, esiRNA, shRNA, or antisense oligonucleotide targeting a genomic DNA sequence encoding an lncRNA associated with cardiac-specific super-enhancers (SEs).

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein. Various references are cited throughout this Specification, each of which is incorporated herein by reference in its entirety. The foregoing description will be more fully understood with reference to the following Examples.

EXAMPLES

Examples are exemplary of methods of practicing the present invention and are not intended to limit the scope of the invention.

Example 1

Materials and Methods

Primary Cell Culture and Transfection

Neonatal mouse CM and fibroblast isolation—Neonatal C57B6 mice were sacrificed within the first 24 h after birth and beating hearts were collected. Atria and great vessels were carefully dissected away and placed on ice in ADS buffer ($H_2O$, NaCl 116 mM, HEPES 20 mM, $NaH_2PO_4$ 1 mM, KCl 5.4 mM, $MgSO_4$ 0.8 mM, glucose 5.5 mM). The hearts were minced using a sterile sharp razorblade, and placed in a 1.5 ml-tubes (5-6 hearts per tube) containing 1 ml of PIB digestion buffer (ADS buffer; 0.05 mg/ml collagenase type II (Worthington); 1 mg/ml pancreatin; Sigma). Tissues were incubated at 37° C. with shaking for 15 min. Supernatants were then collected in tubes containing complete medium (DMEM 75%, M199 25% ml, penicillin/streptavidin 1×, L-glutamine 1×, horse serum 10%, fetal cow serum 5%; Gibco). PIB buffer was added to undigested tissue fragments and digestion was repeated twice. Cells were collected by centrifugation at 800 rpm for 10 min at room temperature (RT). Pellet was then resuspended in an adequate volume of complete medium (2 ml each 5 hearts). Cells were then plated in 10 cm dishes for 45 min at 37° C., 10% $CO_2$ (pre-plating 1); after this step the non-myocytes adhere and the CMs remain in suspension. Supernatant was transferred to a new 10 cm dish and pre-plating step was repeated (pre-plating 2). After the second pre-plating the supernatant was collected in a new tube, CMs were counted and seeded on gelatin coated 3.5 cm plates ($3\times10^5$ cells per dish). The non-myocytes fraction was cultured in fibroblast medium (DMEM, fetal cow serum 10%, penicillin/streptavidin 1×) and seeded into 10 cm dishes. Cells were split using trypsin to minimize CMs contamination. Confluence was maintained below the 85% and medium was changed every second day.

Adult mouse cardiac fibroblast isolation—12-week old C57/BL6 were injected with 100 U of heparin (Liquerin) 30 min before being sacrificed to avoid blood coagulation in the heart. Beating hearts were removed and washed in cold PBS. Then, hearts were canulated through the aorta and the vessel was tied using a surgical rope. Using a 1 ml syringe, HBSS solution (hanks balanced salt solution, GIBCO) was pumped in the heart through the aorta in order to wash out the blood. In the same way, 1 ml of digesting solution (HBSS; 2 mg/ml Collagenase type II (Worthington); 0.05 mg/ml Protease XIV; Sigma)) was pumped in the heart followed by 5 min of digestion at 37° C. This step was performed 3 times each heart.

After the third digestion, atria and big vessels were removed and the remaining ventricles were minced and resuspended in complete medium (DMEM, penicillin/streptavidin 1×, fetal cow serum 10%). The solution was pipetted up and down 10-20 times to reach a single cell suspension and the supernatant was collected avoiding undigested pieces. Cells were collected by centrifugation at 800 rpm for 10 min at RT. The pellet was resuspended in adequate volume of complete medium and cells were plated in 10 cm dishes overnight (pre-plating 1). After this step, the non-myocytes adhere and the CMs remain in suspension. Supernatant was transferred to a new 10 cm dish and pre-plating step repeated for another 24 h (pre-plating 2). Fresh complete medium was added to the pre-plating dishes to culture the non-myocytes cells and the supernatant was discarded. Cells were split to maintain a confluence not over the 85% and medium was changed every two days.

Mouse lung and tail fibroblast isolation—The lungs and the tail tips were collected from 12 weeks old C57/BL6 and washed in HBSS (Gibco). They were both minced using a sterile and sharp razorblade, and placed in a 2 ml tubes (2 lungs per tube or 5 tails per tube) containing 1 ml digestion buffer (HBSS+10 mg/ml Collagenase type II, Worthington). Cells were incubated at 37° C. with shaking for 40 min. After digestion fibroblast medium (DMEM, Fetal Cow Serum 10%, Penicillin/streptavidin 1×) was added and cells were collected by centrifugation at 800 rpm for 10 min at RT. The supernatant was discarded. The cellular pellet was resuspended in proper volume of fibroblast medium and then filtered into a 70 um strainer to remove undigested pieces. Cells were counted and seeded in 10 cm dishes. Cells were split to maintain a confluence not over 85% and medium was changed every two days.

Human fibroblasts—Adult human dermal fibroblasts were purchased (Gibco). Primary cell cultures of human CFs were obtained by mechanical tissue enzymatic digestion with collagenases (Roche) and explant outgrowth from atrial samples obtained as discarded surgical tissue. Cultures of primary CFs were shown to express specific fibroblasts markers (i.e. vimentin) and to respond to TGF-β (1 ng/mL) stimulation. Cells were plated at a density of 5000 cells/$cm^2$ and maintained in a fibroblast medium (low glucose DMEM (Gibco) with fetal bovine serum (10%; Sigma), fibroblast growth factor-2 (FGF-2; 5.8 μg/μL; Peprotech) glutamine (2.5 mM; Gibco) penicillin/streptomycin (1%; Gibco), Fungizone (0.1%; Gibco) and HEPES (1.5%; Lonza). Medium was changed every 48 hours. Once cells reached a 60-70% confluence cells were starved in medium without fetal bovine serum (and FGF-2 0.285 μg/μL) for 2, 4, 8, 14, 24 or 40 hours. Subsequently, cells were collected for further analysis. Human dermal fibroblasts were used in passages between 3 and 6 and human CFs in passages 2 to 4. Between 6 and 10 independent samples were analyzed for each condition.

GapmeR transfection in mouse primary cell—Adult CFs, neonatal CFs and lung fibroblasts ($3.5\times10^5$ cells per 3.5 cm dish; passage 2) and CMs ($1\times10^6$ cells per 3.5 cm dish) were cultured overnight. The next day, medium was changed two hours before transfection. Then, a final concentration of 10 nM (if not differently specified in the text) of LNA lncRNA GapmeRs (GapmeR-Wisper or GapmeR-negative control A or GapmeR-Wisp2) (Exiqon) was transfected on cells using Xtreme gene HP DNA transfection reagent (Promega). After 48 hours, medium was changed and cells were collected for future experiments. Total RNA was obtained using miRNeasy kit (Qiagen) and the knock down confirmed by qRT-PCR.

GapmeR transfection in human CFs—Transfection was performed in 25 $cm^2$ flasks in cells at 80% confluence. A final concentration of 25 nM of LNA lncRNA GapmeRs (GapmeR-Wisper or GapmeR-negative control A; Exiqon) was transfected on cells using Xtreme gene HP DNA transfection reagent (Promega) in complete medium. After 24 hours, cells were kept in normal medium or exposed to serum starvation for another 24 hours, and subsequently were collected for further studies. Three independent samples were analyzed for each condition.

Animal Experiments—Tissue Collection and Preparation

Mice were sacrificed by deep anesthesia followed by cervical dislocation, and organs were collected. Hearts were dissected from sham and MI mice at different time points after artery ligation. Atria and big vessels were eliminated. The remaining ventricles were rinsed in diethylpyrocarbonate (DEPC)-treated PBS to minimize residual blood contamination. Furthermore, the ventricles were divided in 3 parts: top section (from the top to the ligature), central section (from the ligature to the center of the infarcted area) and the tip of the heart (from the center of the infarcted area to the bottom). The heart tip (50% viable muscle, 50% infarcted zone) was used to collect total RNA. The central section was fixed in formalin and embedded in paraffin. The top section was snap frozen in liquid nitrogen and stored at −80'C for future analysis.

RNA Isolation, cDNA Preparation and Quantitative PCR Analysis

Total RNA from tissues and cultured cells isolated from mice was extracted using miRNeasy kit (Qiagen) according to the manufacturer's instructions and quantified with Nanodrop instrument. The quality control was performed with a Agilent 2100 bioanalyzer (Agilent Technologies). Two steps cDNA synthesis was performed with SuperScript II (Invitrogen), and quantification was carried out using QuantStudio 6/7 (Thermofisher). Gene expression was normalized to Gapdh and quantified using the ΔΔCt method.

Total RNA from human cells was obtained using the Maxwell 16 LEV simplyRNA Purification Kit (Promega) according to manufacturer's instructions, and was quantified with a Nanodrop instrument. Reverse transcription was performed using the high capacity cDNA reverse transcription kit (Applied Biosystems). Real-time PCR for collagen-related genes was performed with a StepOne Plus Real-time PCR system according to the manufacturer's recommendations (Applied Biosystems) using specific TaqMan fluorescent probes. Data were normalized to ribosomal 18S expression. WISPER and WISP2 expression were analyzed with a 7900HT Fast Real-Time PCR system (Applied Biosystems) using the power SYBR green PCR master mix (Applied Biosystems) and specific primers. Gene expression was normalized to GAPDH.

Western Blotting

Proteins were extracted from neonatal CFs transfected with GapmeR-Wisper (10 nM) or GapmeR-Scrambled (10 nM) using lysis buffer (50 mM Tris-HCl, 150 mM NaCl, 0.25% DOC, 1% Nonidet P-40, 1% Triton X-100 containing protease and phosphatase inhibitors (Roche)). Proteins were resuspended in SDS-PAGE buffer, separated on acrylamide gels and transferred to PVDF membranes (BioRad). Membranes were incubated with mouse monoclonal anti-α-SMA primary antibodies (Sigma, 1:2000 dilution), and then with horseradish-conjugated secondary antibodies (Amersham Bioscience, 1:2000 dilution). α-SMA abundance was quantified by densitometry and normalized to the total amount of proteins.

Thymidine Incorporation Assay

Adult CFs and lung fibroblasts were transfected with 10 nM of GapmeR-Wisper or GapmeR-Scrambled for 24 h. $4\times10^3$ cells/well were seeded in 96 round bottom-well plates in quadruplicate. 1 ρCi of $[H^3]$-Thymidine was added in each well at 0 h, 24 h and 48 h after cell seeding, and incubated for 18 h at 37° C. Cells were then harvested and transferred into a filter plate. Radioactivity was measured using a scintillation beta-counter (TopCount, Canberra Packard). Measurements were performed in quadruplicate for each condition in 5 independent experiments and normalized to 0 h values.

Wound Closure Assay

Adult CFs and lung fibroblasts were transfected with 10 nM of GapmeR-Wisper or GapmeR-Scrambled for 48 h. $3.5\times10^5$ cells were seeded in 3.5-cm well and let them attached overnight. The scratch test was performed using a sterile 10 μl filter tip. Medium was replaced twice to remove floating cells. Three pictures for each condition were taken at 20× magnification every 24 hours. The size of the wound has been measured using ImageJ. Measurements were performed in triplicate for each condition in at least 3 independent experiments and normalized to 0 h values (100%).

Annexin V-Positive Cells Quantification

Adult CFs and lung fibroblasts were transfected with 10 nM of GapmeR-Wisper or GapmeR-Scrambled. Transfected cells were collected after 48 h and resuspended in FACS medium. Cells were stained using the FITC Annexin V Apoptosis detection Kit (BD Pharmingen) according to the manufacturer's instructions. Annexin V and PI signals were quantified with a Galios FACS apparatus within 30 min after staining. Results were analyzed with FlowJo.

Wisper In Situ Hybridization

Infarcted (14 days post-MI) and sham-operated hearts were fixed for 48 h in 10% neutral buffered formalin and sections of 4 m were obtained. Sections were de-waxed, dehydrated, air-dried briefly and incubated in 1.3 mg/ml Pepsin/0.1 mM HCl solution for 5 min at 37° C. After a brief wash in DEPC MQ, sections were incubated overnight at 42.5° C. in 1× hybridization buffer (ENZO Life sciences,) with either 100 nM Wisper DIG labeled probe (Exiqon) or a scrambled control probe. The following day the sections were washed once in 5×SSC and twice in 0.2×SSC at hybridization temperature. Subsequently, sections were blocked in DIG blocking buffer from the DIG Wash and Block Buffer Set (Roche) for 20 min followed by a 45 min-incubation in 1:500 anti-DIG-AP, Fab fragments (Roche). Sections were washed 3×5 min with TBS and incubated 3 min in DIG detection buffer at RT. Alkaline phosphatase signal was detected by using NBT/BCIP tablets (Roche) for 4 hours at 30° C. in darkness. Finally, sections were counterstained with fast red (Sigma) briefly washed in MQ, quickly dehydrated through an ethanol gradient and mounted with entellan (EMS). Pictures were taken using a Nikon Stereomicroscope SMZ 25 at different magnifications.

BrdU Labeling and Detection

Mice were supplied with a solution of 10 mg/ml 5-Bromo-2-deoxyuridine (BrdU; Sigma) supplemented with 1% glucose directly in the drinking water for 7 days. The drinking solution was changed every second day. For BrdU detection, frozen heart tissue sections were fixed in 2% paraformaldehyde (PFA) in PBS for 20 min at room temperature. DNA was fragmented by incubation in 2N HCl at 37° C. for 20 min and neutralization in 0.1M Borate buffer, pH 8.5. BrdU detection was performed using rat anti-BrdU antibody (Abcam; 1:100) and Alexa-Fluor 594 conjugated anti-rat antibody (Molecular Probes; 1:250). For BrdU-laminin co-immunostaining, tissue sections were first subjected to immunofluorescence staining to detect protein antigens. Tissue sections were post-fixed with 2% PFA for 10 min at room temperature, and then processed for BrdU detection.

Study Design

The main goal of our study was to evaluate cell-specific lncRNAs as therapeutic targets for cardiac fibrosis and heart disease. Using a stringent pipeline, we selected high priority lncRNA candidates that are associated with cardiac-specific SEs. We focused our attention on one cardiac fibroblast (CF)-enriched lncRNA named Wisper. Loss of function experiments were performed to assess the role of Wisper in the biology of CFs and in fibrosis. Modified ASOs (GapmeRs) were used to silence Wisper expression in mouse CFs. Knockdown experiments were performed in human CFs to verify the evolutionary conserved function of this transcript. For experiments in vivo, LAD artery ligation was chosen as a well-established animal model of myocardial infarction. Experimental groups include at least 6 animals to robustly identify alteration in cardiac function and fibrosis. Mice were randomly assigned to treatment groups. To test if Wisper may hold therapeutic potential in cardiac fibrosis, we performed loss of function experiments in vivo via GapmeR injection. In the preventive approach, injection was performed three days before myocardial infarction. In the therapeutic approach, GapmeRs were injected 2 and 9 days after infarction. GapmeR injection and echocardiographic measurements were double blinded until statistical analysis. Cardiac fibrosis was quantified by Masson's trichrome staining on heart sections. All sample measurements were blinded. In addition, to evaluate the tissue specificity of Wisper expression, we took advantage of the one-kidney one-clip (1K1C) model of renovascular hypertension in the mouse. This model is characterized by the development of cardiac hypertrophy and fibrosis secondary to volume-dependent hypertension. Fibrosis also develops in the clipped kidney, allowing direct comparison of Wisper expression in two different fibrotic organs. WISPER human ortholog was identified and detected in RNA isolated from human cardiac biopsies of patients suffering from aortic stenosis. This pathology is associated with extensive myocardial fibrosis that directly contributes to left ventricle dysfunction and heart failure. Samples of cardiac tissue from AOS patients (n=26) were divided in two groups after analyzing the distribution for collagen volume fraction as described in the text. No data were excluded in this analysis.

RNA-Seq Based lncRNA Profiling after Myocardial Infarction

RNA-Seq on infarcted and sham-operated hearts (14 days after infarction), ab initio transcript reconstruction, differential expression analysis of lncRNAs, heart-specificity analysis and human ortholog identification datasets were previously described (29).

Super-Enhancer Mapping to Human lncRNA Orthologs

The locations of super-enhancers were downloaded from (12). These regions were defined using H3K27ac ChIP-Seq from the Epigenome Roadmap (56). LncRNAs arising from super-enhancers and typical enhancers were determined by genomic overlap.

Animal Experiments

Animal experiments were approved by the Government Veterinary Office (Lausanne, Switzerland) and performed according to the University of Lausanne Medical School institutional guidelines. Myocardial infarction model—Myocardial infarction in mice (numbers of animals per group are in the figures legends) was induced as previously described (57). Briefly, male C57/BL6 (Charles River) at 12 weeks of age were anesthetized by i.p. injection of ketamin/xylazine/acepromazin (65/15/2 mg/kg), and placed on artificial ventilation. After left thoracotomy, the pericardium was gently opened and a 7.0 silk ligature (Aesculap) was tied around the LAD artery near the insertion of the left auricular appendage. Occlusion of the artery was verified by the rapid blanching of the left ventricle. In sham-operated mice, the ligature was placed in an identical location but not tied. After surgery, mice were gradually weaned from the respirator until spontaneous respiration was resumed and replaced in the cage.

One-kidney one-clip renovascular hypertension in mice—One-kidney one-clip (1K1C) renovascular hypertension in mice was produced as previously described (35). Briefly, a left lateral abdominal incision is used to expose the kidney. A clip (0.12 mm-opening) is placed around the left renal artery in order to reduce renal blood flow. Another incision is made in the right lateral abdominal wall and a right nephrectomy is performed. Animals develop volume overload-dependent cardiac hypertrophy and renal failure.

Echocardiography—Transthoracic echocardiography was performed using a 30-MHz probe and the Vevo 770 Ultrasound machine (VisualSonics). Mice were lightly anesthetized with 1% isoflurane, maintaining heart rate at 400-500 beats per minute, and placed in dorsal recumbency on a heated 37° C. platform. The heart was imaged in the 2D mode in the parasternal long-axis view. From this view, an M-mode curser was positioned perpendicular to the interventricular septum and the posterior wall of the left ventricle (LV) at the level of the papillary muscles. LV free wall thickness in diastole (LVWT d) and in systole (LVWT s) as well as LV diameter in diastole (LVD d) and in systole (LVD s) were measured according to the American Society of Echocardiography guidelines. The measurements were taken in 3 separate M mode images and averaged. Ejection fraction (EF) was calculated using the formula % EF=[(LVVD−LVVS)/LVVD]×100, where LVVD and LVVS are LV volume in diastole and systole respectively.

GapmeR delivery in vivo—GapmeR-Wisper and GapmeR-Scrambled control A (Exiqon) were diluted in NaCl 0.9% isotonic solution to obtain the final exact concentration (5, 10 or 15 mg/kg) just before the injection. GapmeRs were delivered i.p. using a U100 insulin 0.3 ml syringe and a 30GX8 mm needle.

Primary Cell Culture and Transfection (as Described Above)

Neonatal mouse CMandfibroblasts—Cells were obtained from neonatal C57/BL6 mice.

Adult mouse cardiac, lung and tailfibroblasts—Cells were obtained from 12-week old C57/BL6 mice.

Humanfibroblasts—Adult human dermal fibroblasts were purchased from Gibco. Primary cell cultures of human CFs were obtained by tissue enzymatic digestion with collagenase and explant outgrowth from atrial samples as previously described (58).

GapmeR transfection in mouse primary cell—Adult CFs, neonatal CF, lung fibroblasts and CMs were transfected with 10 nM (if not differently specified in the text) of LNA lncRNA GapmeRs (GapmeR-Wisper SEQ ID No. 10 or scrambled GapmeR SEQ ID No. 9 or GapmeR-Wisp2 SEQ ID No. 11; Exiqon).

GapmeR transfection in human CFs—Fibroblasts were transfected with 25 nM of LNA lncRNA GapmeRs (GapmeR-Wisper or scrambled GapmeR; Exiqon).

CRISPR-on Assay

CRISPR-based gain-of-function was used to activate Wisper expression in P19CL6 cells (RCB2318, RIKEN Cell Bank, Japan). Cells were cultured in DMEM with 10% FCS and transfected with component of the synergistic activation mediator described by the Zhang laboratory in combination of a Wisper-targeting guide RNA engineered to contain two MS2 aptamers (sgRNAMS2; Addgene plasmid #61424) and containing the following sequence: GTCGACTCTGCTATACTCCA (SEQ ID No. 13). Plasmids were transfected at a 1:1 ratio using Lipofectamine 2000 (Life Technologies) according to manufacturer's instructions. Total RNA was isolated 48 h after transfection using miRNeasy kit (Qiagen) and subjected to qRT-PCR.

Cytoplasmic and Nuclear Compartment Fractionation $2\times10^6$ adult CFs were washed twice with cold PBS. Nuclear and cytoplasmic RNA fractions were isolated using the Cytoplasmic and Nuclear RNA purification kit (Norgen Biotek Corp) according to the manufacturer's instructions. Total RNA was isolated from $1\times10^6$ adult CFs using miRNeasy kit (Qiagen) and used as input.

Immunohistochemistry

Cardiomyocytes—CMs were transfected with 10 nM of GapmeR-Wisper or GapmeR-Scrambled for 48 h. Cells were then fixed for 10 min in 4% paraformaldehyde in PBS and permeabilized with 0.2% Triton X100 in PBS. After treatment with blocking buffer (PBS containing 0.001% Triton X100, 1% BSA and 1% FCS), cells were incubated overnight at 4° C. with anti α-sarcomeric actinin antibodies (1:400; Sigma). One day after, cells were washed 3 times and incubated 1 h at RT in the dark with conjugated anti-mouse donkey secondary antibodies (1:500; Alexa Fluor 488, Life Technology). Nuclei were stained with DAPI (Invitrogen). Unbound antibodies were washed out with PBS 0.1% Tween. Subsequently, coverslips were mounted with Fluoromount-G (Southern Biotech) and analyzed with an inverted Axiovision Observer Z1 fluorescence microscope (Carl Zeiss). Five pictures for each different condition were taken. The dimension of the cells was measured using ImageJ. CMs were counted as α-sarcomeric actinin-positive and DAPI positive cells while non-myocyte cells were counted as α-sarcomeric actinin-negative and DAPI positive cells.

Cardiac Fibroblasts—Cells were transfected with 5 nM of GapmeR-Wisper or GapmeR-Scrambled for 48 h. Cells were fixed as described above and incubated overnight at 4° C. with anti-TIAL antibody (1:200; Abcam, Ab129499). One day thereafter, cells were washed 3 times and incubated 1 h at RT with conjugated anti-rabbit goat secondary antibodies (1:250; Alexa Fluor 488, Life Technology). Actin filaments were stained using Texas Red-X Phalloidin (1:100; Life Technologies; T7471) and nuclei were stained with DAPI (Invitrogen). Unbound antibodies were washed out with PBS 0.1% Tween. Subsequently, coverslips were mounted with Fluoromount-G (Southern Biotech) and TIAL localization was analyzed with an inverted Axiovision Observer Z1 fluorescence microscope (Carl Zeiss).

Assessment of Cardiac Fibrosis

Hearts were harvested from sham-operated and MI mice, and atria and big vessels were eliminated. Cardiac tissues were fixed in 4% formalin overnight. Paraffin tissue sections were processed for Masson's trichrome staining using standard histological procedures. The percentage of fibrotic tissue was determined by measuring collagen deposition (blue) on Masson's trichrome-stained sections using ImageJ.

RNA Pulldown

Biotinylated Wisper sense and Wisper antisense were in vitro transcribed using the T7 or T3 RNA polymerase (Promega) and Biotin RNA Labeling Mix (Roche), then purified with Quick Spin columns (Roche) according to manufacturers' instructions. 4 μg of biotinylated RNA was denaturated for 5 min at 65° C. in RNA Structure Buffer (10 mM Tris-HCl, 10 mM $MgCl_2$, 100 mM $NH_4Cl$) and cooled to RT. In brief, freshly harvested cardiac fibroblasts were washed in ice-cold PBS. Cells were lysed in 1 ml Lysis Buffer (25 mM Tris-HCl pH 7.4, 150 mM NaCl, 5 mM MgCl2, 0.1 mM EDTA, 0.5% NP40, 1 mM DTT, 1 mM PMSF, 0.1 U/μl RNase inhibitor (promega) and 1× protease inhibitor cocktail (Sigma)). Streptavidin Dynabeads were washed in NT2 Buffer (50 mM Tris-HCl pH 7.4, 150 mM NaCl, 1 mM MgCl2, 0.05% NP40, 1 mM DTT, 20 mM EDTA, 400 mM Vanadyl-ribonucleoside, 0.1 U/μl RNase inhibitor (Promega) and 1× protease inhibitor cocktail (Sigma)) and used to preclear the lysate (20 min at 4° C.). The pre-cleared cell lysate was incubated with biotinylated RNA along with 0.1 U/μl RNase inhibitor (Promega) and 20 μg/ml Yeast tRNA (ambion) for 1.5 h at room temperature followed by addition of 60 μl of Streptavidin Dynabeads for 1.5 h. The beads containing the RNA protein complex were washed thrice in NT2 Buffer then were directly boiled in SDS-gel loading dye. Retrieved proteins were loaded on a 12% polyacrylamid gel in denaturating SDS-PAGE buffer and visualized with Candiano colloidal Coomassie staining. Mass spectrometry were performed at the PAF (Protein Analysis Facility, University of Lausanne, Switzerland). Analysis of the pulled-down proteins was performed using Scaffold4. Proteins enrichment was calculated by Fisher's exact test.

Western Blot of RNA Pulldown

4% of the samples used for RNA pulldown were utilized as input. Proteins were resolved on 10% SDS-PAGE minigels and transferred to PVDF membranes (BioRad). The membrane were blocked and incubated with primary antibody against TIAR (Santa Cruz Biotechnology, Inc) at 4° C. overnight. The primary antibody was detected using infrared IrDye antibody regents and scanning the membranes using Odyssey Infrared Imaging System (LiCor Biosciences). Protein quantification on the scanned Western blots was performed using the software provided with the scanner (LiCor Biosciences). 20 μg of mouse TIAR Lysate (Santa Cruz Biotechnology) was used as a control.

RNA Immune Precipitation (RIP)

Cells were harvested in Lysis Buffer as described previously. Supernatant was pre-cleared with Dynabeads G (Invitrogen). The pre-cleared lysate was incubated with normal IgGor with anti-TIAR antibody (Santa Cruz Biotechnology) at 4° C. overnight followed by addition of 50 ul of Dynabeads G for 1 h at 4° C. The immunoprecipitated complexes was washed thrice in NT2 Buffer and eluted in 500 μl of Quiazol. Total RNA extraction and cDNA synthesis were performed as described before. Real-Time PCR system (Applied Biosystems) was then used to measure expression of Wisper, Wisp2 and Plod2.

Human Tissue Sampling

The present study is conformed to the principles of the Declaration of Helsinki. All subjects were duly informed and gave written consent. Samples were collected as previously described (46).

Collagen volume fraction (CVF)—The fraction of myocardium occupied by collagen was quantified as previously described (46). A cluster analysis was performed according to the CVF values to define the non-severe (CVF<12%; n=11) and the severe (CVF>12%; n=15) fibrosis groups (46).

Echocardiographic analysis—LV mass was measured from M-mode recordings LV mass index (LVMI) was calculated by dividing LV mass by body surface area. LV end-systolic and end-diastolic volume indexes (LVESVI and LVEDVI, respectively), corresponding to the LV volumes corrected by body surface area, and the LVEF were determined in all patients. The following pulsed Doppler measurements were obtained: maximum early (VE) transmitral velocity in diastole, maximum late (VA) transmitral velocity in diastole, the deceleration time of the early mitral filling wave (DT), and the isovolumetric relaxation time (IVRT).

Sequencing of RNA Isolated from GapmeR-Transfected Adult CFs

Total RNA was isolated from adult CF transfected (10 nM, 48 h) with GapmeR-Wisper (n=4) or GapmeR-Scrambled (n=4) using the miRNeasy kit (Qiagen). Sequencing libraries were prepared according to Illumina RNA Seq library kit instructions with PolyA selection. Libraries were sequenced with the Illumina HiSeq2000 (1×100 bp). Purity-filtered reads were adapter and quality trimmed with Cutadapt (v. 1.3), and filtered for low complexity with seq_crumbs (v. 0.1.8). Reads were aligned against the *Mus musculus*.GRCm38.82 genome using STAR (59) (v. 2.4.2a). The number of read counts per gene locus was summarized with htseq-count (60) (v. 0.6.1) using *Mus musculus*.GRCm38.82 gene annotation. Quality of the RNA-Seq data alignment was assessed using RSeQC (61) (v. 2.3.7). Reads were also aligned to the *Mus musculus*.GRCm38.82 transcriptome using STAR (59) (v. 2.4.2a), and the estimation of the isoform abundance was computed using RSEM (62) (v. 1.2.19). Statistical analysis was performed for genes and isoforms independently in R (R version 3.1.2). Genes/Isoforms with low counts were filtered out according to the rule of 1 count per million (cpm) in at least 1 sample. Library sizes were scaled using TMM normalization (63) (EdgeR v 3.8.5) and log-transformed with limma voom function (R version 3.22.4). Statistical quality controls were performed through pairwise sample correlations, clustering and sample PCA. Replicates cluster together and are well separated between conditions. Differential expression was computed with limma (64) by fitting data into a linear model, adding the factor for the batch effect and comparing GapmeR versus control conditions. The P-values were adjusted for multiple comparisons using the Benjamini-Hochberg method (65), controlling for false discovery rate (FDR) or adjusted P value.

Statistical Analysis

GraphPad Software (version 6 or 7) was used for statistical analysis. Data throughout the paper are expressed as mean±SEM. Statistical significance between two columns was assessed by two-tailed unpaired Student's t test; for more than two columns, one-way ANOVA (Analysis of variance; Fisher's LSD test) analysis was used. Two-way ANOVA (Fisher's LSD test) was used to evaluate statistical significance between two or more groups. Correlation analysis was performed with Pearson (R or $R^2$ values; 95% confidence interval) or Spearman (R; 95% confidence interval) test. Significance in percentage of animal survival was calculated with Log-rank (Mantel-Cox) test. P values <0.05 were considered significant in all events.

Results

Wisper is Cardiac SE-Associated lncRNAs

Emerging evidence suggests that SEs and the lncRNAs associated with them represent specific regulators of cell state and identity during development and disease (10). Based on this cogent rationale, we set out to identify SE-associated lncRNAs modulated in the damaged myocardium, which were conserved among mouse and human genomes (66). Previously, our laboratory identified 1521 novel lncRNAs in the murine heart (29). A large number of these novel lncRNAs were associated with active cardiac-specific enhancers. Using this transcriptomic dataset, we first filtered for all novel lncRNAs that were classified as heart-enriched. To facilitate downstream functional assessment and alleviate any confounding interpretations based on overlapping protein coding genes (PCGs), we further filtered lncRNAs for those that were intergenic and differentially expressed in the border zone (BZ) 14 days post-MI, resulting in the inclusion of 149 lncRNAs (66)). To identify putative human orthologs, these transcripts were mapped to the human genome using TransMap, a cross-species alignment tool. Globally, of these 149 mouse lncRNAs, 130 were predicted to have human orthologs. Considering that lncRNAs associated with TEs and SEs likely represent high priority functional candidates (10), we next examined an enhancer catalogue generated in 23 human tissues that utilized histone 3 lysine 27 acetylation (H3K27Ac) marks and the ROSE algorithm to identify tissue-specific TEs and SEs (12). We found that 37 (28%) of our lncRNAs map to TEs and 6 (5%) mapped to human heart-specific SEs. The most upregulated lncRNA in the infarcted mouse heart was one of the six SE-associated lncRNAs, supporting the notion that these transcripts could play important roles in the transcriptional reprogramming that underpins cardiac remodeling (66). To dissect the cardiac cell specificity of the six SE-associated lncRNAs, expression was evaluated in CFs and CMs isolated from the adult murine heart. Expression of these transcripts and canonical PCGs was determined via qRT-PCR (FIG. 1). The CM-specific PCGs, Tnni3 and Actc1, were highly enriched in CM-preparations whereas CF-specific PCGs as Col1a1, Tgfb2, Postn, Vim were specifically enriched in CFs. Among the SE-associated lncRNAs, two were significantly enriched in CMs (P=0.009 and 0.42 respectively) while one lncRNA was highly enriched in CFs (P<0.001). In fact, this transcript was more enriched in CFs than the CF-specific PCGs, suggesting it could have important functions in this particular cardiac cell type and therefore could play a role in the fibrotic response of the heart after infarction. Proximal to this lncRNA was the gene encoding the matricellular protein CcnS (Wisp2), which had recently been implicated in pathological myocardial fibrosis (31). We therefore named this lncRNA: WIsp2 SuPer-Enhancer associated RNA or Wisper, and its human ortholog WISPER. This transcript was found substantially conserved in the two species with a 57.3% sequence identity between the two orthologs. Importantly, the SE from which this lncRNA derived was uniquely active in the adult human heart as compared to other tissues (66). Nevertheless, the SE overlapped with WISP2 sequences, suggesting that it contains several constituent enhancers, which may encode different cis-regulatory potential (32). Considering the enrichment of this transcript in CFs, coupled to its upregulation in the BZ after MI, we suspected it could represent an interesting target molecule for the regulation of pathological fibrosis and was selected for further investigation.

Figure 2A:
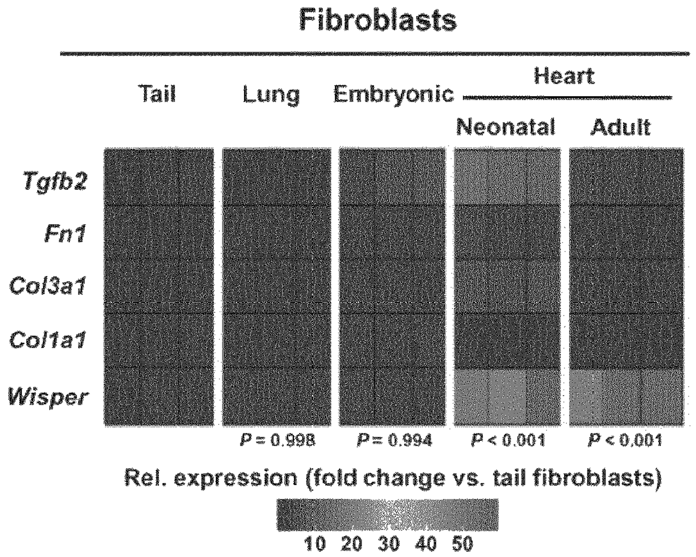
FIG. 2. Wisper is enriched in cardiac fibroblasts and upregulated in fibrotic myocardial tissue. (A) Heatmap representation of Wisper and fibroblast gene expression (relative to tail fibroblasts) in fibroblasts isolated from different tissues. Three independent experiments are shown. P value determined by one-way ANOVA (Fisher's test). (B) Percentage of nuclear (black bar) and cytoplasmic (grey bar) RNA concentrations of Wisper, Gapdh and Tubg1 (cytoplasmic markers), and Neat1 and Xist (nuclear markers) measured by qRT-PCR after subcellular fractionation in cardiac fibroblasts. Data represent mean±SEM (n=4). (C) Ejection fraction (AEF; green line) and systolic left ventricular internal dimension (LVID s; blue line) after myocardial infarction by echocardiography as compared to sham. Three different phases of remodeling are highlighted. (D) Expression kinetics of Wisper and canonical markers of maladaptive cardiac remodeling measured by qRT-PCR. Graphs show means normalized to sham±SEM (n=6 to 10 animals). P values determined by two-way ANOVA (Fisher's test).
Figure 2B:
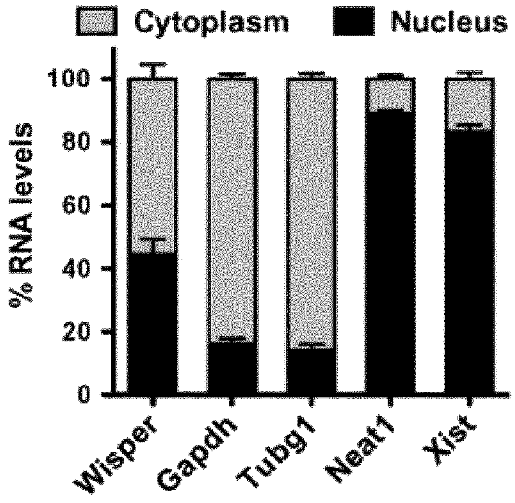

Wisper Expression is Enriched in Cardiac Fibroblasts and Associated with Cardiac Fibrosis Integrative transcriptome analysis using publicly available RNA-Seq datasets demonstrated that Wisper was a heart-enriched transcript (29). To validate this finding, qRT-PCR was conducted using RNA isolated from different adult mouse tissues. Wisper was more expressed in the heart than all other tissues (66). On the other hand, Wips2 expression was not characterized by the same tissue distribution. We next quantified Wisper expression in fibroblasts of cardiac and non-cardiac origins. In comparison to fibroblast-associated PCGs such as Tgfb2, Fn1, Co3a1 and Col1a1, which were similarly expressed in fibroblasts from different sources, Wisper was significantly enriched in fibroblasts isolated from neonatal and adult hearts (FIG. 2A; P<0.001). Importantly, several binding sites for cardiac TFs such as GATA4 and NKX2-5 were identified in the SE element from which WISPER derives (66). This was in contrast to WISP2, which was characterized by distinct TF binding sites at its promoter such as ATOH1 binding sites and E-box that were known to regulate lung-specific expression (66) (33). Finally, lncRNA functions are typically dependent on subcellular localization, with those present primarily in the nucleus involved in chromatin regulation whereas cytoplasmic lncRNAs influence post-transcriptional processes (24). Wisper was found equally distributed between the two subcellular compartments, indicating it could play roles in both transcriptional and post-transcriptional regulatory processes (FIG. 2B).

Figure 2C:
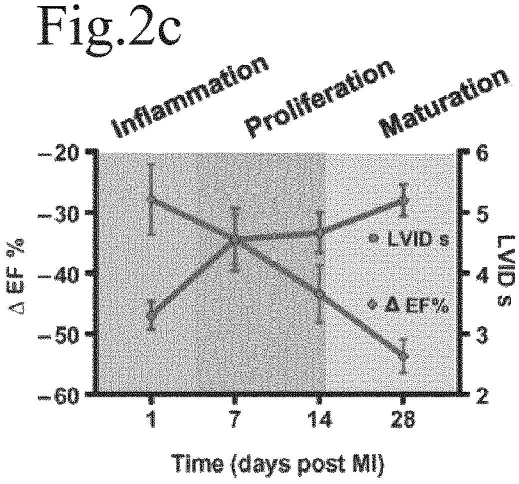
Figure 2D:
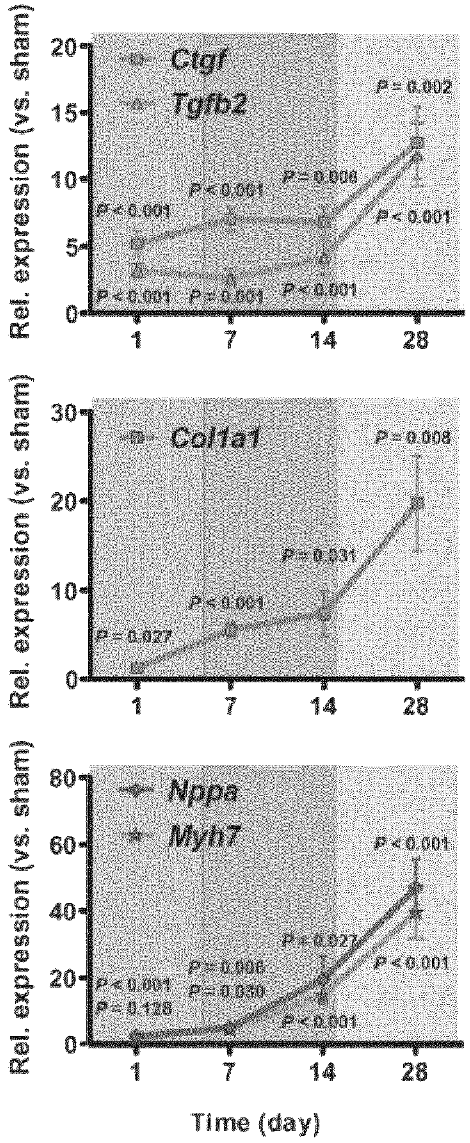
Figure 9A:
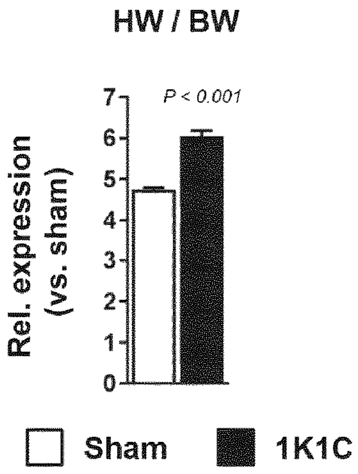
FIG. 9. Wisper is expressed in the stressed fibrotic heart but not in the stressed fibrotic kidney. (A) Cardiac hypertrophy in mice subjected to the one-kidney one-clip (1K1C) model of renovascular hypertension. 1K1C mice: n=8; Sham-operated mice: n=7. Heart weight (HW) to tibial length (TL) ratio. Bars represent mean±SEM. P values determined by Student's t test. (B) Cardiac stress marker expression measured by qRT-PCR in sham and 1K1C mice 14 days after surgery. Bars represent means normalized to sham±SEM. P values determined by Student's t test. (C) Wisper and fibrosis-associated gene expression measured by qRT-PCR in sham and 1K1C mice. Bars represent means normalized to sham±SEM. P values determined by two-way ANOVA (Fisher's test).
Figure 9B:
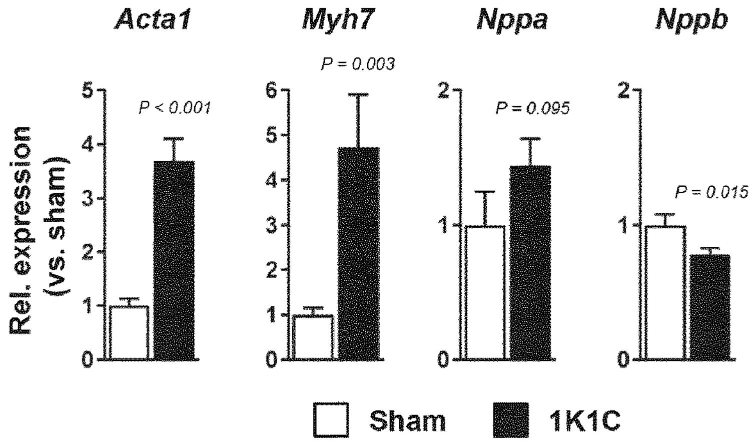
Figure 9C:
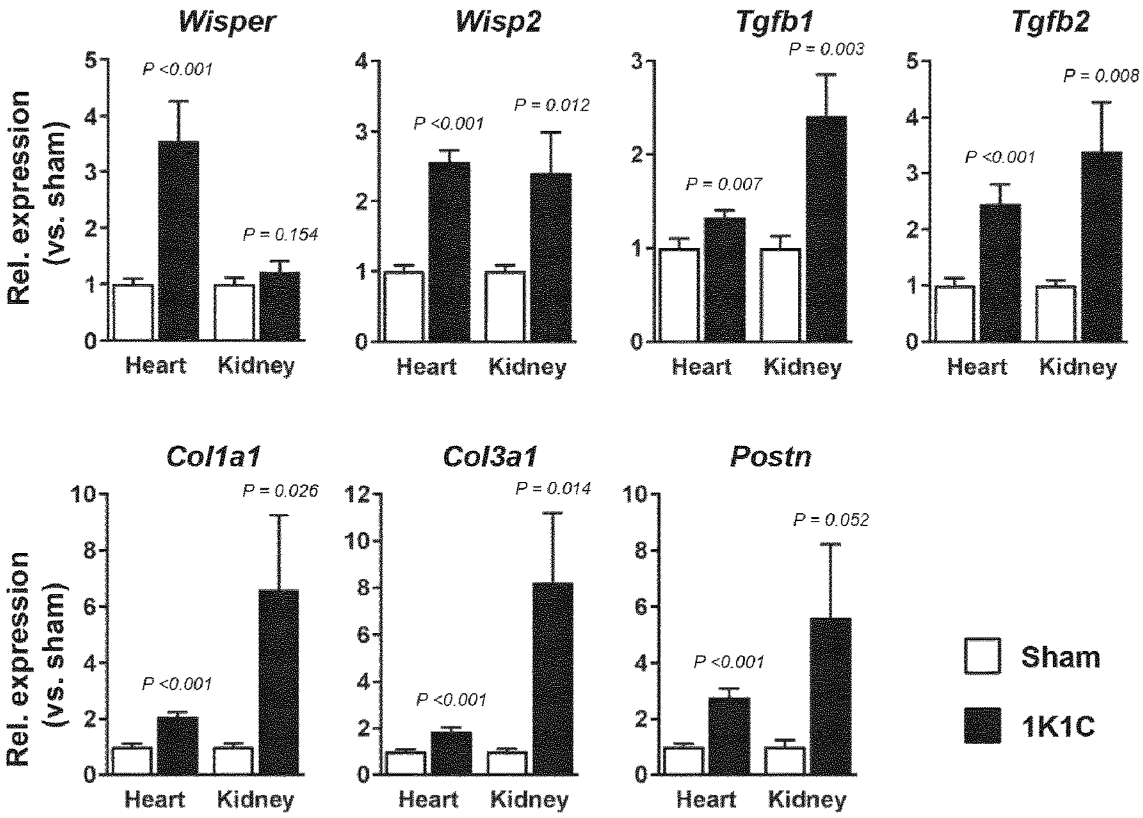

After MI, the myocardium undergoes a remodeling process that is characterized by three distinct phases. These include an inflammatory response (day 1-3 post injury), proliferation and granulation tissue formation (day 7-14), and scar maturation (day 21-28) (34). Pro-fibrotic pathways are typically associated with the proliferative phase, in which differentiation of myofibroblasts and subsequent proliferation, migration and secretion of ECM components take place. In order to assign Wisper to either of these phases, MI was induced in the mouse heart by ligation of the left anterior descending (LAD) artery and Wisper expression was assessed over a 28-day period. Cardiac dimensions and function were assessed by echocardiography (FIG. 2C; Table 1). Gene expression profiling demonstrated the expected expression kinetics for fibrotic and hypertrophy-associated PCGs (FIG. 2D). Importantly, Wisper was maximally expressed 14 days post-MI, corresponding to the proliferative phase in which myofibroblasts migrate to the BZ and actively secrete collagen and other ECM components. The temporal kinetics of Wisper induction implicated this transcript in cardiac fibrosis driving pathological remodeling. To support these findings, RNA in situ hybridization using probes against Wisper was performed on mouse hearts 14 days after infarction. In accordance with Wisper expression in activated fibroblasts, a marked signal was observed in the BZ of infarcted hearts (66). Wisper expression was also detected, albeit less frequently, in the interstitial space of the viable muscle. We therefore evaluated whether Wisper expression correlated with gene programs linked to cardiac fibrosis. Wisper expression was highly correlated with PCGs relevant to ECM deposition (66), and also highly correlated with echocardiographic traits linked to remodeling of the injured myocardium (66). Moreover, in order to evaluate the tissue specificity of Wisper expression under stress conditions, we used a mouse model of renovascular hypertension, namely the one kidney-one clip model (35). Cardiac hypertrophy and fibrosis develop in response to volume overload in this model (FIG. 9A-C). In addition, the single hypoxic kidney is also characterized by extensive fibrosis (FIG. 9C). Strikingly, Wisper was induced in the stressed heart but not in the stressed kidney. In contrast, Wisp2 expression was upregulated in both organs.

Wisper Controls Cardiac Fibroblast Behavior and Survival

Figure 8A:
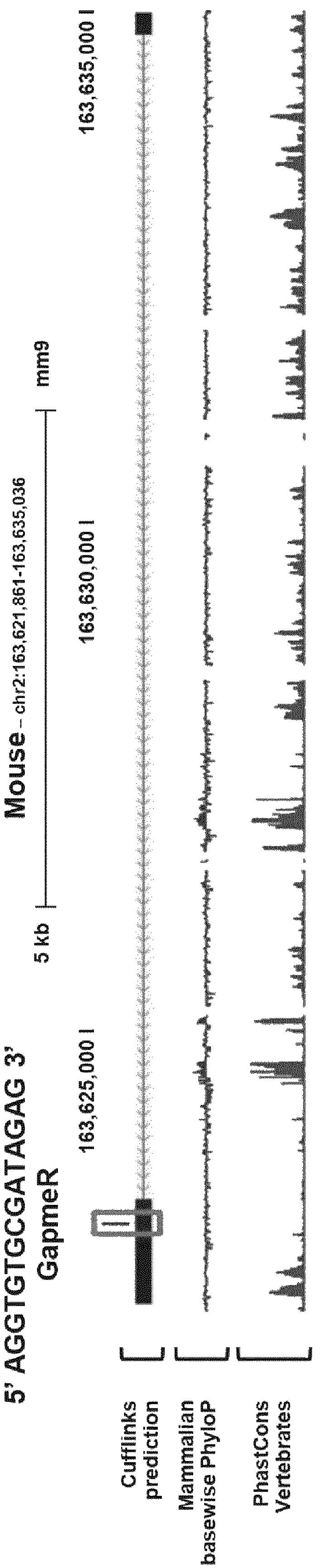
FIG. 8. Conservation between the mouse and human Wisper transcripts. (A and B) UCSC genome browser views of Wisper showing the region targeted by GapmeRs and its sequence in the mouse (A) and human genome (B).
Figure 10:
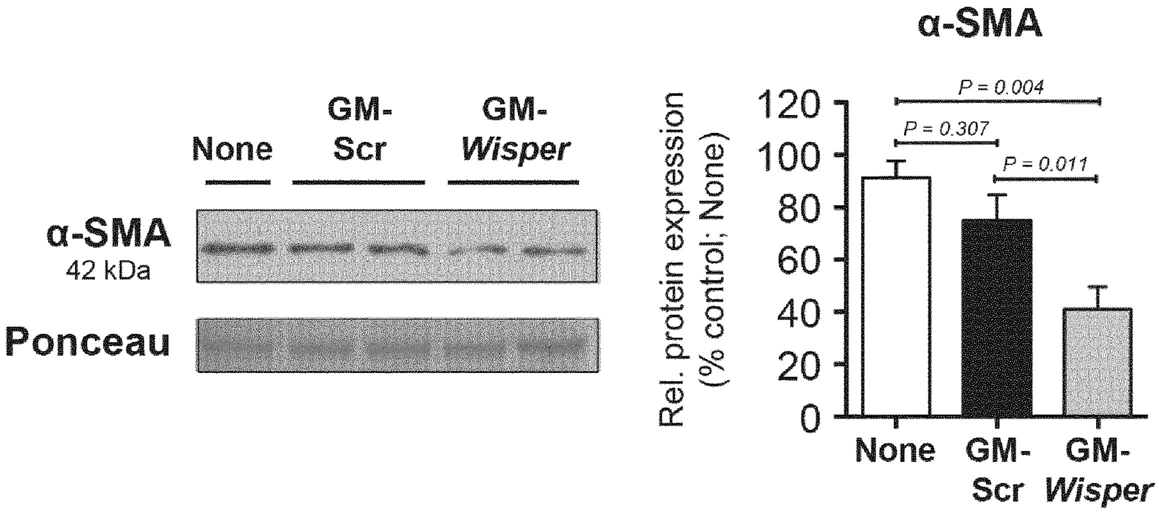
FIG. 10. Effects of Wisper knockdown in neonatal CFs and CMs. α-SMA protein quantification by Western blotting in neonatal cardiac fibroblasts. Cells were kept untreated (None) or transfected with scrambled GapmeRs (GM-Scr) or GapmeRs targeting Wisper (GM-Wisper). Bars represent mean normalized to protein detected by Ponceau staining±SEM (n≥5). Graph shows mean normalized to untreated cells. P values determined by one-way ANOVA.

In order to characterize the functional role of Wisper, a loss of function approach was utilized in isolated adult murine CFs. Modified antisense oligonucleotides (ASOs) called GapmeRs were used to initiate nuclear ribonuclease H-mediated degradation of the transcript and to deplete Wisper in both the nucleus and cytoplasm (FIG. 8A). Titration experiments showed that 10 nM of GapmeRs targeting Wisper was sufficient to achieve maximal knockdown in adult CFs without affecting CF integrity (FIG. 3A). This concentration was therefore used for subsequent experiments. Silencing of Wisper expression resulted in a specific impact on ECM-associated PCG expression (FIG. 3B). Co3a1, Fn1 and Tgfb2 were downregulated, however Col1a1 and Ctgf were not affected. Wisper depletion led also to the downregulation of the proximal PCG Wisp2, suggestive of a possible cis-regulatory role in adult CFs. Considering the effect on gene expression, we suspected Wisper could be fundamentally involved in the transdifferentiation of CFs into myofibroblasts. We therefore isolated neonatal murine CFs, which can be induced to differentiate through cell passaging in vitro. Differentiation of these cells resulted in the upregulation of myofibroblast-specific PCGs such as Tgfb2, Fn1, Col1a1, Co3a1 and αSma (66). Wisper and Wisp2 expression was closely associated with myofibroblast differentiation. Importantly, Wisper depletion in differentiated myofibroblasts resulted in a significant downregulation of Co3a, Fn1, Tgfb2 and αSma expression (FIG. S3B of (66); P<0.001), similar to what was observed in adult CFs (FIG. 3B of (66)). The myofibroblast-associated α-SMA protein was also significantly downregulated (FIG. 10; P=0.011). Again, Col1a1 was not affected by Wisper depletion supporting a specific regulatory role on individual ECM genes.

As Wisper depletion was found to have a large impact on fibroblast identity, we proceeded to evaluate cell behavior after Wisper knockdown in adult CFs. We found a significant decrease in proliferation in CFs 24 hours after Wisper knockdown (FIG. 3C; P<0.001), suggesting that Wisper was important for the proliferative ability of CFs. Using a wound closure assay, we demonstrated a significant attenuation of the migratory ability of Wisper-depleted CFs (FIG. 3D; P<0.001). Finally, apoptosis was assessed in Wisper-depleted CFs via testing annexin V positivity by flow cytometry analysis. At 24 hours post-transfection, there was a five-fold increase in the percentage of apoptotic CFs treated with GapmeRs targeting Wisper (FIG. 3E). In addition, the ratio between Bax and Bcl2 expression indicated an increase in pro-apoptotic signaling in CFs upon Wisper depletion (66). Altogether, these data suggest that Wisper knockdown impacts cell survival in CFs. To confirm the cardiac specificity of Wisper function, we used the same dose of Wisper-targeting GapmeRs in fibroblasts of non-cardiac origin, i.e. lung fibroblasts (66), and observed no impact on expression of fibroblast-associated PCGs (66), proliferation (66), migration (66) and apoptosis (FIG. 3F). Finally, despite being largely CF-enriched, Wisper is also expressed at low concentrations in CMs. Therefore, we also tested the effects of GapmeRs in neonatal CMs to detect any unanticipated effects on these cells (FIG. S3D of (66)). Although slightly decreasing Wisper expression, GapmeR treatment did not impact CM-specific gene expression, structure, cross-sectional area or cell number. Interestingly, the number of CFs, which are typically present in neonatal CM cultures, was reduced following Wisper depletion, suggesting that decreased Wisper expression in CM cultures reflects modulation in contaminating CFs.

Wisper Regulates Specific Cardiac Fibroblast Gene Programs

To determine whether Wisper played a global role in the regulation of specific CF gene programs, RNA-Seq was performed on scrambled and Wisper-specific GapmeR-treated adult CFs. We identified 3153 differentially expressed protein coding genes (PCGs) (fold change >2, adjusted P-value <0.05) in Wisper-depleted CFs, 1337 upregulated and 1816 downregulated (FIG. 4A of (66)). Using Gene Ontology (GO) analysis, we found that upregulated PCGs were associated with biological processes linked to the control of cell cycle and mitosis (FIG. 4B). Furthermore, these PCGs were also associated with mouse phenotypes linked to abnormal control of cell cycle and induction of cell death, both processes observed in Wisper-depleted CFs. Downregulated PCGs were associated with modulation of the immune response and inflammatory phenotypes in the mouse (FIG. 4C of (66)). These findings are consistent with the important roles that CFs play during acute inflammation after infarction (34). Upregulated genes included many important pro-apoptotic molecules (e.g. Dusp6 and Casp3) whereas anti-apoptotic genes were downregulated (e.g. Bcl2l1 and Bcl2a1b) (FIG. 4D of (66)). Similarly, cell cycle inhibitors (e.g. Btg1, and Tob1) were induced upon Wisper deletion whereas cell cycle activators (e.g. Ccnd1) were downregulated. Many regulators of the immune response were also downregulated (e.g. Cxc10). Importantly, key PCGs linked to the ECM (e.g. Co4a6 and Col8a1) were depleted in Wisper GapmeR-treated cells. Furthermore, we also tested the capacity of Wisper to induce a fibroblastic gene program in non fibroblastic cells when enacted at its own site of transcription. We used a CRISPR-based gain-of-function approach (CRISPR-on). P19CL6 cells were transfected with components of the synergistic activation mediator described by the Zhang laboratory in combination with a Wisper-targeting guide RNA engineered to contain two MS2 aptamers (36). Significant Wisper expression was measured 2 days following transfection (P<0.011). In turn, prototypic fibroblast genes were induced. Interestingly, Wisp2 was not activated in these cells (FIG. 4). Considering the cis-based regulatory roles linked to SE-associated lncRNAs, we proceeded to assess the impact of Wisper depletion on proximal PCGs embedded within its topologically associated domain (TAD). Cell-type invariant TADs are typically established during pluripotency and are critical for configuring the three-dimensional chromatin architecture that ensures correct temporal and spatial interactions between distal enhancers and their target promoters. We therefore utilized publicly available high-throughput confirmation capture datasets from mouse embryonic stem cells to interrogate the topological nature of this locus (FIG. S4A of (66)). Of the ten PCGs within the Wisper-harboring TAD, five were differentially expressed upon Wisper depletion in adult CFs, and among them Wisp2. We therefore evaluated whether Wisper could exert its action via cis-regulation of Wisp2 expression. We examined the specificity of the gene expression programs in CFs after GapmeR-mediated Wisp2 depletion, which resulted in a significant loss of Wisp2 expression (P<0.001) without affecting Wisper concentrations (FIG. 4F of (66)). The canonical ECM proteins previously examined, whose expression was modified by Wisper depletion, were not impacted by Wisp2 knockdown. These data support a role for Wisper in dictating gene programs associated with cell identity and behavior in CFs, independent of Wisp2 expression. Finally, the RNA-Seq data also allowed us to assess the impact of Wisper depletion on the annotated long noncoding transcriptome (FIG. S4B of (66)). Among the 435 upregulated lncRNAs, well-characterized lncRNAs such as Neat1 and GasS were included (FIG. S4C of (66)). Conversely, 276 lncRNAs were downregulated; among them, Malat1, Ftx and Firre have all been implicated in cell cycle control and apoptosis in various cell types (37, 38).

Wisper is associated with TIA1-related protein, and regulates Lysyl hydroxylase 2 expression Many lncRNAs exert their function via interaction with proteins. In order to identify relevant Wisper-binding proteins, we performed a lncRNA pulldown assay. A biotinylated Wisper probe was therefore used as a bait to selectively extract putative Wisper protein partners from an adult cardiac fibroblast lysate (FIG. S4D and E of (66)). An antisense Wisper transcript was used as control. Then, proteins were identified by shotgun mass spectrometry. Four proteins were detected as specifically associated with Wisper, namely TIAR, PTB3, DIS3L2 and CELF2 (FIG. 5A). All four RNA binding proteins have been implicated in RNA processing. TIAR, PTBP3 and CELF2 are splicing factors, and DIS3L2 has been involved in target mRNA-mediated microRNA degradation as well as mRNA decay (39-43). These proteins demonstrate relevant functions as regulators of differentiation, proliferation and apoptosis during development and in adulthood. Nevertheless, protein inference based on peptide analysis unambiguously identified TIAR (TIA1-related protein also referred to as TIA1 cytotoxic granule-associated RNA binding protein-like 1 or TIAL1) as a prime candidate with 26% amino acid coverage (102/392). More importantly, TIAR has been related to tissue fibrosis via its capacity to regulate expression of lysyl hydroxylase 2 (also known as procollagen lysine, 2-oxoglutarate 5-dioxygenase or Plod2) (44), and thereby the extent of collagen cross-linking. We confirmed the strong association of TIAR with Wisper using Western blotting to detect TIAR following Wisper pulldown (FIG. 5B). Then, we performed a RNA immunoprecipitation assay to validate Wisper-TIAR interaction (FIG. 5C). Real-time PCR following TIAR immunoprecipitation detected Wisper and Plod2 as TIAR bound-transcripts but not Wisp2. Importantly, Wisper knockdown reduced the amounts of TIAR associated-Wisper as expected, and in addition also affected the amounts of TIAR bound-Plod2 (FIG. 5C). Downregulation of Wisper expression in cardiac fibroblasts resulted therefore in decreased Plod2 expression whereas Wisp2 depletion did not change Plod2 concentrations (FIG. 5D). TIAR has been demonstrated to shuttle between the cytoplasm and the nucleus (45). Since Wisper was also found in both the cytoplasm and the nucleus, we investigated whether TIAR nuclear translocation could depend on Wisper action. Primary cardiac fibroblasts were therefore transfected with Wisper-targeting GapmeRs and TIAR subcellular localization was determined by immunostaining (FIG. 5E). Wisper knockdown resulted in a dose-dependent decrease in the number of fibroblasts with nuclear TIAR staining. Confocal microscopy confirmed the absence of TIAR in the nucleus and retention of the protein in the cytoplasm of treated cells.

Preventive Wisper Depletion In Vivo Inhibits Cardiac Fibrosis

To test if the anti-fibrotic effects of Wisper in cultured CFs may hold therapeutic potential in cardiac fibrosis, we performed loss of function experiments in mice. We first completed a dose escalation study in adult untouched mice by administering 5, 10 and 15 mg/kg of Wisper GapmeRs (FIG. S5A of (66)). Control mice received a scrambled GapmeR at a dose of 10 mg/kg. All mice injected with 15 mg kg died within the first week following GapmeR injection, whereas the 5 and 10 mg/kg doses had no impact on survival (FIG. S5B of (66)). Echocardiography performed at 4, 14, and 28 days post injection showed that mice receiving 10 mg/kg of Wisper GapmeRs demonstrated signs of cardiac remodeling, in particular a thickening of the interventricular septum. Animals injected with 5 mg/kg were not different from controls (FIG. S5C & Table S2 of (66)). To determine the impact of acute and massive Wisper depletion on cardiac dimensions and function, echocardiography was performed in untouched mice receiving 15 mg/kg Wisper GapmeR four days after injection. At this time point, the myocardium exhibited structural alterations, including an increased thickness of the ventricular septum and of the posterior wall, with a concomitant reduction of the left ventricular cavity. This peculiar situation was characterized by a paradoxical increase in ejection fraction, associated to a largely decreased stroke volume, creating a very detrimental situation. (FIG. S5D of (66)). Wisper was significantly depleted in isolated adult CFs ($P<0.007$), and a robust downregulation of key PCGs, including Col1a1, Col3a1, Vim and Postn was also observed (FIG. S5E-F of (66)). Finally, a significant upregulation of cardiac stress markers, including Ctgf and Myh7 ($P=0.012$ and 0.011 respectively), was measured. Interestingly, despite a dramatic decrease of collagen expression in the heart in animals receiving this toxic dose of Wisper GapmeRs, no effects on collagen expression were observed in the kidneys or the liver (FIG. S5G of (66)). Signs of liver damage were however evident since plasma concentrations of both aspartate aminotransferase (AST) and alanine aminotransferase (ALT) were elevated (FIG. S5H of (66)). Importantly, the amounts of these enzymes in the blood of mice receiving 5 mg/kg were not changed, indicating no toxic effects of Wisper GapmeR at this concentration. Based on these data the 5 mg/kg dose was therefore selected for subsequent experiments in vivo.

Figure 11:
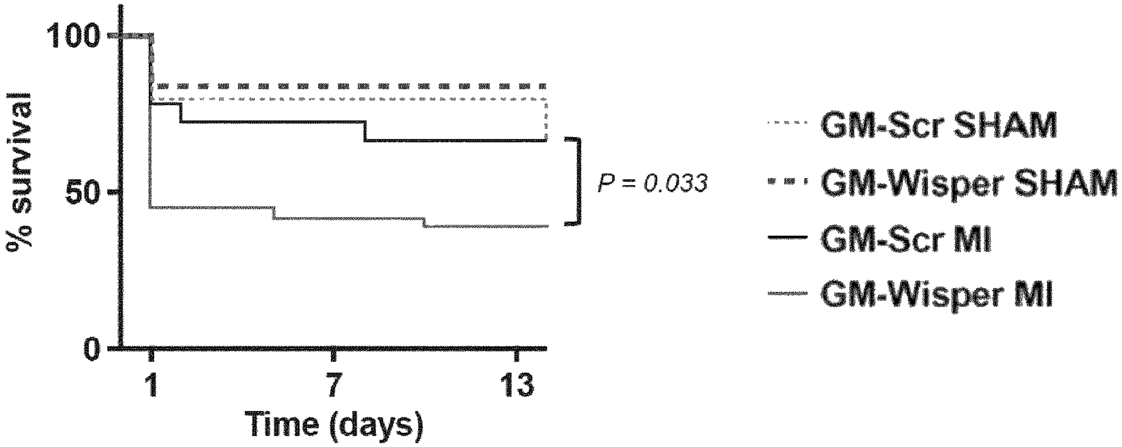
FIG. 11. Preventative Wisper depletion inhibits cardiac fibrosis and improves function. Survival after preventative GapmeR injection. P values calculated by Log-rank (Mantel-Cox) test vs. the GM-Scr MI group.

We used GapmeRs to perturb the induction of Wisper in a preventive strategy by delivering scrambled and Wisper-targeting GapmeRs 3 days prior to the induction of MI, and assessed cardiac function 7 and 14 days after MI (FIG. S6A of (66)). RNA was isolated and histological sections were generated 14 days post-infarction. Consistent with the observed effects in vitro, delivery of Wisper GapmeR resulted in the blunted expression of Wisper in the heart (FIG. S6B of (66)) and of key ECM-associated PCGs (FIG. S6C of (66)). Wisper was not affected by GapmeR treatment in sham-operated animals, suggesting that only stress-stimulated Wisper expression was sensitive to knockdown using a dose of 5 mg/kg. Importantly, gene expression was measured more than 2 weeks after GapmeR administration. Compared to scrambled GapmeR-treated animals, mice treated with Wisper GapmeR exhibited improved structural and functional parameters at 7 and 14 days post-MI as assessed by echocardiography (FIG. S6D and E as well as Table S3 of (66)). Wisper-depleted mice demonstrated decreased remodeling as indicated from decreased heart weight to tibial length ratio (FIG. S6F of (66)). Infarct size was reduced and a significant decrease in myocardial fibrosis was observed (FIG. S6G of (66); $P=0.006$). Considering the impact of Wisper depletion on CF proliferation in vitro, we also assessed non-myocyte cell proliferation in vivo via BrdU incorporation. The reduced numbers of BrdU-positive non-myocyte cells in Wisper GapmeR-treated animals were indicative of decreased proliferation in this subpopulation (FIG. S6H of (66)). However, despite these largely beneficial effects of Wisper depletion on maladaptive remodeling, decreased CF survival prior to injury may also be expected to affect the acute wound healing process. Indeed, we observed that Wisper GapmeR-treated mice exhibited a higher rate of mortality during the acute phase after MI, primarily resulting from left ventricular wall rupture, suggesting that Wisper silencing might impair the acute would healing process that relies on CF activity (FIG. 11). This prompted us to test the therapeutic potential of Wisper depletion in a therapeutic protocol more relevant for a clinical setting.

Figure 6B:
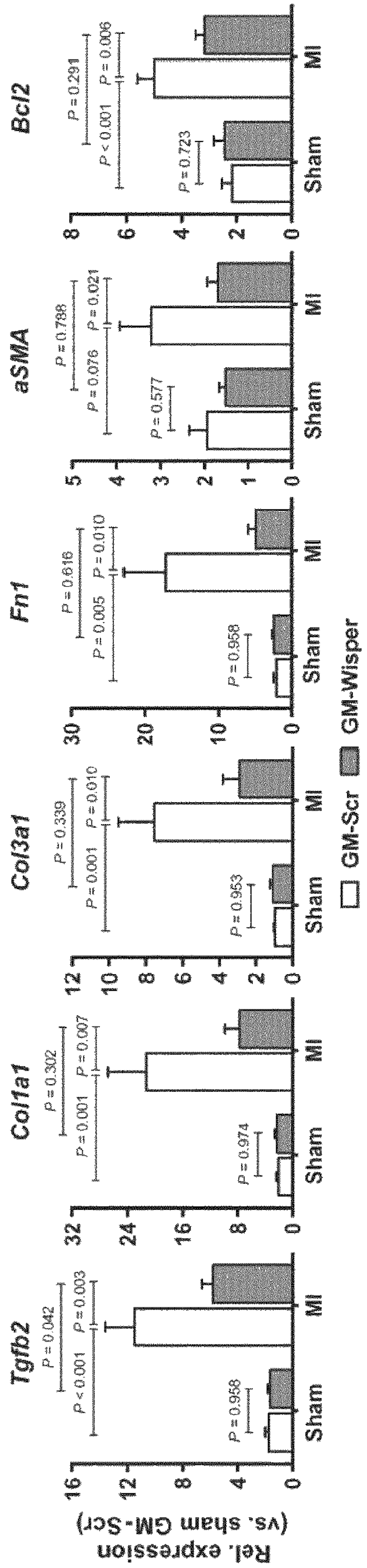
FIG. 6. Therapeutic depletion of Wisper inhibits cardiac fibrosis and improves function. (A and) Expression of Wisper (A) and fibrotic/stress genes (B) following GapmeR injection (GM-Scr: white; GM-Wisper: grey) in sham-operated and MI mice 28 days after surgery. Bars represent means normalized to sham GM-Scr±SEM. P values determined by two-way ANOVA (Fisher's test) (C) M mode images of the left ventricle of GapmeR-injected mice 28 days post-MI. (D) Echocardiographic assessment of cardiac dimension (diastolic left ventricular internal dimension, LVID d; diastolic intra ventricular septum, IVS d) and function (fractional shortening, FS %; ejection fraction, EF %). Graphs show means normalized to the average values of sham±SEM. P values determined by two-way ANOVA (Fisher's test). (E) Heart weight (HW) to tibial length (TL) ratio in GapmeR-injected sham and MI mice. P values determined by two-way ANOVA (Fisher's test). (F) Fibrotic tissue quantification by Masson's trichrome staining on heart sections. Graph shows the percentage of cardiac fibrosis as measured by ImageJ (n≥6). Bars represent means normalized to sham GM-Scr SEM. P values determined by two-way ANOVA (Fisher's test). (I) Effect of GapmeR injection on survival following myocardial infarction.
Figure 6A:
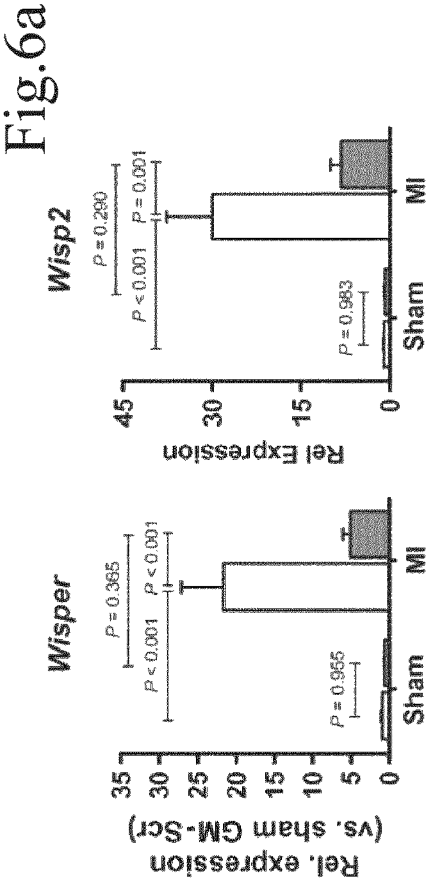
Figure 6C:
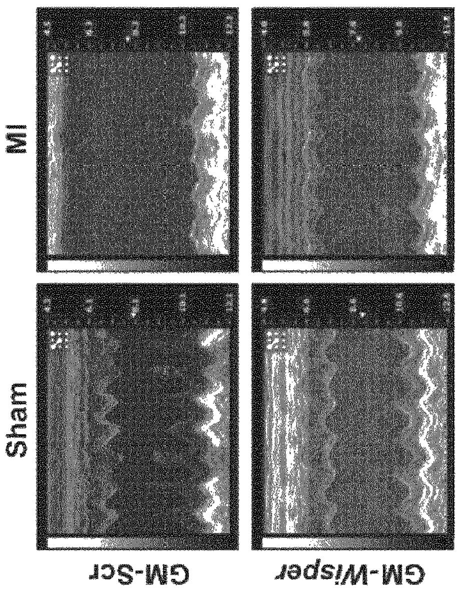
Figure 6D:
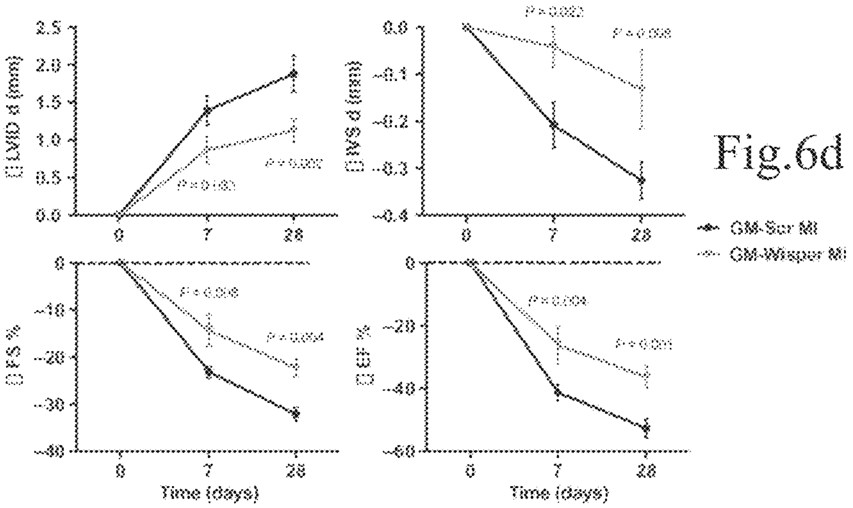
Figure 6F:
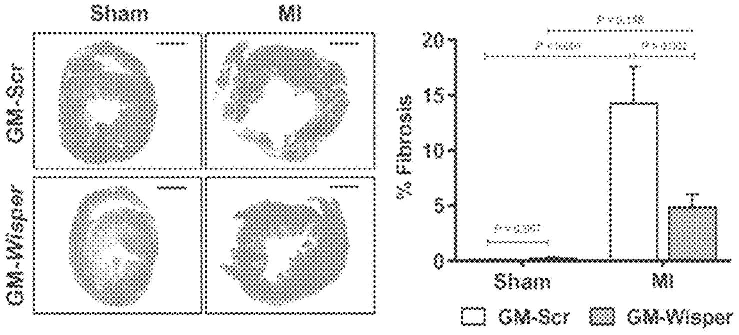
Figure 6E:
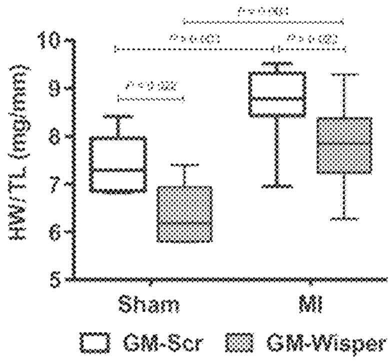
Figure 6G:
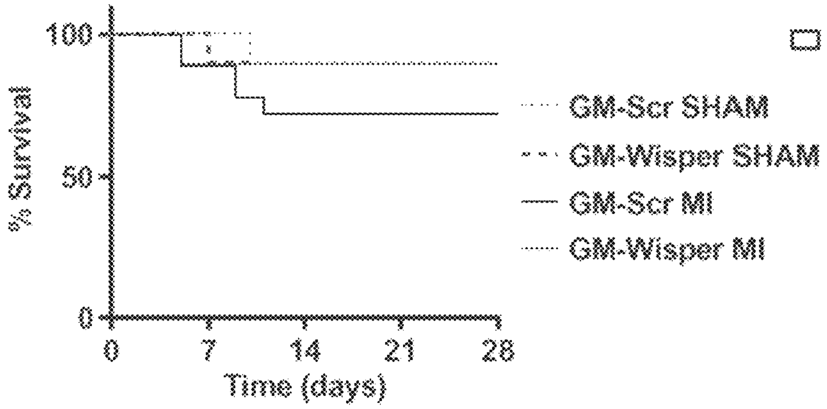

Therapeutic Depletion of Wisper In Vivo Inhibits Cardiac Fibrosis and Improves Function To evaluate the potential utility of Wisper targeting as an anti-fibrotic therapy, we utilized a therapeutic protocol in which Wisper was depleted after MI. MI was induced and Wisper GapmeRs were injected 2 and 9 days post-injury to avoid impacting acute wound healing but to subsequently modulate the evolution of the pathological proliferative phase of the remodeling process (FIG. 6A). Cardiac dimensions and function were assessed by echocardiography at 7 and 28 days post-MI. RNA was isolated upon sacrifice at 28 days, a temporal point coinciding with the evolution of the mature scar and the development of pathological remodeling. Both Wisper and its proximal PCG Wisp2 demonstrated blunted cardiac expression in Wisper GapmeR-treated mice (FIG. 6A). This profile was associated with significant impact on the expression of key ECM and pro-fibrotic PCGs including Tgfb2 ($P=0.003$), Col1a1 ($P=0.007$), Col3a1 ($P=0.010$), Fn1 ($P=0.010$) and $\alpha$-SMA ($P=0.021$) (FIG. 6B; FIG. S7A of (66)). Additionally, expression of cardiac stress markers was also blunted upon Wisper silencing suggestive of a beneficial impact on cardiac hypertrophy (FIG. S7A of (66)). At both 7 and 28 days post-MI, Wisper-depleted mice exhibited significantly improved cardiac function (FIG. 6E; % FS: $P=0.008$ and 0.004 at 7 and 28 days respectively), and decreased remodeling (FIG. 6C-E and Table S4 of (66)). This response was associated with a reduction in infarct size and a significant perturbation of cardiac fibrosis (FIG. 6F; $P=0.002$), resulting in preserved tissue architecture and reduced thinning of the myocardial wall after Wisper knockdown. In support of this, post infarction fibrosis was found highly correlated with Wisper expression in treated mice, even better correlated than with the expression of canonical ECM associated PCGs such as Col1a1 and Col3a1 ((66)). Importantly, mortality rate in treated animals was not augmented during the acute phase, indicating that the wound healing process was not negatively impacted (FIG. 6G). Wisper-depleted mice had a slightly increased survival rate post-injury when compared to controls, suggestive of an overall beneficial effect on mortality rates. Collectively these data support an important role for Wisper in pathological cardiac fibrosis and demonstrate that therapeutic targeting of Wisper after MI elicits clinically desirable effects.

Figure 7A:
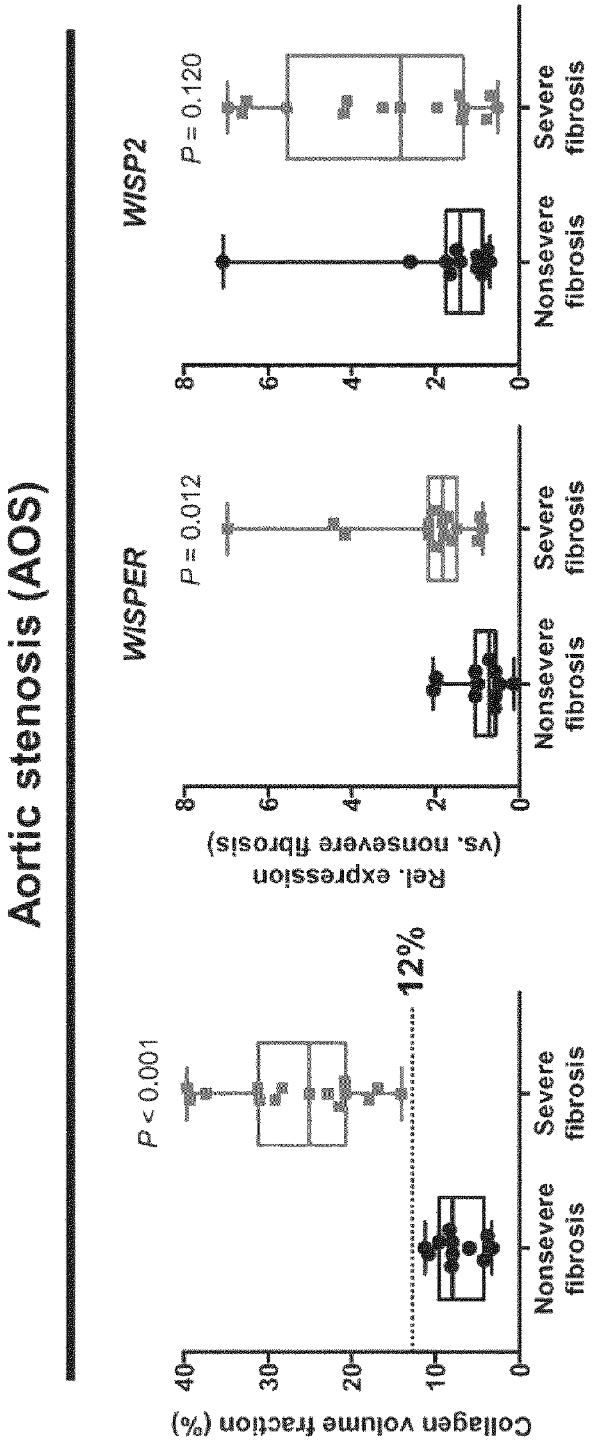
FIG. 7. WISPER, a functionally conserved human ortholog of mouse Wisper. (A) Box plots representation of the collagen volume fraction (CVF) in the heart of the non-severe (n=11) and severe fibrosis (n=15) groups of patients affected by aortic stenosis (AOS). The line indicates the CVF cut-off value used differentiate the two groups (12%). Box plots showing WISPER and WISP2 relative expression analyzed by qRT-PCR in cardiac biopsies from the two different fibrotic groups. Data show the mean, all the individual values and the minimal to maximal variation. P values determined by Student's t test (compared to non-severe fibrosis group). (B) Correlation analysis between the CVF and WISPER and WISP2 expression quantified by qRT-PCR. Pearson's correlation test (r; 95% CI). (C) Time course of WISPER and WISP2 expression in differentiating human cardiac fibroblasts (cardiac FBs; red) and dermal FBs (green). Graphs show means normalized to control±SEM (n=6 to 14). P values vs. control determined by one-way ANOVA. (D) Correlation analysis between WISPER expression and COLIA1, COL3A1, FN1 and αSMA expression in differentiating human cardiac fibroblasts. Spearman's correlation test (r; 95% CI). (E) Effect of GapmeR-induced WISPER depletion (25 nM, 48 h) on WISP2 and fibroblast gene expression in human cardiac fibroblasts. Bars show mean±SEM (n=3). P values determined by Student's t test. (F) Effect of GapmeR-induced WISPER depletion (25 nM, 48 h) on PLOD2 expression in human cardiac fibroblasts. Bars show mean±SEM (n=3). P values determined by Student's t test.
Figure 7B:
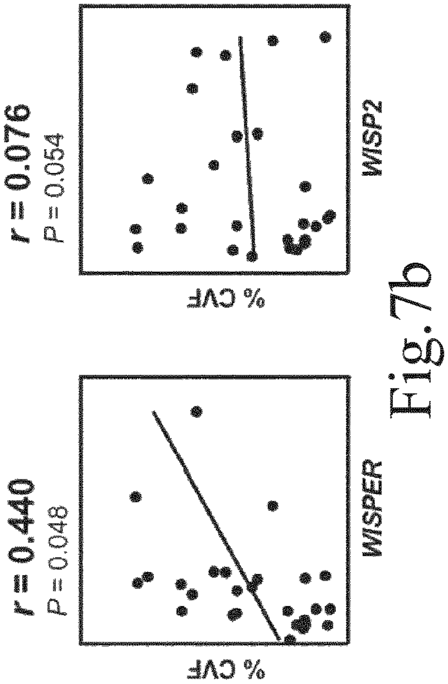
Figure 7C:
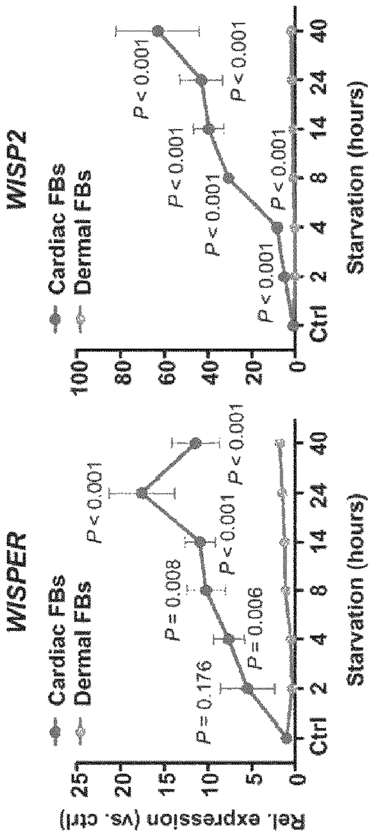
Figure 7E:
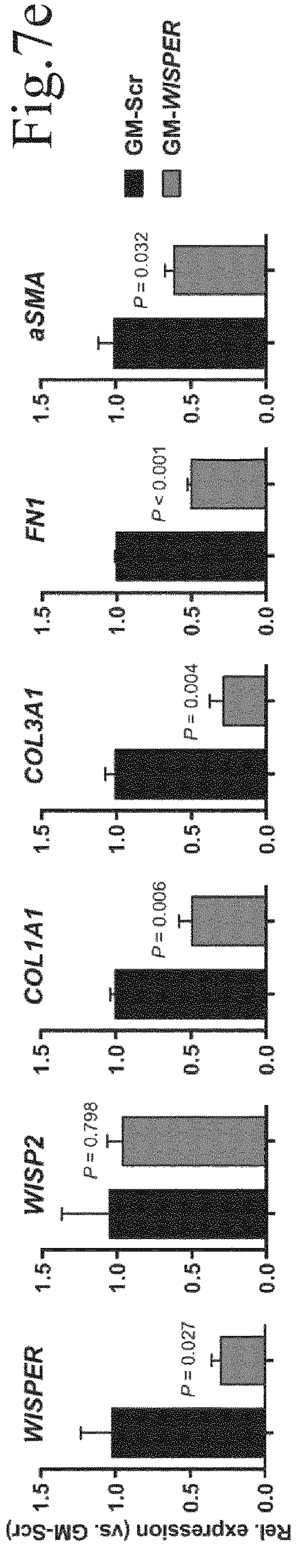
Figure 7D:
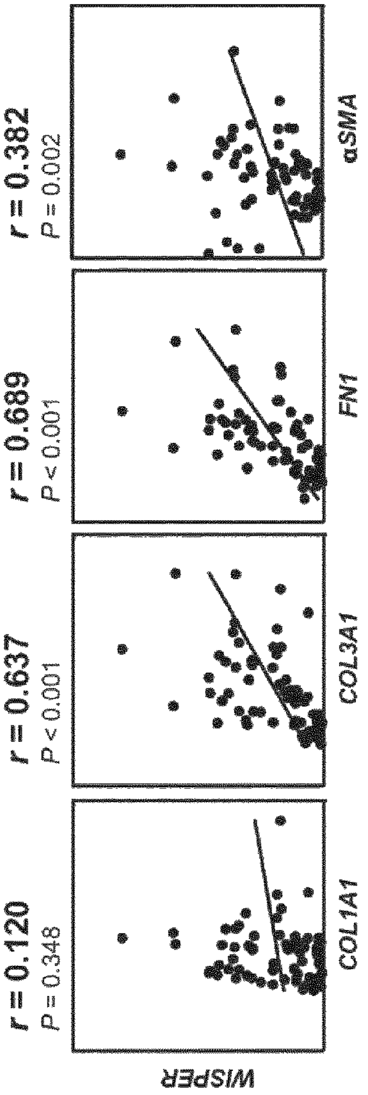
Figure 7F:
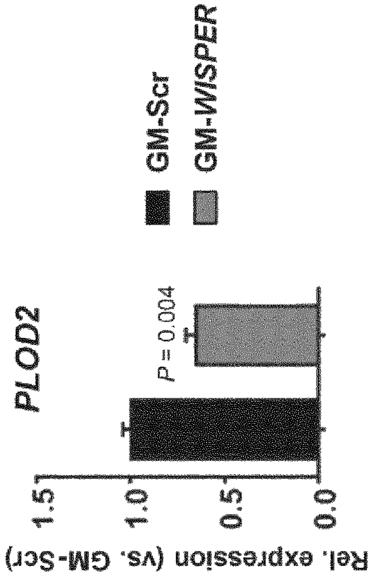
Figure 8B:
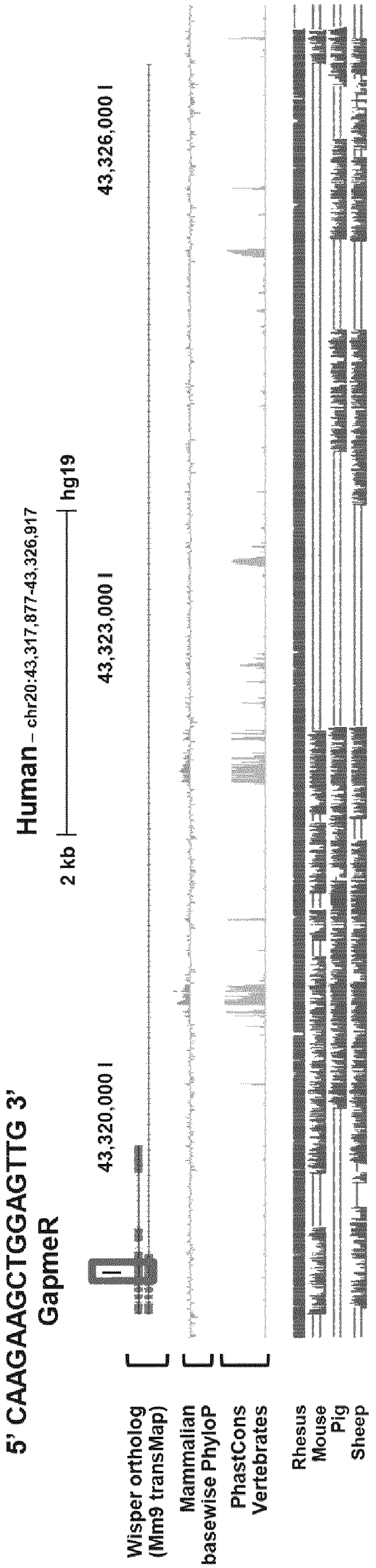

WISPER Expression Correlates with the Extent of Fibrosis in the Diseased Human Heart A putative ortholog of Wisper was identified in the human genome, mapping to a left ventricle-specific SE (FIG. 8 and (66)). Primers were designed to amplify this transcript, which could be consistently detected in RNA isolated from human cardiac biopsies, formally demonstrating that WISPER was evolutionary conserved. We therefore proceeded to quantify WISPER expression in RNA isolated from the interventricular septum of patients suffering from aortic stenosis (AOS). AOS is associated with extensive myocardial fibrosis that directly contributes to left ventricle dysfunction. In cardiac samples from all AOS patients, the collagen volume fraction (CVF) was higher than in samples from healthy volunteers (46). After analyzing the distribution of CVF in the AOS cohort, two groups were identified: a group with non-severe fibrosis (n=11) with a CVF lower than 12%, and a severe fibrosis group (n=15) with a CVF greater than 12%. Interestingly, WISPER expression, and not the expression of its proximal PCG WISP2, was significantly increased in the severe fibrosis group (FIG. 7A; P=0.012 and 0.120 respectively). Moreover, in a correlation analysis, WISPER expression and not WISP2 was found to be associated with the degree of CVF in all AOS patients (FIG. 7B). To evaluate the functional importance of WISPER in human fibroblasts, we used human dermal fibroblasts and human CFs. Both cell types can be induced to differentiate into myofibroblasts via serum starvation. This process is associated with the upregulation of COLIA1, COL3A1 and αSMA in both fibroblast populations (66). Interestingly, WISPER was significantly induced by serum starvation in CFs but not in dermal fibroblasts (FIG. 7C; P<0.001). WISP2 was also upregulated in differentiating CFs. Supporting observations in the mouse, WISPER expression was correlated with COL3A1, FN1 and αSMA expression in differentiating human CFs (FIG. 7D). The functional importance of WISPER was tested in knockdown experiments. WISPER depletion using GapmeRs resulted in decreased expression of COL1A1, COL3A1, FN1 and αSMA in human CFs (FIG. 7E). Silencing of WISPER did not impact WISP2 expression, suggesting again that WISPER controls fibrotic gene expression independently of WISP2. Finally, PLOD2 expression was decreased in human CFs following GapmeR-mediated WISPER depletion (FIG. 7F). These findings demonstrate that WISPER is an lncRNA conserved in human, and highlight the translational relevance of WISPER as a therapeutic target in cardiac fibrosis.

TABLE 1

| Sequences | | SEQ ID No. |
|---|---|---|
| Human Proximal Wisper-Enhancer | hg38_dna range = chr20: 44691595-44696953 5'pad = 0 3'pad = 0 strand = + | 1 |
| Human Wisper Proximal Promoter | hg19_dna range = chr20: 43324240-43329987 5'pad = 0 3'pad = 0 strand = + | 2 |
| Human WISPER Super-enhancer | hg19_dna range = chr20: 43318059-43342644 5'pad = 0 3'pad = 0 strand = + | 3 |
| Human WISPER Downstream cis-sequences | hg19_dna range = chr20: 43283796-43318224 5'pad = 0 3'pad = 0 strand = + | 4 |
| SMAD7-cis-regulatory | lncRNA XLOC_015277 hg19_dna range = chr18: 46477041-46490607 5'pad = 0 3'pad = 0 strand = + | 5 |
| CYR61 cis-regulatory | hg19_dna range = chr1: 86071896-86085046 5'pad = 0 3'pad = 0 strand = + | 6 |
| COL15A1 cis-regulatory | XLOC_022236 hg19_dna range = chr9: 101700203-101712895 5'pad = 0 3'pad = 0 strand = + | 7 |
| SPARC cis-regulatory | XLOC_004910 hg19_dna range = chr5: 151000095-151012897 5'pad = 0 3'pad = 0 strand = + | 8 |

TABLE 2

| | Fibrosis Group | |
|---|---|---|
| | Non Severe | Severe |
| n | 11 | 15 |
| CVF(Avg.) | 7.40 | 26.38 |
| Age(Avg.) | 71 | 71.47 |
| Gender | 10 Females; 1 Males | 8 Females; 7 Males |
| Hypertension | 8 Yes; 3 No | 11 |
| Atrial fibrillation | 2 Yes; 9 No | 8 Yes; 7 No |
| BMI(Avg.) | 28.95 | 28.61 |
| SBP (Avg.) (mmHg) | 121.82 | 118.53 |
| DBP (Avg.) (mmHg) | 71.09 | 67.67 |
| HR (Avg.)(beats/min) | 72.09 | 77.47 |
| LVMI(Avg.) | 125.57 | 155.15 |
| LVH | 5 Yes; 6 No | 9 Yes; 6 No |
| RWT(Avg.) | 0.62 | 0.62 |
| AVAi(Avg.) | 0.32 | 0.39 |
| LVEDD(Avg.) | 4.14 | 4.66 |
| LVESD(Avg.) | 2.29 | 3.11 |
| LVEF(Avg.) | 75.44 | 60.72 |
| DT(Avg.) | 290.91 | 269.13 |
| IVRT(Avg.) | 84.00 | 119.13 |

BMI, body mass index; SBP, systolic blood pressure DBP, diastolic blood pressure HR, heart rate; LVMI, left ventricular mass index (g/m2) LVH, LV hypertrophy; RWT, relative wall thickness AVAi, aortic valve area index LVEDD, LV end-diastolic diameter LVESD, LV end-systolic diameter; LVEF, left ventricular ejection fraction DT, deceleration time; IVRT, isovolumic relaxation time.

TABLE 3

| GapmeRs Sequences | | | | |
|---|---|---|---|---|
| Species | GeneName | Sequence (5'-3') | Supplier | SEQ ID No. |
| both | Negative CTRLA | AACACGTCTATACGC | Exiqon | 9 |
| mouse | Mm_Wisper | AGGTGTGCGATAGAG | Exiqon | 10 |
| mouse | Mm_Wisp2 | CGCAAGTGCCAAGAGT | Exiqon | 11 |
| human | Hu_WISPER | CAAGAAGCTGGAGTTG | Exiqon | 12 |
| human | Hu_WISPER_2 | AGGTGTGCGA TAGAG | Exiqon | 14 |

REFERENCES

1. S. D. Prabhu, N. G. Frangogiannis, The Biological Basis for Cardiac Repair After Myocardial Infarction: From Inflammation to Fibrosis. *Circ Res* 119, 91-112 (2016).
2. N. G. Frangogiannis, Pathophysiology of Myocardial Infarction. *Compr Physiol* 5, 1841-1875 (2015).
3. M. Writing Group, D. Mozaffarian, E. J. Benjamin, A. S. Go, D. K. Arnett, M. J. Blaha, M. Cushman, S. R. Das, S. de Ferranti, J. P. Despres, H. J. Fullerton, V. J. Howard, M. D. Huffman, C. R. Isasi, M. C. Jimenez, S. E. Judd, B. M. Kissela, J. H. Lichtman, L. D. Lisabeth, S. Liu, R. H. Mackey, D. J. Magid, D. K. McGuire, E. R. Mohler, 3rd, C. S. Moy, P. Muntner, M. E. Mussolino, K. Nasir, R. W. Neumar, G. Nichol, L. Palaniappan, D. K. Pandey, M. J. Reeves, C. J. Rodriguez, W. Rosamond, P. D. Sorlie, J. Stein, A. Towfighi, T. N. Turan, S. S. Virani, D. Woo, R. W. Yeh, M. B. Turner, C. American Heart Association Statistics, S. Stroke Statistics, Heart Disease and Stroke Statistics-2016 Update: A Report From the American Heart Association. *Circulation* 133, e38-60 (2016).
4. F. G. Spinale, M. R. Zile, Integrating the myocardial matrix into heart failure recognition and management. *Circ Res* 113, 725-738 (2013).
5. E. B. Schelbert, G. C. Fonarow, R. O. Bonow, J. Butler, M. Gheorghiade, Therapeutic targets in heart failure: refocusing on the myocardial interstitium. *J Am Coll Cardiol* 63, 2188-2198 (2014).
6. K. T. Weber, Y. Sun, S. K. Bhattacharya, R. A. Ahokas, I. C. Gerling, Myofibroblast-mediated mechanisms of pathological remodelling of the heart. *Nat Rev Cardiol* 10, 15-26 (2013).
7. J. K. Lighthouse, E. M. Small, Transcriptional control of cardiac fibroblast plasticity. *J Mol Cell Cardiol* 91, 52-60 (2016).
8. K. B. Schuetze, T. A. McKinsey, C. S. Long, Targeting cardiac fibroblasts to treat fibrosis of the heart: focus on HDACs. *J Mol Cell Cardiol* 70, 100-107 (2014).
10. S. Ounzain, T. Pedrazzini, Super-enhancer lncs to cardiovascular development and disease. *Biochim Biophys Acta* 1863, 1953-1960 (2016).
11. J. A. Wamstad, X. Wang, O. O. Demuren, L. A. Boyer, Distal enhancers: new insights into heart development and disease. *Trends Cell Biol* 24, 294-302 (2014).
12. D. Hnisz, B. J. Abraham, T. I. Lee, A. Lau, V. Saint-Andre, A. A. Sigova, H. A. Hoke, R. A. Young, Super-enhancers in the control of cell identity and disease. *Cell* 155, 934-947 (2013).
13. W. A. Whyte, D. A. Orlando, D. Hnisz, B. J. Abraham, C. Y. Lin, M. H. Kagey, P. B. Rahl, T. I. Lee, R. A. Young, Master transcription factors and mediator establish super-enhancers at key cell identity genes. *Cell* 153, 307-319 (2013).
15. K. V. Morris, J. S. Mattick, The rise of regulatory RNA. *Nat Rev Genet* 15, 423-437 (2014).
18. R. A. Boon, S. Dimmeler, MicroRNAs in myocardial infarction. *Nat Rev* Cardiol 12, 135-142 (2015).
22. K. Wang, F. Liu, L. Y. Zhou, B. Long, S. M. Yuan, Y. Wang, C. Y. Liu, T. Sun, X. J. Zhang, P. F. Li, The long noncoding RNA CHRF regulates cardiac hypertrophy by targeting miR-489. *Circ Res* 114, 1377-1388 (2014).
23. M. T. Piccoli, C. Bar, T. Thum, Non-coding RNAs as modulators of the cardiac fibroblast phenotype. *J Mol Cell Cardiol* 92, 75-81 (2016).
24. T. R. Mercer, J. S. Mattick, Structure and function of long noncoding RNAs in epigenetic regulation. *Nat Struct Mol Biol* 20, 300-307 (2013).
25. W. Li, D. Notani, M. G. Rosenfeld, Enhancers as non-coding RNA transcription units: recent insights and future perspectives. *Nat Rev Genet* 17, 207-223 (2016).
26. A. A. Sigova, A. C. Mullen, B. Molinie, S. Gupta, D. A. Orlando, M. G. Guenther, A. E. Almada, C. Lin, P. A. Sharp, C. C. Giallourakis, R. A. Young, Divergent transcription of long noncoding RNA/mRNA gene pairs in embryonic stem cells. *Proc Natl Acad Sci USA* 110, 2876-2881 (2013).
27. A. A. Sigova, B. J. Abraham, X. Ji, B. Molinie, N. M. Hannett, Y. E. Guo, M. Jangi, C. C. Giallourakis, P. A. Sharp, R. A. Young, Transcription factor trapping by RNA in gene regulatory elements. *Science* 350, 978-981 (2015).
28. M. Mele, J. L. Rinn, "Cat's Cradling" the 3D Genome by the Act of LncRNA Transcription. *Mol Cell* 62, 657-664 (2016).
29. S. Ounzain, R. Micheletti, T. Beckmann, B. Schroen, M. Alexanian, I. Pezzuto, S. Crippa, M. Nemir, A. Sarre, R. Johnson, J. Dauvillier, F. Burdet, M. Ibberson, R. Guigo, I. Xenarios, S. Heymans, T. Pedrazzini, Genome-wide profiling of the cardiac transcriptome after myocardial infarction identifies novel heart-specific long non-coding RNAs. *Eur Heart J* 36, 353-368 (2015).
31. D. Jeong, M. A. Lee, Y. Li, D. K. Yang, C. Kho, J. G. Oh, G. Hong, A. Lee, M. H. Song, T. J. LaRocca, J. Chen, L. Liang, S. Mitsuyama, V. D'Escamard, J. C. Kovacic, T. H. Kwak, R. J. Hajjar, W. J. Park, Matricellular Protein CCN5 Reverses Established Cardiac Fibrosis. *J Am Coll Cardiol* 67, 1556-1568 (2016).
32. S. Pott, J. D. Lieb, What are super-enhancers? *Nat Genet* 47, 8-12 (2015).
33. T. Okubo, B. L. Hogan, Hyperactive Wnt signaling changes the developmental potential of embryonic lung endoderm. *J Biol* 3, 11 (2004).

34. N. G. Frangogiannis, The inflammatory response in myocardial injury, repair, and remodelling. *Nat Rev* Cardiol 11, 255-265 (2014).
35. P. Wiesel, L. Mazzolai, J. Nussberger, T. Pedrazzini, Two-kidney, one clip and one-kidney, one clip hypertension in mice. *Hypertension* 29, 1025-1030 (1997).
36. S. Konermann, M. D. Brigham, A. E. Trevino, J. Joung, O. O. Abudayyeh, C. Barcena, P. D. Hsu, N. Habib, J. S. Gootenberg, H. Nishimasu, O. Nureki, F. Zhang, Genome-scale transcriptional activation by an engineered CRISPR-Cas9 complex. *Nature* 517, 583-588 (2015).
37. F. Yang, F. Yi, X. Han, Q. Du, Z. Liang, MALAT-1 interacts with hnRNP C in cell cycle regulation. *FEBS Lett* 587, 3175-3181 (2013).
38. E. Hacisuleyman, L. A. Goff, C. Trapnell, A. Williams, J. Henao-Mejia, L. Sun, P. McClanahan, D. G. Hendrickson, M. Sauvageau, D. R. Kelley, M. Morse, J. Engreitz, E. S. Lander, M. Guttman, H. F. Lodish, R. Flavell, A. Raj, J. L. Rinn, Topological organization of multichromosomal regions by the long intergenic noncoding RNA Firre. *Nat Struct Mol Biol* 21, 198-206 (2014).
39. C. Le Guiner, F. Lejeune, D. Galiana, L. Kister, R. Breathnach, J. Stevenin, F. Del Gatto-Konczak, TIA-1 and TIAR activate splicing of alternative exons with weak 5' splice sites followed by a U-rich stretch on their own pre-mRNAs. *J Biol Chem* 276, 40638-40646 (2001).
40. S. Waris, M. C. Wilce, J. A. Wilce, RNA recognition and stress granule formation by TIA proteins. *Int J Mol Sci* 15, 23377-23388 (2014).
41. L. Y. Tan, P. Whitfield, M. Llorian, E. Monzon-Casanova, M. D. Diaz-Munoz, M. Turner, C. W. Smith, Generation of functionally distinct isoforms of PTBP3 by alternative splicing and translation initiation. *Nucleic Acids Res* 43, 5586-5600 (2015).
42. Y. Blech-Hermoni, S. J. Stillwagon, A. N. Ladd, Diversity and conservation of CELF1 and CELF2 RNA and protein expression patterns during embryonic development. *Dev Dyn* 242, 767-777 (2013).
43. G. Haas, S. Cetin, M. Messmer, B. Chane-Woon-Ming, O. Terenzi, J. Chicher, L. Kuhn, P. Hammann, S. Pfeffer, Identification of factors involved in target RNA-directed microRNA degradation. *Nucleic Acids Res* 44, 2873-2887 (2016).
44. H. N. Yeowell, L. C. Walker, D. M. Mauger, P. Seth, M. A. Garcia-Blanco, TIA nuclear proteins regulate the alternate splicing of lysyl hydroxylase 2. *J Invest Dermatol* 129, 1402-1411 (2009).
45. T. Zhang, N. Delestienne, G. Huez, V. Kruys, C. Gueydan, Identification of the sequence determinants mediating the nucleo-cytoplasmic shuttling of TIAR and TIA-1 RNA-binding proteins. *J Cell Sci* 118, 5453-5463 (2005).
46. J. Beaumont, B. Lopez, N. Hermida, B. Schroen, G. San Jose, S. Heymans, F. Valencia, J. J. Gomez-Doblas, E. De Teresa, J. Diez, A. Gonzalez, microRNA-122 down-regulation may play a role in severe myocardial fibrosis in human aortic stenosis through TGF-beta1 up-regulation. *Clin Sci* (*Lond*) 126, 497-506 (2014).
47. G. Rizki, L. A. Boyer, Lncing Epigenetic Control of Transcription to Cardiovascular Development and Disease. *Circ Res* 117, 192-206 (2015).
49. C. Sanchez-Jimenez, J. M. Izquierdo, T-cell intracellular antigens in health and disease. *Cell Cycle* 14, 2033-2043 (2015).
50. J. Wu, D. P. Reinhardt, C. Batmunkh, W. Lindenmaier, R. K. Far, H. Notbohm, N. Hunzelmann, J. Brinckmann, Functional diversity of lysyl hydroxylase 2 in collagen synthesis of human dermal fibroblasts. *Exp Cell Res* 312, 3485-3494 (2006).
51. Z. Wang, M. Kayikci, M. Briese, K. Zarnack, N. M. Luscombe, G. Rot, B. Zupan, T. Curk, J. Ule, iCLIP predicts the dual splicing effects of TIA-RNA interactions. *PLoS Biol* 8, e1000530 (2010).
52. L. Liu, H. Yue, Q. Liu, J. Yuan, J. Li, G. Wei, X. Chen, Y. Lu, M. Guo, J. Luo, R. Chen, LncRNA MT1JP functions as a tumor suppressor by interacting with TIAR to modulate the p53 pathway. *Oncotarget* 7, 15787-15800 (2016).
53. C. Sanchez-Jimenez, J. M. Izquierdo, T-cell intracellular antigen (TIA)-proteins deficiency in murine embryonic fibroblasts alters cell cycle progression and induces autophagy. *PLoS One* 8, e75127 (2013).
55. R. Kumarswamy, C. Bauters, I. Volkmann, F. Maury, J. Fetisch, A. Holzmann, G. Lemesle, P. de Groote, F. Pinet, T. Thum, Circulating long noncoding RNA, LIPCAR, predicts survival in patients with heart failure. *Circ Res* 114, 1569-1575 (2014).
56. B. E. Bernstein, J. A. Stamatoyannopoulos, J. F. Costello, B. Ren, A. Milosavljevic, A. Meissner, M. Kellis, M. A. Marra, A. L. Beaudet, J. R. Ecker, P. J. Farnham, M. Hirst, E. S. Lander, T. S. Mikkelsen, J. A. Thomson, The NIH Roadmap Epigenomics Mapping Consortium. *Nat Biotechnol*28, 1045-1048 (2010).
57. L. H. Michael, M. L. Entman, C. J. Hartley, K. A. Youker, J. Zhu, S. R. Hall, H. K. Hawkins, K. Berens, C. M. Ballantyne, Myocardial ischemia and reperfusion: a murine model. *Am J Physiol* 269, H2147-2154 (1995).
58. B. Lopez, R. Querejeta, A. Gonzalez, M. Larman, J. Diez, Collagen cross-linking but not collagen amount associates with elevated filling pressures in hypertensive patients with stage C heart failure: potential role of lysyl oxidase. *Hypertension* 60, 677-683 (2012).
59. A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner. *Bioinformatics* 29, 15-21 (2013).
60. S. Anders, P. T. Pyl, W. Huber, HTSeq—a Python framework to work with high-throughput sequencing data. *Bioinformatics* 31, 166-169 (2015).
61. L. Wang, S. Wang, W. Li, RSeQC: quality control of RNA-seq experiments. *Bioinformatics* 28, 2184-2185 (2012).
62. B. Li, C. N. Dewey, RSEM: accurate transcript quantification from RNA-Seq data with or without a reference genome. *BMC Bioinformatics* 12, 323 (2011).
63. M. D. Robinson, D. J. McCarthy, G. K. Smyth, edgeR: a Bioconductor package for differential expression analysis of digital gene expression data. *Bioinformatics* 26, 139-140 (2010).
64. M. E. Ritchie, B. Phipson, D. Wu, Y. Hu, C. W. Law, W. Shi, G. K. Smyth, limma powers differential expression analyses for RNA-sequencing and microarray studies. *Nucleic Acids Res* 43, e47 (2015).
65. Y. Benjamini, Y. Hochberg, Controlling the false discovery rate: a practical and powerful approach to multiple testing. *Journal of the Royal Statistical Society* Series B 57, 289-300 (1995).
66. Micheletti R, Plaisance I, Abraham B J, Sarre A, Ting C C, Alexanian M, Maric D, Maison D, Nemir M, Young R A, Schroen B, González A, Ounzain S, Pedrazzini T. The long noncoding RNA Wisper controls cardiac fibrosis and remodeling Sci Transl Med. 2017 Jun. 21; 9(395).
67. Dominguez A A, Lim W A, and Qi L S. Beyond editing: repurposing CRISPR-Cas9 for precision genome regulation and interrogation. Nat Rev Mol Cell Biol. 2016 January; 17(1):5-15.
68. Andriy Didovyk, Bartlomiej Borek, Lev Tsimring, and Jeff Hasty. Curr Opin Biotechnol. 2016 August; 40: 177-184.

The invention claimed is:

1. An antisense oligonucleotide targeting a regulatory sequence of one or more lncRNA associated with cardiac-specific super enhancers (SEs), wherein the antisense oligonucleotide comprises a sequence of SEQ ID NO: 12 or SEQ ID NO: 14.

2. A cell or population of cells comprising the antisense oligonucleotide of claim 1.

3. A pharmaceutical composition comprising the antisense oligonucleotide of claim 1 and one or more pharmaceutically acceptable excipient or carrier.

4. A method of treating a cardiac disease, the method comprising administering the pharmaceutical composition of claim 3 to a subject in need thereof.

5. The method of claim 4, wherein the cardiac disease is cardiac fibrosis.

* * * * *

SEQUENCE LISTING

<160> NUMBER OF SEQ ID NOS: 14

<210> SEQ ID NO 1
<211> LENGTH: 5359
<212> TYPE: DNA
<213> ORGANISM: Homo sapiens

<400> SEQUENCE: 1

```
gtcccctacc ccatgattca aagcagaaat tcgcaaagac tttgatgtag gctgggctgg     60
gagttgacta cacttgcatg cctgttgctt ggcaggatgg ctttcaaaaa agaaaaaaat    120
ataataatga aagattgaaa acagattatt ggggagaaaa gtatcccagg cgctagacgg    180
ctgtctctgc agcctctggc tcctgtccca cccattcccc ggccctgacg caaggctggc    240
tggaagaagg tgttctcgag attgttcagg ctgagggcct gactggcagg agactgaagc    300
ctaccccatt cctgcctggg tgccaagctc tgcatgaggt ttaaatatac ccacagcctg    360
acactatgcc ctagatcatg ctaaatgttt ccatactcct tgaattctct tctcaaggtt    420
catttattgt ccccattttt cagatcagta aactgaggcc cagagaggtt aactggtttg    480
cccacagtca cacagccaga caagtttgag tatgtctgat tctattgcct tattccaggt    540
ttgggataca ggcagagtag ggagaggttt aggatggtaa agaagaatgt tccaggagga    600
acagagttag tgtaagggca gtctaatcta gagtcagaat ttggagctgt ttgttacagc    660
agcatgacct agcctatcct gactgataca aatcatggta aactaattta tatgtcctga    720
aaaatattag aacttagcat ctacctctta ggagagcttt ttttttttt tttaactttt    780
acattttggc aaaacacacc gaacataaaa tttaccatct aagcaatttt aaatgtacaa    840
tgcatggctt taagtacatt cacattattg agtttctatc accatccttc cacagaactc    900
gtcatcttgc aaaactgaaa ttctaaaccc attaaggaaa cttctcattt ccccctcccc    960
agcccctggc aattccactt tctgtctcta tgaattggac tacttttgac agatacctcc   1020
tataaatgga atcacacagt atgcatcttt ctgtgactga tttatttcac ttagcataat   1080
gtcctcaagc ttcatccctg ttgtagcatg tatcagaatt gccttccttt tttaaggctg   1140
aaaatcttcc attgtgtgga tacactatat tttgcttatc cactaatcta tcaatggaca   1200
cttgagtgcc tttcaccttt tggctattgt gaataatctg ctatgaacat ggacacacga   1260
atatcagagg cagccttttc aagcaaaggg tttttgggga aaaagccact gtccaggact   1320
ctaggcttgg ccactaactt gctgtgtagc tgtgggcaca ttgcttcctg catcgtgtat   1380
ggcaattcta actctctcca ccttcactgc ctactcacag ccgtgtgctg gggaccagat   1440
tagaccatgg actatgaaac tctcagcaaa gaaaaagcca cgaggggctg ttattgttat   1500
tactcagtgg ggtcagggca gtggcttccc aaaggcatga gtcactcatg gtggaattcc   1560
agacatcagg agggccgttc tgggcagcag agcccagatt ccagacagag cagtgaccct   1620
gacccggagc ccctagggga gccacaccct ttctctttgg ccactggctg ctgtgaggaa   1680
ggagtcagtg aatgtcataa tcatatgggc acttagggtg agagcctcca gtcccactgc   1740
ctcacgtaac tatttaagga ggctcagaaa gggtcatgca cttgcccaga gtcacacagc   1800
tagacagtgg tggaagctgg cctgggtcag atttggacat ctacagaagc ccttctcctc   1860
cctgctcgca cccctcttag ccccagcatg tgaggaaggc agctgtctcc ctgagctccg   1920
tccttctatg ccttgggttt agccatgttg actgctgtaa caaataactc caaaacctca   1980
gtggctttgc attataaatg cttggttctt tctcacatca aactgcaata agtcttgaca   2040
ggagggctct gttttctgca ggtcatatag ggattgagac ttttcctatt tgtggctttc   2100
```

ctcattctca gagtcctctc cattcagcag gcagatggca gaaagattgt gggtagaaga 2160
tttttataag ccagacctga aatcagtaca attatttttg cttacatccc attggccaga 2220
gctcagtcac atgaccacat ctaactgcaa agaaggctgg gaaatgtatc ccacatgtgt 2280
gcccaggaag aagaagatgg ctattggtga gccttggtag tcttccacaa gaacatgacc 2340
cagttctggc caataaaaca taaagaaagt atgctgggac aggaggtttg agaagggctg 2400
gcctcaatta ttatataaaa aggggtgtgg ggaaggtccc ctattctttc cctttaagtg 2460
gttgcatgag gatgcgatgt ctggaacttt ggcagccatg ttgagagcat gacgggccaa 2520
gcctcagggc tacagccaat atactgaggg tgctgaagcc aaaatgcggg tcctagatga 2580
catcactgaa cctctgaatg aaccaaaact ggagccacgt aacctccaga tttcttgact 2640
gcgaaggcac ctattattga attcaggagt aatagggtat tctattactt gcagcctaaa 2700
acatcctagc tgattgacac tcaggtgcaa atgctgaaaa cagctaagag gacaaggtta 2760
agccatgcca gctgttacaa cgaataactc caaaacctca gtggctttgc actacaaata 2820
cttggttccc ttgaaacccc tcctctgctt gaagttaggt agagccaagt aacatagctt 2880
tggcctactc tggatgttgt gctttttttgg ggaagttggg gacagagcag cagttcaagc 2940
acaaaatgac ctggctgctt tgtgccaggt cctttataca cacagtgtat acacgggagc 3000
aaaatgcctg gactcaaatc ttgagtctgc cacctcacca gccatgtgac cttgggcaaa 3060
gtcaatcaac ctcactgagc cctagtttcc ccattgaaaa cattggggtg attataaata 3120
ttctacccac agagtaaagg attaaatgtc caattcagat aaagaacttg gcacattatc 3180
tgtaaataaa cacttaaaag attctgacca gagcctggtg ggatgtgagt aatatcaacc 3240
ccaccttaga gatggggagt ctagggttca aggaaatgaa gtccaaggac atataaataa 3300
taagagacag agcctggatt ttaatacaga cctaattgaa cacctgctat gtgccaggca 3360
ttgtgtgagg tgtttagata tattatccca ttgaacatac tagcaatcct gcatgggagg 3420
tattattatt atcattattg ttattcctat tggacaaatg agaaagccaa aactcagaga 3480
agtgaaaaga cttgcctaca ggccaggtca agatgcagta cttgaaccta ggctgagtcc 3540
aagcctttat tctttccacc atgtataagc ctccctaaca gaagcccacc agactattat 3600
agtggaattg taggcatcag aggagtaata catttggctc ccatggctat tcagggttcc 3660
ctgaagtcat ccccaaaagc tggctgccag tccagcctgt caccaaggtt gtcctggtga 3720
tggctttacc ctcactcctc cagtagaata actgggccct ggagtggatg gtcctgaggg 3780
aggaagtttg gctcacttga taaagcagaa ctttcaaaca ctttgagctc atccatgatg 3840
gaataggctg ccttgggatg cgatgagttc tgtggtcctg ggaggataca agcagagaaa 3900
gtctggtggc cacctgcaag gaagattatt aagacagtta ctgcatagaa agtgaaatta 3960
gattcaaaga cctttcaggt ttgaaatctg tggttgcaag attctcaggt cccattttct 4020
cagattccag tctaagatta catgatactc aaaatccagg aatctaaggc tgcacgagtt 4080
ttctccttgg atttttttgtt ccctatttag gcagttagac tgcagaacat ctactgactc 4140
aggaaacaga tgtgttagta aaagcagaga atacatttct gggtttcaaa aacacccctt 4200
cctcccagga aagaacattc ctaagagact tgggcatctt gaacacctaa tgaatctgaa 4260
agaggctctc actttctgtg actgtcttta gggactgtcc acaaatactc tgtttctttt 4320
ccttttaggg tgccttagtc tgttcaggct gctacagcaa aacatcttag actgggtaat 4380
ttataaacaa cagaaattca ttgctcacag ttctggaggt tgggaaattc aagatcaagg 4440

```
ctccagcaga ctcagtgtct ggtgggagcc tgtttcttat agatggtgac ttctgtgtgt   4500

cctcacatgg cagaagggac agatgggctc cctcaagcct cttttacaag aacactaatc   4560

ccattcatgg gtggagccct cctgacctaa tcaacttcca aaggccccac ctcttaaggc   4620

tatcactgtg ggattaggt ctcaacatct gaactttggg gaacacattc agaccacagc    4680

acaggcccat agtaggattt ccacttgaac tccctcctct gcttgaagtt aggtacagcc   4740

aagtaacaag ctttggccaa tgaaatgtgt gcagaagtga agtgtgccac ttcctggggg   4800

agactttagg agccagtctg tggcttgatg ctttctcttg ccctctgctg tgcaacagtt   4860

gaaatggtgg ttgttctatc agctgggatc caggagcaag gagacacaga gcagcgcagc   4920

agctgcccag caggggacgt gcatcaggag ccactgagaa acaggacttg agcgttgctg   4980

ttactgtagc agaactcacc ctaccctgac tgatgcacag ctctcccctc ccctccctcc   5040

ttcctcccat ctaagaaggc tgggaaggag gtcagagaaa aagctatgag tgagcatatt   5100

ttggattttg ttggtcagtg ggccccagag agctttgaag aattcagaag cagagagcag   5160

ggaggatctc aagagataaa atggccaaga gggccagaga caacctcacg cctagataca   5220

attggggaaa aaaaatgaat ggagctggga aagtgatggg gttggggaaa aaaatcccaa   5280

ttgaataaga tgaattttct gcccacatat ggaatggagc attgaaatga gaatgaattt   5340

aaaatagatt acatttcca                                                5359
```

<210> SEQ ID NO 2
<211> LENGTH: 5748
<212> TYPE: DNA
<213> ORGANISM: Homo sapiens

<400> SEQUENCE: 2

```
tcaggtccca ttttctcaga ttccagtcta agattacatg atactcaaaa tccaggaatc     60

taaggctgca cgagttttct ccttggattt tttgttccct atttaggcag ttagactgca    120

gaacatctac tgactcagga aacagatgtg ttagtaaaag cagagaatac atttctgggt    180

ttcaaaaaca ccccttcctc ccaggaaaga acattcctaa gagacttggg catcttgaac    240

acctaatgaa tctgaaagag gctctcactt tctgtgactg tctttaggga ctgtccacaa    300

atactctgtt tcttttcctt ttagggtgcc ttagtctgtt caggctgcta cagcaaaaca    360

tcttagactg ggtaatttat aaacaacaga aattcattgc tcacagttct ggaggttggg    420

aaattcaaga tcaaggctcc agcagactca gtgtctggtg ggagcctgtt tcttatagat    480

ggtgacttct gtgtgtcctc acatggcaga agggacagat gggctccctc aagcctcttt    540

tacaagaaca ctaatcccat tcatgggtgg agccctcctg acctaatcaa cttccaaagg    600

ccccacctct taaggctatc actgtgggga ttaggtctca acatctgaac tttggggaac    660

acattcagac cacagcacag gcccatagta ggatttccac ttgaactccc tcctctgctt    720

gaagttaggt acagccaagt aacaagcttt ggccaatgaa atgtgtgcag aagtgaagtg    780

tgccacttcc tgggggagac tttaggagcc agtctgtggc ttgatgcttt ctcttgccct    840

ctgctgtgca acagttgaaa tggtggttgt tctatcagct gggatccagg agcaaggaga    900

cacagagcag cgcagcagct gcccagcagg ggacgtgcat caggagccac tgagaaacag    960

gacttgagcg ttgctgttac tgtagcagaa ctcaccctac cctgactgat gcacagctct   1020

cccctcccct ccctccttcc tcccatctaa gaaggctggg aaggaggtca gagaaaaagc   1080

tatgagtgag catattttgg attttgttgg tcagtgggcc ccagagagct ttgaagaatt   1140

cagaagcaga gagcagggag gatctcaaga gataaaatgg ccaagagggc cagagacaac   1200
```

```
ctcacgccta gatacaattg gggaaaaaaa atgaatggag ctgggaaagt gatggggttg   1260
gggaaaaaaa tcccaattga ataagatgaa ttttctgccc acatatggaa tggagcattg   1320
aaatgagaat gaatttaaaa tagattacat ttccagccca tctgaatttc agactgagaa   1380
tatctgctgc acataattca agatcccaca gtctcaagag gcttgggtcc tgggctttga   1440
caatgactct tttcctgggc agaaggttgt acatggacac tgggagcacc taggcctgga   1500
agctgggaga actaggctct cctgtctgat gtcactttcc ctgtcacttt cccagggagg   1560
ccttccctga ctgcctgact taaaaggaac ttcctctacc accctggcca ttctctattc   1620
ctcttcttaa catcaattga cacaccacaa gttttcattt tttttttttt tttttcttga   1680
gatggagtct cactctgtca cccaggctgc acccaggctg gagtgcagtg gcacgatctc   1740
agctcactgc aacctccacc tcccaggtta aagcgattct cctgcctcag cctcccgaat   1800
agctgggact acaggcacgt gccaccacgt ccagctatac tgatgtgttt attgtctatt   1860
tccccacttg actgtaagtt tcaaaatggc agatattcct ctctctctct ctccctcttt   1920
tttcttttcc cttttattta taaaaaactt caaacataca gaaaacctat catgaagacc   1980
catttaccgc ttacccatca tctagatttc caactgttaa cattttactg tatttgcatc   2040
atgtttttttg gtgctggcat tttctgaagt atataatatt cttcactata tttcctttta   2100
aaaaattgaa gatggccggg cgcggtgtct cacgcctata atcccagcac tttgggaggc   2160
ggaggtgggc ggatcacgag atcaggagat caagaccatt ctggctaaca tggtgaaacc   2220
ctgtctctac taaaaataca aaaaattagc cgggcgtggt ggcgggtgcc tgtagtccca   2280
gctacttggg aggctgaggc aggagaatgg catgaacccg ggaggtagag cctgcggtga   2340
gccgagatgg tgccactgca ttccagcctg ggcgacagag cgagactcca tctcaaaaaa   2400
aaaaaaaaaa aatgaaggta aggagttttg tctgttgtat tcactgccat attactcact   2460
gcctggaagt tggtaggcct tcagcaaata gttgctgagt gagtagaagg cgttaaatcc   2520
tcatgacaac cctgtgcggt aggtgttatt atcccccatt ttacagaaga ggaaactaag   2580
gcacagagag gaaaagtaac ttccccaagg ccacatggtt ggcaggtgat gaaaggggga   2640
tttgagctca ggcaggctga gttcagagcc catgcattta gcgcacaatt gctctctgcg   2700
ggcaatggcc attcatctcc aactgggatg tttattcatc ctctttagat accatctaca   2760
gaggagaccc agaggaagaa gaggggctca caggctggcc aaaagcaggt gatcttcctc   2820
tggggacctg atgctctcac aaagcctggg gccttctgtc ctgccctggg gtggagacag   2880
aagactcctt cccagacgag tgacctttag ggtttgttat gaatagagat tccttctggg   2940
gaacgtgatg gctgatgctg ggaacccggg tccccagatt taacccctag gaatgtggag   3000
aggaatctcc agacctccac ccaggaggcc agctctccca gccacccagg ccagccagaa   3060
gagggtggtt ctaagcagct cttccagtta ttggaccact gggaggtgga ctggaacctt   3120
ccatgtccag gctgggaggc agctcctcag agtaaaaata actctaggct tcaaaatcct   3180
ggggtctgcc tcttcctccc cagctatgtg acattcactg gacaggtgcc tcatgtgggg   3240
ggactttggt tttcacatca atctaatggg actaaatatt ataccaacct ctcagcaggg   3300
ctgggactag ggtgaagcca gccaggtgct caaggcataa catttaggga ggtgcttgtt   3360
ctgaggcgcc aaccctgcac ttgctcaggc cccggggtga gggcctcggt agatttgcac   3420
cctggtcacc ttgctgcctc aacctggccc cagccctgcc tcccagggtt gtcgtgggaa   3480
ggaaatgaga tattgtatac aaagcatgtt agcacagcat gtagcatgcc cttagtgctc   3540
```

```
acttgtgggg aaaattctgt tattgttctt tttttttttt tttttttttt tttttttgag   3600
agagagtctc gctgtgtcac ccaggctgga gtgcagtagc acgatcttgg ctcactgcaa   3660
cttctgcctt ccggattcaa gtgattcccc tgcctcagcc tcctgagtag ctggattgca   3720
ggtgtgcacc atcatgcctg gctaattttt tttttttttt tgagacggag tctcgctctg   3780
tcgcccaggc tggactgcag tggtgtgatc tcggctcact gcaaactccg cctcccgggt   3840
tcacgccatt ctcctgcctc agcctcctga gtagctggga ctacaggtgc ccaccaccac   3900
gcctggctaa tttttttgta tttttagtag agacagggtt tcaccgtgtt agccaggatg   3960
gtctcgatct cctgaccccg tgatccgccc gcctcggcct cctaaagtgc tgggattaca   4020
ggcgtgagcc accgcacctg gccaattttt gtatttttag tagagacggg gtttcgccat   4080
gttggccagg ctgatctaga actcctaatt tcaagtaatc cacctgccta ggcctcccaa   4140
agtgctgggc taggattaca ggcgtgaacc accgcaccca gcctgttcct attattttta   4200
ttgactgcct ttctgaggtt ggctgggcct gtttcccagc agtggccctg ccttggacct   4260
cttgccatgg ccttcgtctc tccctccact tgtacatatt ataccctttt tattatttat   4320
ccccttgtag catggtttga ttcccattat ttactggttc cttgtcccat gtctcctcct   4380
ctgtgtcgac agcctggaaa caatgattgc taatatttac caagtgctca ccatgtgcca   4440
agccctgggc taagcattta catgctggat ttcatctcat ctttacaatg atcctatgag   4500
gtagggacta tgattatacc catttttcaa atgaggaaat ggaggcactt aaaaattgag   4560
taacttgccc aaggatgcat tgttagaaaa ggatggagct gagggtagaa tcaagatggc   4620
ttaatcccta aaacccaagg gatggaaccc agaacactgc ctcttccact cttcaccagc   4680
ttctgccctg cagggtacac gcagatggct ccaagcaggg gccccattgc tcactggggg   4740
aaactggcct ccctgagcta agtcaggtcc tgggcagagg gacagatgct ctctgtgcat   4800
ctctaggcca cagcagggcg tttccaagtc cttcccagac cagacggcgg cttctgctgt   4860
aggctatagt aataacaaca gcgttgagca ctcacactgt accagagcag gggtggcgcc   4920
gcgctgcaca cctgccgccc agggtctcca cagtcctcac gctgcccttg cattgattat   4980
tgtctttatg tgaccagtgt ggtagctcag gtgtcaagac ctcaaggcac ccagccaggg   5040
tcgcatctca cgtctatggc agatccaaga tctgaacttg gacttgtctg aatcctggat   5100
aagctggggg gtgaagctgg ctgctgagga tcctgtgtgc ccctcagccc tgttcccacc   5160
acctctgtgc ctcctccctg ctggcagcca ctgtggccac aatggggtta accccagagg   5220
aaggcattga aggcgctggg gctggggtgg gaaggaaggc atatttcggg gctccaagga   5280
cttgaagcct agctgctcca tgcccaggct ctgggacccc ccaatacatg cacacattgt   5340
ttaaaatgaa gtggaactcc aggcaggcaa gttttgattt aggggagaca gctcctccat   5400
ggtaatgata ctgagccttg ttatttgagc aaataggttt tctcccagcc tctcactcct   5460
ttctttgtaa ttcatcttcc atcctggcca catgcaggcc ctgcttggaa ctctctgggg   5520
actcctaccc cacaggatag tctaaaaccc tgccccggta ttcaaggctg tttgcagatg   5580
ttcctcaacc ccaccacctg ttgctcccaa aattcacaca ccccagacct gcacaccaca   5640
gttgttgcta ttccacacac aggtcgctgg gagcagcgca cggcccagcc ccgcctttct   5700
gcaagtggat ccctctgcct ggaaagtcct ccctcccctc ctctggat                5748
```

<210> SEQ ID NO 3
<211> LENGTH: 24586
<212> TYPE: DNA
<213> ORGANISM: Homo sapiens

<400> SEQUENCE: 3
attacaggcg tgagccactg tgcccttcct aattagctaa attttatgtt atgtatattt 60
tgctgcaatt aaaatttttc aagtgaggta tctataagga aaggtgagaa aatatgtaag 120
atacaaagat aataaaatcc agagcaagaa cagtatataa gtcctgtttc cttatgttga 180
aatatatcaa aatattcaac agaagacccc aggataggaa agatgtgaaa ttctagactg 240
gatcatcagg tccgacggat ttacaaagaa ggtggccgag gatctctctc cccagccttc 300
accccctcac tgactgtggg aaaataaagg gcttggggtt tggggaggag gtgttgcagg 360
aggagcggca gctccagcta tgagacctca cccagagggg gccaatactg cccctccaga 420
tgccaggcag gggacatgga agggtttggg gattcgttgt gggctggggt gggggtagct 480
tgcaggggtc tgcttgggtc ttgttcccta gggcctcctg gagggtggag tggtcttagc 540
agcaagaagc tggagttgga tgttggattc ctgagggccg aggaaggact tgcaagggac 600
ctccagaagg agaagtgcat ccccccccagg gtcaagagtg agggagccct gcagcaatgg 660
ccatctgtgg gacatctgtg acactgtcag ctggaagcca gcaggatggc ggcagctcaa 720
gtgagaccct tcccctcccc ttactatctc cacagccccc acttgtgggg gaggggagga 780
ggtccagaga aggagccccc caaactgcct ccccaggaca ggccccagct gggcaagggg 840
agaaggttta aacctagatc caattgggag tttggattaa tagcttgact ggacatttta 900
aatttgagtt gagaccatgt ttgtgactta aagtgatggt agaactgtct tatgtaagaa 960
ttggggccag gcacactttg ggagtccgag acaggtggat cacttgaggt caggagttcg 1020
agaccagcct ggccaacatg gcaaaacctg cctctactaa aaatacaaaa attatccagg 1080
catggtggtg tgtgcctgta gtcccagcta cttgggaggc tggggcagaa gaatcgcttg 1140
aacctgggag gcagaggttg caacgagcag aggttgcccc actgtactcc agcctggatg 1200
acaaagtgag tgagacttcg tctcaaaaaa aagagttggt cccattctcc agtgggctag 1260
ccttggcttg tctcatggtg gaggaggctg gcgggggtgg gtcaggttca ggggggtggg 1320
ggaaggtggg gagcagaggg tgggagagag agagagagag agactgcaag gactgcattc 1380
tttttgaggc tcaggctcag aactagcaca aggtcacttc caccacattc aatggaccaa 1440
agagagtccc aaagccaacc cacattggag agaacgaagg caaagtcaca ttgcaaaggg 1500
gtgtggaaac agatagtggt gcagaatctg gcccgctttc ataatcagtc cactggaaga 1560
ctttgttttc ctcgcaagga aggttggaaa tgtagactca ctgcttgtcc aggcagaaga 1620
ggaaatgagt tcagggaaga gcttgccagt ccccagcctt tgcccagccc cctactcatg 1680
cacatttagg cacacaccta ctgtgtgctc agcccagcag ggtagattag agagagcgag 1740
ggcgtcggga tagagggcct gattccccaa ccgggtgact atcacttccg gtctcatgac 1800
ctccatgttc tcatctgtaa aatgggggata aacatcctca tcatctctcc tgccattggt 1860
atggtggtga caaaaaacac tttatcgatt catgaaagtc atcagacaaa gtggatgatg 1920
ctgtccctgc cctcaaaggt gttaaataaa gaagatgaga attcaataca tgtccccagc 1980
tctggtgaga ctgtaggggt tgtgttaaca agggagggag agacatcaga gagctgttgg 2040
caggggagag ccctgtggcc aagccttgac agatggtgaa cagaatctgg aaagacagag 2100
ggcatggggc atggcagggt gtggaaacag cacacttgca aaagtgtgga ggctggacac 2160
atgtgatata aggcagggtc ccctacccca tgattcaaag cagaaattcg caaagacttt 2220
gatgtaggct gggctgggag ttgactacac ttgcatgcct gttgcttggc aggatggctt 2280

-continued

```
tcaaaaaaga aaaaaatata ataatgaaag attgaaaaca gattattggg gagaaaagta   2340
tcccaggcgc tagacggctg tctctgcagc ctctggctcc tgtcccaccc attccccggc   2400
cctgacgcaa ggctggctgg aagaaggtgt tctcgagatt gttcaggctg agggcctgac   2460
tggcaggaga ctgaagccta ccccattcct gcctgggtgc caagctctgc atgaggttta   2520
aatataccca cagcctgaca ctatgcccta gatcatgcta aatgtttcca tactccttga   2580
attctcttct caaggttcat ttattgtccc catttttcag atcagtaaac tgaggcccag   2640
agaggttaac tggtttgccc acagtcacac agccagacaa gtttgagtat gtctgattct   2700
attgccttat tccaggtttg ggatacaggc agagtaggga gaggtttagg atggtaaaga   2760
agaatgttcc aggaggaaca gagttagtgt aagggcagtc taatctagag tcagaatttg   2820
gagctgtttg ttacagcagc atgacctagc ctatcctgac tgatacaaat catggtaaac   2880
taatttatat gtcctgaaaa atattagaac ttagcatcta cctcttagga gagctttttt   2940
tttttttttt aacttttaca ttttggcaaa acacaccgaa cataaaattt accatctaag   3000
caatttttaaa tgtacaatgc atggctttaa gtacattcac attattgagt ttctatcacc   3060
atccttccac agaactcgtc atcttgcaaa actgaaattc taaacccatt aaggaaactt   3120
ctcatttccc cctccccagc ccctggcaat tccactttct gtctctatga attggactac   3180
ttttgacaga tacctcctat aaatggaatc acacagtatg catctttctg tgactgattt   3240
atttcactta gcataatgtc ctcaagcttc atccctgttg tagcatgtat cagaattgcc   3300
ttcctttttt aaggctgaaa atcttccatt gtgtggatac actatatttt gcttatccac   3360
taatctatca atggacactt gagtgccttt caccttttgg ctattgtgaa taatctgcta   3420
tgaacatgga cacacgaata tcagaggcag cctttttcaag caaagggttt ttggggaaaa   3480
agccactgtc caggactcta ggcttggcca ctaacttgct gtgtagctgt gggcacattg   3540
cttcctgcat cgtgtatggc aattctaact ctctccacct tcactgccta ctcacagccg   3600
tgtgctgggg accagattag accatggact atgaaactct cagcaaagaa aaagccacga   3660
ggggctgtta ttgttattac tcagtggggt cagggcagtg gcttcccaaa ggcatgagtc   3720
actcatggtg gaattccaga catcaggagg gccgttctgg gcagcagagc ccagattcca   3780
gacagagcag tgaccctgac ccggagcccc taggggagcc acaccctttc tctttggcca   3840
ctggctgctg tgaggaagga gtcagtgaat gtcataatca tatgggcact tagggtgaga   3900
gcctccagtc ccactgcctc acgtaactat ttaaggaggc tcagaaaggg tcatgcactt   3960
gcccagagtc acacagctag acagtggtgg aagctggcct gggtcagatt tggacatcta   4020
cagaagccct tctcctccct gctcgcaccc ctcttagccc cagcatgtga ggaaggcagc   4080
tgtctccctg agctccgtcc ttctatgcct tgggtttagc catgttgact gctgtaacaa   4140
ataactccaa aacctcagtg gctttgcatt ataaatgctt ggttctttct cacatcaaac   4200
tgcaataagt cttgacagga gggctctgtt ttctgcaggt catataggga ttgagacttt   4260
tcctatttgt ggctttcctc attctcagag tcctctccat tcagcaggca gatggcagaa   4320
agattgtggg tagaagattt ttataagcca gacctgaaat cagtacaatt atttttgctt   4380
acatcccatt ggccagagct cagtcacatg accacatcta actgcaaaga aggctgggaa   4440
atgtatccca catgtgtgcc caggaagaag aagatggcta ttggtgagcc ttggtagtct   4500
tccacaagaa catgacccag ttctggccaa taaaacataa agaaagtatg ctgggacagg   4560
aggtttgaga agggctggcc tcaattatta tataaaaagg ggtgtgggga aggtccccta   4620
ttctttccct ttaagtggtt gcatgaggat gcgatgtctg gaactttggc agccatgttg   4680
```

agagcatgac gggccaagcc tcagggctac agccaatata ctgagggtgc tgaagccaaa 4740
atgcgggtcc tagatgacat cactgaacct ctgaatgaac caaaactgga gccacgtaac 4800
ctccagattt cttgactgcg aaggcaccta ttattgaatt caggagtaat agggtattct 4860
attacttgca gcctaaaaca tcctagctga ttgacactca ggtgcaaatg ctgaaaacag 4920
ctaagaggac aaggttaagc catgccagct gttacaacga ataactccaa aacctcagtg 4980
gctttgcact acaaatactt ggttcccttg aaacccctcc tctgcttgaa gttaggtaga 5040
gccaagtaac atagctttgg cctactctgg atgttgtgct tttttgggga agttggggac 5100
agagcagcag ttcaagcaca aaatgacctg gctgctttgt gccaggtcct tttatacacac 5160 agtgtataca cgggagcaaa atgcctggac tcaaatcttg agtctgccac ctcaccagcc 5220
atgtgacctt gggcaaagtc aatcaacctc actgagccct agtttcccca ttgaaaacat 5280
tggggtgatt ataaatattc tacccacaga gtaaaggatt aaatgtccaa ttcagataaa 5340
gaacttggca cattatctgt aaataaacac ttaaaagatt ctgaccagag cctggtggga 5400
tgtgagtaat atcaacccca ccttagagat ggggagtcta gggttcaagg aaatgaagtc 5460
caaggacata taaataataa gagacagagc ctggatttta atacagacct aattgaacac 5520
ctgctatgtg ccaggcattg tgtgaggtgt ttagatatat tatcccattg aacatactag 5580
caatcctgca tgggaggtat tattattatc attattgtta ttcctattgg acaaatgaga 5640
aagccaaaac tcagagaagt gaaaagactt gcctacaggc caggtcaaga tgcagtactt 5700
gaacctaggc tgagtccaag cctttattct ttccaccatg tataagcctc cctaacagaa 5760
gcccaccaga ctattatagt ggaattgtag gcatcagagg agtaatacat ttggctccca 5820
tggctattca gggttccctg aagtcatccc caaaagctgg ctgccagtcc agcctgtcac 5880
caaggttgtc ctggtgatgg ctttaccctc actcctccag tagaataact gggccctgga 5940
gtggatggtc ctgagggagg aagtttggct cacttgataa agcagaactt tcaaacactt 6000
tgagctcatc catgatggaa taggctgcct tgggatgcga tgagttctgt ggtcctggga 6060
ggatacaagc agagaaagtc tggtggccac ctgcaaggaa gattattaag acagttactg 6120
catagaaagt gaaattagat tcaaagacct ttcaggtttg aaatctgtgg ttgcaagatt 6180
ctcaggtccc attttctcag attccagtct aagattacat gatactcaaa atccaggaat 6240
ctaaggctgc acgagttttc tccttggatt ttttgttccc tatttaggca gttagactgc 6300
agaacatcta ctgactcagg aaacagatgt gttagtaaaa gcagagaata catttctggg 6360
tttcaaaaac accccttcct cccaggaaag aacattccta agagacttgg gcatcttgaa 6420
cacctaatga atctgaaaga ggctctcact ttctgtgact gtctttaggg actgtccaca 6480
aatactctgt ttcttttcct tttagggtgc cttagtctgt tcaggctgct acagcaaaac 6540
atcttagact gggtaattta taaacaacag aaattcattg ctcacagttc tggaggttgg 6600
gaaattcaag atcaaggctc cagcagactc agtgtctggt gggagcctgt ttcttataga 6660
tggtgacttc tgtgtgtcct cacatggcag aagggacaga tgggctccct caagcctctt 6720
ttacaagaac actaatccca ttcatgggtg gagccctcct gacctaatca acttccaaag 6780
gccccacctc ttaaggctat cactgtgggg attaggtctc aacatctgaa ctttggggaa 6840
cacattcaga ccacagcaca ggcccatagt aggatttcca cttgaactcc ctcctctgct 6900
tgaagttagg tacagccaag taacaagctt tggccaatga aatgtgtgca gaagtgaagt 6960
gtgccacttc ctgggggaga ctttaggagc cagtctgtgg cttgatgctt tctcttgccc 7020

```
tctgctgtgc aacagttgaa atggtggttg ttctatcagc tgggatccag gagcaaggag   7080
acacagagca gcgcagcagc tgcccagcag gggacgtgca tcaggagcca ctgagaaaca   7140
ggacttgagc gttgctgtta ctgtagcaga actcacccta ccctgactga tgcacagctc   7200
tcccctcccc tccctccttc ctcccatcta agaaggctgg gaaggaggtc agagaaaaag   7260
ctatgagtga gcatatttg gattttgttg gtcagtgggc cccagagagc tttgaagaat    7320
tcagaagcag agagcaggga ggatctcaag agataaaatg gccaagaggg ccagagacaa   7380
cctcacgcct agatacaatt ggggaaaaaa aatgaatgga gctgggaaag tgatggggtt   7440
ggggaaaaaa atcccaattg aataagatga attttctgcc cacatatgga atggagcatt   7500
gaaatgagaa tgaatttaaa atagattaca tttccagccc atctgaattt cagactgaga   7560
atatctgctg cacataattc aagatcccac agtctcaaga ggcttgggtc ctgggctttg   7620
acaatgactc ttttcctggg cagaaggttg tacatggaca ctgggagcac ctaggcctgg   7680
aagctgggag aactaggctc tcctgtctga tgtcactttc cctgtcactt tcccagggag   7740
gccttccctg actgcctgac ttaaaaggaa cttcctctac caccctggcc attctctatt   7800
cctcttctta acatcaattg acacaccaca agttttcatt tttttttttt tttttcttg    7860
agatggagtc tcactctgtc acccaggctg cacccaggct ggagtgcagt ggcacgatct   7920
cagctcactg caacctccac ctcccaggtt aaagcgattc tcctgcctca gcctcccgaa   7980
tagctgggac tacaggcacg tgccaccacg tccagctata ctgatgtgtt tattgtctat   8040
ttccccactt gactgtaagt ttcaaaatgg cagatattcc tctctctctc tctccctctt   8100
ttttctttc ccttttattt ataaaaaact tcaaacatac agaaaaccta tcatgaagac    8160
ccatttaccg cttacccatc atctagattt ccaactgtta acattttact gtatttgcat   8220
catgtttttt ggtgctggca ttttctgaag tatataatat tcttcactat atttcctttt   8280
aaaaaattga agatggccgg gcgcggtgtc tcacgcctat aatcccagca ctttgggagg   8340
cggaggtggg cggatcacga gatcaggaga tcaagaccat tctggctaac atggtgaaac   8400
cctgtctcta ctaaaaatac aaaaaattag ccgggcgtgg tggcgggtgc ctgtagtccc   8460
agctacttgg gaggctgagg caggagaatg gcatgaaccc gggaggtaga gcctgcggtg   8520
agccgagatg gtgccactgc attccagcct gggcgacaga gcgagactcc atctcaaaaa   8580
aaaaaaaaaa aaatgaaggt aaggagtttt gtctgttgta ttcactgcca tattactcac   8640
tgcctggaag ttggtaggcc ttcagcaaat agttgctgag tgagtagaag gcgttaaatc   8700
ctcatgacaa ccctgtgcgg taggtgttat tatcccccat tttacagaag aggaaactaa   8760
ggcacagaga ggaaaagtaa cttccccaag gccacatggt tggcaggtga tgaaaggggg   8820
atttgagctc aggcaggctg agttcagagc ccatgcattt agcgcacaat tgctctctgc   8880
gggcaatggc cattcatctc caactgggat gtttattcat cctctttaga taccatctac   8940
agaggagacc cagaggaaga agaggggctc acaggctggc caaaagcagg tgatcttcct   9000
ctggggacct gatgctctca caaagcctgg ggccttctgt cctgccctgg ggtggagaca   9060
gaagactcct tcccagacga gtgaccttta gggtttgtta tgaatagaga ttccttctgg   9120
ggaacgtgat ggctgatgct gggaacccgg gtccccagat ttaacccta ggaatgtgga    9180
gaggaatctc cagacctcca cccaggaggc cagctctccc agccacccag gccagccaga   9240
agagggtggt tctaagcagc tcttccagtt attggaccac tgggaggtgg actggaacct   9300
tccatgtcca ggctgggagg cagctcctca gagtaaaaat aactctaggc ttcaaaatcc   9360
tggggtctgc ctcttcctcc ccagctatgt gacattcact ggacaggtgc ctcatgtggg   9420
```

gggactttgg ttttcacatc aatctaatgg gactaaatat tataccaacc tctcagcagg 9480
gctgggacta gggtgaagcc agccaggtgc tcaaggcata acatttaggg aggtgcttgt 9540
tctgaggcgc caaccctgca cttgctcagg ccccggggtg agggcctcgg tagatttgca 9600
ccctggtcac cttgctgcct caacctggcc ccagccctgc ctcccagggt tgtcgtggga 9660
aggaaatgag atattgtata caaagcatgt tagcacagca tgtagcatgc ccttagtgct 9720
cacttgtggg gaaaattctg ttattgttct ttttttttt ttttttttt ttttttttga 9780
gagagagtct cgctgtgtca cccaggctgg agtgcagtag cacgatcttg gctcactgca 9840
acttctgcct tccggattca agtgattccc ctgcctcagc ctcctgagta gctggattgc 9900
aggtgtgcac catcatgcct ggctaatttt ttttttttt ttgagacgga gtctcgctct 9960
gtcgcccagg ctggactgca gtggtgtgat ctcggctcac tgcaaactcc gcctcccggg 10020
ttcacgccat tctcctgcct cagcctcctg agtagctggg actacaggtg cccaccacca 10080
cgcctggcta attttttgt atttttagta gagacagggt ttcaccgtgt tagccaggat 10140
ggtctcgatc tcctgacccc gtgatccgcc cgcctcggcc tcctaaagtg ctgggattac 10200
aggcgtgagc caccgcacct ggccaatttt tgtattttta gtagagacgg ggtttcgcca 10260
tgttggccag gctgatctag aactcctaat ttcaagtaat ccacctgcct aggcctccca 10320
aagtgctggg ctaggattac aggcgtgaac caccgcaccc agcctgttcc tattattttt 10380
attgactgcc tttctgaggt tggctgggcc tgtttcccag cagtggccct gccttggacc 10440
tcttgccatg gccttcgtct ctccctccac ttgtacatat tataccettt ttattattta 10500
tccccttgta gcatggtttg attcccatta tttactggtt ccttgtccca tgtctcctcc 10560
tctgtgtcga cagcctggaa acaatgattg ctaatattta ccaagtgctc accatgtgcc 10620
aagccctggg ctaagcattt acatgctgga tttcatctca tctttacaat gatcctatga 10680
ggtagggact atgattatac ccatttttca aatgaggaaa tggaggcact taaaaattga 10740
gtaacttgcc caaggatgca ttgttagaaa aggatggagc tgagggtaga atcaagatgg 10800
cttaatccct aaaacccaag ggatggaacc cagaacactg cctcttccac tcttcaccag 10860
cttctgccct gcagggtaca cgcagatggc tccaagcagg ggccccattg ctcactgggg 10920
gaaactggcc tccctgagct aagtcaggtc ctgggcagag ggacagatgc tctctgtgca 10980
tctctaggcc acagcagggc gtttccaagt ccttcccaga ccagacggcg gcttctgctg 11040
taggctatag taataacaac agcgttgagc actcacactg taccagagca ggggtggcgc 11100
cgcgctgcac acctgccgcc cagggtctcc acagtcctca cgctgccctt gcattgatta 11160
ttgtctttat gtgaccagtg tggtagctca ggtgtcaaga cctcaaggca cccagccagg 11220
gtcgcatctc acgtctatgg cagatccaag atctgaactt ggacttgtct gaatcctgga 11280
taagctgggg ggtgaagctg gctgctgagg atcctgtgtg cccctcagcc ctgttcccac 11340
cacctctgtg cctcctccct gctggcagcc actgtggcca caatggggtt aaccccagag 11400
gaaggcattg aaggcgctgg ggctggggtg ggaaggaagg catatttcgg ggctccaagg 11460
acttgaagcc tagctgctcc atgcccaggc tctgggaccc cccaatacat gcacacattg 11520
tttaaaatga agtggaactc caggcaggca agttttgatt taggggagac agctcctcca 11580
tggtaatgat actgagcctt gttatttgag caaataggtt ttctcccagc ctctcactcc 11640
tttctttgta attcatcttc catcctggcc acatgcaggc cctgcttgga actctctggg 11700
gactcctacc ccacaggata gtctaaaacc ctgccccggt attcaaggct gtttgcagat 11760

-continued

```
gttcctcaac cccaccacct gttgctccca aaattcacac accccagacc tgcacaccac  11820
agttgttgct attccacaca caggtcgctg ggagcagcgc acggcccagc cccgcctttc  11880
tgcaagtgga tccctctgcc tggaaagtcc tccctcccct cctctggatc ctcctgggtc  11940
aggctgggtg ctcctctgaa ctcccaggct gagggttgct gtgtaatttg atactacatt  12000
gacattgcag gaagatcatg tatggctgag tagctaaaaa tgcaggcttt gaacttggat  12060
gtgggttcag cctcagctgt atctcccgcc agctgtggga cattgggctg gcgtctctga  12120
gcctcagttt gcttctctga acatagaatg atacgcccta ctccattaag gtgctgaggg  12180
tgaaggaaac cacgggctca gtgtgggcag cttggccagg gctccaagcg catcgggtgt  12240
tcatgtagtc cttctagtgc caggcggtca ttagcaactt ggtgccagtc tctgagctgg  12300
tctccaggac ggagcagtgg agggaccatg tagcccctgc tcccacaaac acagacattg  12360
gacagccaat tagttacccc agttcgttac catggagact ataattaggg attatagtca  12420
ccctgcccaa gcgcacaggc ctcacctccc atccttgcct tagctttgaa gctccctgga  12480
gcaggatcta aactggattt gtctctgtaa cctcagttcc tcattattca tggtcggaat  12540
gctcagcaaa cgtttaagtg gaagagattt ccataacaaa cacttgggag ttcagaggag  12600
cacgcggtcc aacctgaaca gagcaggagg atctcagagg agggaggcca ctaggtagga  12660
tgcggcggca ctaagggtag cacttagttt gtgacaagga ctgttccaag cacaccactt  12720
ggatcatcta ttaaattctc acttatttat ttatttattt taaaattgtg tttatttatt  12780
tatttattta tttatttatt tgtttgtttt gagatggagt ctcgctttcc aggctggagt  12840
acagtggcac aatcttggtt cactgcagcc tcttcctccc aggttcaagc gattttcctg  12900
cctcagcctc ccaagtagct gggattacag gcatgtgcca ccacgcccgg ctaatttttg  12960
tattaagaga tgaggtttcg ccatgttcac caggctgatc tcgaactcct gacctcaagt  13020
gatctgcccg ccttggcctc ccaaagtgct aggattacag gcttgagcca ctgcgcccag  13080
ccagtgatca cttatttaga tcacttacta aaatcattta attatgtcaa cacctctgtg  13140
aagtatgtac tgttatcacc attcccattt catagatggg gaaactgagg cacagaaaag  13200
ctaagtaaac tgctcagagt tacagagcct gcgagggcca cagccagaat tcaaacccag  13260
gccatctgcc tccacagtcc actttctatg tccctctccc gagatgatgt ccctttccca  13320
ggggtgtctg gaaagggtct ggcccctggt cccagctcaa gcagctgtcc agggaagcct  13380
gaagacctgg cccatctcca ctgcccaccg ggcttctctg cgctccactt cccaggtgga  13440
ctgtggaggc aaataaggcc ccagctgcag cctctgaaga ctcctgccaa gctggcactt  13500
tgaggcctgg gggtgtccca ggggatccca gcccagcagc tgggctgacc tcagggccag  13560
tgtttccgta aacacccgga gagccagccc cacgtggttg atctgtgggt tgctggccaa  13620
gaggggctga ggtttggctg acctcgtgcg gtttctttca acaaggctac ttccaccccc  13680
tccgcctggc tgggcttcca gtaatgaagt gttttctctg gggctagggg agctgatggg  13740
gctggtggcg tggggcactg gggtcttcct gtcccacgtg ccctccaccc tgggcttctg  13800
gaagctggtc tagatgcccc tagctgccgc ctgggcagcc catatgccca cgccggtccc  13860
tgatagtgaa ctggcccgta aggggaccag gtctcgggat ctgagcatgg agcaggggct  13920
gcgcccagga gatagggtgt ggctagactt tcccctgctg gtcctttccg gggatctgag  13980
gggaaacttc tcctggggac acacccgggt agctcagaga tggaagaaaa ggtctccatt  14040
acagctgcca cctcttcccc acccaaagag agtgtccgca gggggccgtg gggcaggagt  14100
gagtactgaa ggaatactaa ccacgatcac tgctaccatc tcctgaatgt cactgcccca  14160
```

gccctttaat tctcacaaca aaccttggaa actgaggctt agagagagga agtggctggc 14220
ccaaggtcac atagtgagta aatgagcaga gcttctcccc ctttcccttg aatcacctct 14280
atcttcctgt ccagatgcca ggcagcagga actagcaggt gcttttgggt catcttttaa 14340
gaggcaatat agcacaatga gtgagagcag ggactcaagg gccagccacc tgggttcaaa 14400
tcccagctct gcttcctact ggctatgtga ccttgggcaa gtcactcaac ttcttggttc 14460
ctcagtctcc ccacctgtat aatgaggata ataatgatgc ctcctttagg gggtttctgt 14520
gaggattgca tatacacgtg acacataata agccctgtgc catgctagtt atcccagcct 14580
ctcactcttc ccattgaaaa ggtgaagaca cagacccaga gatggaggca aattctgcag 14640
gggtcatgcc cggggcagag catggttcag ctatgtctcc tatggtgctg ccaaggagcc 14700
accatgggct tgagctgaga ggagccacct ggcaccggac acgtgacctc ctcgagggaa 14760
gggaggctct gcagagagca ggggatggtg gaggagcctg gctttatctt ccatccttca 14820
ggagcgggga agggcagtgt cagagccagg agaggagaga agcgaatgaa cgtgctgtgt 14880
gagctccagt cagtccctac tgactctggg cctgtcactc ctgctgaggg actcgggtgt 14940
ttggactttt agacttggag gggctcctcg gtggggcctt gggggctgct ctgggtgagg 15000
gctctcacca tttgcttcat cccaaaccac tgtccttggg cctgttttaa atattagagt 15060
gtagcatggg gttttgctgc tctaacaaag ggtcagccat cttgagaagg aggctctgtg 15120
atgagcaggg aatggggctc ccctgccccc ccgagaccct ggggcccaag ctgatgactg 15180
gccagtgact cactcccttc tcagcatgtc ctgtcatccc atgactggga gcccctcggg 15240
ggtggctcct aaccaaggtc cccctgacca aggcctcccc ccaccctccc cctaacacac 15300
atagagactg ggaacaatta actccctcct aaggccagac cagatgttca cgtgggcatt 15360
ggttttgttg accacatgtg actcaggagc tccctcagag ctggaagagt cccaagaggc 15420
taaaagggca acctgtcacg tcacagctgg gaaactgagt cccagagaag ccaggtgagt 15480
tgcctaacat ccctcagggg tagaagggag gaaggaacct ggagttccca tgcctgaccc 15540
agaggctttc tacctctcca aatagttctc ggatgtgccc aaggcctcag tccccattcc 15600
tacctccagt tgcaaatgtc ctccccaact acacagagcc tctcagcttc atcccacccc 15660
acctccaact ggctctcatg gtttcatcca ggctcagcta cttgcagctc cccaaatagc 15720
tcctgctgtc aggccacctc caggcctttg tactctcctg ctgctctgtt ttattttcct 15780
cttcacctgg acaactccta atcttgctcc aagactcatc tcaggtgtca ccttctccag 15840
gaagcctttc aaaaccacct cctccacctc ccaggctggg ttaggtcctc catctcttca 15900
ccctcagtac ctagtatctc ccacttactg tgctggaatc atctctttgc ttgtctctat 15960
attgccctct agtctgtgag ctcattgtgg acagagacct tagtttttat tcttaatagt 16020
agggaatgac ctattacatt cggtgtttgc tgaatgaatg cataagtgga tggatggatg 16080
aatgaatgaa tggttggatg gaagaataga tacatggatg gatggattga tggatggatg 16140
gaatgagtga ccaaatggta gatgaatgga caaatggacc gacaaacatg gaaggatgga 16200
tggatggaca gatggattga tggacaggtg gattgatgga caggtgggtc gatgggcagg 16260
tggatgaata aatcaggcag ataatggcat ctgtagggac tcagacagtg agggctaagt 16320
ccctggagcc tggatatcct gactgatgaa ggtgctcttg gatgggaagg gaataaccta 16380
acctgttgtc ttcctactcc aagagatatt tggtccagaa caaagccacc cctgccctgg 16440
tgcctgctcc cttctgacca acaggttcca actcagtggg gtctcctgaa ctctggtaac 16500
tcatctgaca ccagagccta taggaatcac cctgtctctg acattcaggg attctgcatt 16560
cctgaggccc tccctccctg cctctcttca ggtcagagct gccgccccat aaatgctttc 16620
aagcatagaa acatacaccc ctagagccag gaagttgtaa aaatgatggg attcacccct 16680
ctaccatttt tgcagatgaa gaaactgagg ctgagcaagg ccaagaaact tgcttaagga 16740
cacacagcaa tagagctggg ataagagctt gggtctttca attcgtttat tcgttcatac 16800
agcaagtatg tatctagcgc ctaaagtgcc aggctcagtg cctattcccg ggcatgctag 16860
gcctgtgcat aagctttcat gttaatttaa aagctatttc catcctccat atgacctcct 16920
ccagctcccc agcaggctgg tctatgcctc actagctgca tgcctggcat gatccctatg 16980
acaacaccct ctcccagcaa atgaggacca cttcattgtc aggaagcctg gctgggactg 17040
gtgtgtgctg ccgtgtgcag aggaggcagt cacatgtgtg tgctgtgagc tgcacattcc 17100
atcctagcct tagtgaggac cgtattagtc cctgcacgct catccttgcc agctcagact 17160
ggagccaagc attaaactgt tcaagcccca cagctgcccc aggcgagcca ttgcatggca 17220
cctgggagct cagggccagg agcagacctc tgaattcctg cccaaaccag ggaatatgtg 17280
gtgagaggag gtcataggga ggtgcctggg ggctggacat ttgcaagcca gctgagcagg 17340
cagtactcag cactttcctc ttcacccctc ccaccatggc aaaggcaggg gcagcgtggg 17400
ctagccagcc ttggagagat ggagcctcaa gtctaggggc agcagcccag cctcgggcga 17460
gccagggcta tttgctgggc cttctatgag gcttccatga agtatgtaac ctcgccgaag 17520
acatggaact actcagagtc attaagagcc aaagaaaggc tcagctgcgt ttaacagaaa 17580
agcttctggg aacaaatcaa tgaattggag aacaaaggaa gactgcagaa gacgaacaga 17640
accagaagcc atgtctagga tgaaatcaac atgaggtaga gaatcctgat gacattgatc 17700
aggatgaaag aagtatgagg caagggagta aaatcaaatg ccgagtaaaa agggggaaca 17760
acgttgacca aggaatttga agttaattta agagctgtta tgaacaatac aaaaaagaaa 17820
attataggcc catttcactt atgaatatat agatagaaaa acactaaaca aaatatttgc 17880
tgactgaatt cagcagagtt aaaataatga caccacatca ccatcaggaa gcgtttatcc 17940
cggaaaaaca ttccagaaaa tccaccagtg taattcacta catcattaga tccaaaggaa 18000
aatctatgat gtcaattgat gtggaaaaat tttttgataa gttccttttg tatttatgat 18060
gcttacaaat ttgaaaattc tgggaaaatg gagaaattaa tagaaaggta taaaatgtca 18120
aaagatgggc ccaagaagaa atagagaatt tcagtaggtc aatcagtatt acagaaactg 18180
taatggtgtc aaagccctcc cactccccta aaaatcagcc tagatgttct catgggtaag 18240
tactgctgaa cctttttttt tttttttttt tttttgagac aaggtctcat tctgtcgccc 18300
aggctagggt gtagtggccc aatcctggct cactgcaacc tctgcttccc aaggctcagg 18360
tatcctcctg cctcagcccc tcacgtagct ggaactacag gcatgcacca ccacacccag 18420
ctaatttttg tatttttagt agagatgggg ttttgctatg ttgcccaggc tggtcttaaa 18480
ctcctggact caaacgatcc acctatctag gcctcccaaa gtgctgggat tacaggtgtg 18540
agccaccgcg cccagcctgc agaaactttt tagaaacaat taattcgtat catatgcaag 18600
ttgcttaaaa agaaaacaaa agaaaaaaaa accaacctat cttattttaa aagtgttgtc 18660
ttgattataa aagccagata agacaatacc acaaaggaaa gtataggtcc atttcactta 18720
tgaatatgga taggaaaaca ctaaacaaaa tctttcctga ctgagtctag cagagttaaa 18780
ataatgatac tacatcacca tcaggaaggg tttatcccag aaaagtatcc acatctgaaa 18840
atccaccagt gtaactcact acatcattca atcaaaagga aaaatccaac gatgtcagct 18900
gatgcagaaa aaggttttga taaggtcttt atgtatttat gatttttaaa aattcttagc 18960
aaactaggag catgagagaa gttccttaat ttagtaggga tttttaatac caaaaaccta 19020
cagaaaatat tgctagtgga gaaaagtttt atataataca tgccttttaa ggtgaggaac 19080
aaggcaagaa tgctagttat tactgctact gtttaataca tagagctgga gagctgggct 19140
gagctacaag gaaagaaaat aagaggtgta attattggaa gggaagagat aaaactgtca 19200
ttgtttgtag atggtgtgat catctacctt gaaaaaccaa ccaaataaac tgacaaaata 19260
ttagaacaaa taagagagtt cagcaaggtt gccagataca cagtcagcaa caaaaatcaa 19320
tgacgctttt acatcagcaa taactaacca gaaaaacaca acataatttt gacttaaata 19380
gaaaggtttt aaaataatat atacatataa atatattata tataaaatgc atatacatat 19440
atatatacac acatgcacac attttaaaag cacagctggc tatggtggct cacgcctgta 19500
atcccagcac tttgggaggc cgaggtggga ggactgctta agctcaggag ttcaagacca 19560
gcctgggcaa catattgcca aaatttttta aaaaaacatt tagccgggca tggtggcaca 19620
cacctgtagt cccagctact aagggggcta aggtgggaga actgcttgat tccaggaggt 19680
ggaggctgca gtgagccgta attgcgccac tgcactcgag cctaggcaac agagcgagat 19740
tctgtctcaa aataaataaa taaataaagg tatatatata cataagtata aaaatagcgt 19800
atatatataa aacattatat ctctctctac acaccacaca cacacacaca cacacacaca 19860
cacacacatt attatgtttc taatcacatg aatgaaatct acatgtaggg tgcatttggc 19920
agctctgggt gtcatcaggg atctgagttc ctttatttct ccttcgccct cttctgcaca 19980
cgaagtccat cctcagggta ccctcatggt ccaagatggc tgcagaactc caccatcacg 20040
tccgtattac tgactggaag caggaggcag caatcagtgg tggtggagtc accaaaggga 20100
agcccttcct tttaaggagc ctttccagaa tcggcacaca acactcctgc ttgtatctcc 20160
gtgctggaac ctatcccgtg gccccgcctc ctgcaaagct gagtgcgtcg ccaccccaaa 20220
caaaaaaatc agtgtttggt gactgaggga ggagggaaga aggatattgg aatgggcatt 20280
gatcaggctc tgtcacagat ctcagtctcc aaaacacgaa actggggcac tgaggtccag 20340
agaagtgagg gaatttacac acagccacaa agcaaattag cagcggagtt gggattttca 20400
cctgactgtt gaccttccca tggtacaggt gtcccctcac accctggtac atccagccac 20460
tacagcactg cccctcctca cttccagccc tgctggggtc aggatctgtt ttgtatttct 20520
ctgtccccac tacctaatgt cacacctgtg agctccacct ccccagcgtc ggcttgggac 20580
ttggcatggg gtagaggccg taagcgggaa agcgggcaca cacctcggga gctgacaaac 20640
tgcaaagggc tttcaaccgc agatatttac ttgtggcttc catatgctgt accttgatgg 20700
tgatgtttcg taagtttcac ttttcagatg catttttttt tttttttttt ttttgagatg 20760
gagtctcact ctgtggccca ggctggagta cagtggcgcg atctgggctc accgcatcct 20820
ccgcctcccg gtttcaagca attctcctgc ctcagcctcc tgagtagctg agattacaga 20880
tacgggccac cacgcccagc taatttttgt atttttagta gagacaaggt tttgccatgt 20940
tgtccaggct ggtcacgaac tcctgacctc aagtgatctg cctgcctcgg cctcccaaag 21000
tgctgggatg acaggcgtga gccaccgcgc acggccagat gcatttctta gacgctaaaa 21060
atgttcagcc tggcccaggc ctggaagaac atgcaggccg cttttatttt tatttttttt 21120
taacagatgg agaaactgag acccagagaa gcaaaagtgt gtgtcccaga tgccaaggta 21180
cctgcggcaa agaatattac ctagatgtcc ctcactctgg ttctccttca ttgatacaca 21240

```
tggaatgatg gtatttcccc gccttccttg cagttaagtt ggggccatgt ggctagctct  21300
gactaataag atgtgagtag aagtgatgat gtggcttctc catccctctt ttttcctgcc  21360
aaggtgacct tggaggccac cggtctagaa cagggattca caaactgtaa tgtgcatgca  21420
aatcacctgg gggtcttact aaaatgcaga tcctgatagt ggggtctggg agtctgcatt  21480
tccaacatgc aaccagctga tgctgatgcc atcggtcctt ggaccacaca cttgagtagg  21540
gaggagctac aggatgtgcc tggcccactt tggaccattc acgagcaaga aattagcttc  21600
actgggttaa gccactgaga tgtgggcatt agtttgtgat ctcagcacag tcttacggaa  21660
attgtcattt agccatcaac caacattgac tgagttccta ccatgaactc ctgtgtgacc  21720
tgggtgcctc attctgaatg aggtgctcac tcttggggtt gtgcaagtgc aaggtcagca  21780
gctgagaatg agagcctccc taaatgttat acccgacatg cctctgtcac ctcaccctgg  21840
tcccagccct gtaagtcggt agcgggagcc gggatttgaa gctcggacct gttgacttct  21900
gagcttgtgc ttcctcctgg gaaagcaaag gacagccaca ctcaccctgg gcccttgtgt  21960
gggggctgcg gctgcagcca aaagactcat gggttccctg gatgcttata tccctctggt  22020
gccaaaattg gacagtttga agggagggct gaaccgcagc aaaccaatca gcaaagtggc  22080
agctcccacc gctcctgcca cacccactca tgctgaactg tgtgtgcaag ctccatccct  22140
cacacttcat caccaaacac ccttgatgat gacgcctgct tcctgatctg gccaggcccc  22200
agggccccta ctgcccacac tttcccatcc tcagttatca gacagaaaaa gttccaagaa  22260
aaatccatgc tctgactcag agggccctag gtgggcatag cactctgcct cgttcttgcc  22320
acctccctgc cccgtatggc cctgtcttct tcaccatacg tggcacccat ggcccacctc  22380
acctcctcat tgtcaaggtc tccttgctct gctatggaca tggctgggac cagcgtgtct  22440
ccctccaact ctcttcctca cacctcctca tttctcccgt cttccttctt gcctcagaga  22500
tagaagtggc ttaaaactgt tcctttcagg aacaactaat cagtggccac agaggtcaga  22560
atagcgggta cctggaggac agagggtaga gtcttggaag gggcataagg aaacttctgg  22620
aagtgtagct tgacctgggt gattatcaca tgggtatata cagtcatgta tatacatatg  22680
tcaagagtca aaattagcca aacatgctgc ctcatgccac cagctactca gaaggttgaa  22740
gagggaggat cccttgaacc caggaggctg aggctgcagt gagccatgtt catgccattg  22800
cactctagcc tgggagacag agtgagactc tgtctcaaaa aaaagaaaga aagaaaggaa  22860
agaaagaaag aaagaaagaa agaaagaaag aaagaaagaa agaaagaaag aaagaaagaa  22920
agaaagagtt gtcaagctct acacttcata ttagtgcact ttaagcactt ttctgtatat  22980
acattacctc tcaacttaaa aaacattatc acagagagct ctatggacag tagcagaaat  23040
aaacagcatc aaaaactgaa acttgggtgt tggagtcata tgaacccgca ctgaaaacct  23100
ggctctgttt tctagctgtg tagctttagg caagttactt aacctttctg aacctcactt  23160
ttttcaattg agatgtggat catgaggatt agaaatgctg ctttttataa acagtgctta  23220
gcacaagggc tggatcttgc tgggtgctat acacaattgc ttttattttt attaatatca  23280
gtggcctagg gaggacagga aagtcggagt gacctttcct ggatgcaggc aataacgggt  23340
ggggggccta cagaatttaa agataaaata aaactgatga gaagtcagtc tgcttttatg  23400
atcactgtgc aatggcagat ctaaataatt tcagtggtaa aatactttgt cctgaaaata  23460
ccctttattg atctaagttc taacaattgg tgcagtaact gttggggttt aataatgtat  23520
atgtaaagct tcaaatcagc acatttttat tcttatcctt taataaacat attctacatg  23580
gaagtcaact tgacttggag aactttaaga atcctatagt tgcccccaga gcatgtggtc  23640
```

tcaggaacac acatcagttg agagtaagct cctcacaact ctggaatctt ccaagcttgc 23700
tttgaatgca ttcctgtctc caccgtccag cattcatatt tctgcattta tttttattat 23760
tattttgtgt gtgtgacaga gtctctctct gtcgcccagg ctggagtgca gcggcaagat 23820
gtcggttcac tgccacctcc acctcccggg ttcaagcaat tctcctgcct cagcctcctg 23880
agtacttggg actataggtg tgcacccacc acgtccggct aatttttgta ttttttttt 23940 tagtagggac gggtttcacc atgttggcca ggctggcctt gaactcctga tctcaggtgg 24000
ttctcccact ttggcctccc aaattacaga cgtgagccac cggcccagct gtatttctgt 24060
gtttaaacag tagagtgaaa tcaactatga acgcagaatg atgggaaaga tgacgataag 24120
ggtatttcaa ttttgtcatt ttacgaaact acttggagtt ttgatttgta tttacagttt 24180
ttaaaagagt aaaacagtgt gaactgtgaa tggtaatgat tttgtttggt aagtgcaaat 24240
tttaattcat acatgaaaaa tatttgtttt gtttcatgat tattactgaa aataattttg 24300
tactatgaag gaagaggggt gttaaaaatg atccactgtg gatgtaaatt attctaggca 24360
tgcttctgac taaaacatta gcatttccac aagaatccca aaaaataaaa caaaatttaa 24420
aagatccctt ctgtttcttt tcctccaagt ttccagaccc ccatctccac cctggccacc 24480
tcttcctgcc ataaataatc aaatcccaca ctttcatctt caccttccgt ttccattgcc 24540
tcttccgatg ggacagcacc cgtggggaat ctcctccatg ctcaca 24586

<210> SEQ ID NO 4
<211> LENGTH: 34429
<212> TYPE: DNA
<213> ORGANISM: Homo sapiens

<400> SEQUENCE: 4
gtgatgggag caagcttcct ggatttccga gccttggtca taaagaagct ttgtggtgtc 60
ctttggggcc tcttgaacat tctctctggg aacccaagct tctagaagag accatcatgc 120
taagagagtc cacatatggc cattccagtt gacagtccca ctgagcccag gcttccacca 180
tccctacgaa gacagcaatc atgttagcga agctgtgttg ggccatccag cccagctgcc 240
cactgaaaac caggctttgg tcaatgccat gtgggacaga agaattaccc aagtaagccc 300
agcccaaatt cctgacctat agtattgaga tatgtaatga aatggatgtt attttaagcc 360
attgtgtttt agggggagat tgtcacacag cagtaggtaa caggaatgct tgcttctacc 420
tgccccagcc ctccagcctc tgcaccttag tcacttccat cctgacacct ggaaaaccct 480
ttacccagat cctagactat caaaattctg cattccaaat gggtcagatc caaagggcca 540
ggctgcgtga tgcagttctt ctgtttgccc ctgcaggtgc actctccacc cttctgcacg 600
ctgctctgct cctctgtgtc cggcagccat gctgctgtgg gtgagaccaa tgggctctcc 660
tgccctctgg ctctggttgg gttttgtcaa cagggagcac cagcaggaga acagcagatg 720
agaggagaga ggtcaggata ttcattcccc ctttccctcg gtgcacagtc actgggctga 780
ctgtgtctct ctaccaaggc cacatctcct gtcagtcctc ctggcccacc tctccatacc 840
ctccccattc cagattccct cttgcctatt gattgattga ttgattttga gacagagtct 900
cactctgtcg cccagggtgg agtgcagtgg tgcaatccca gctcactgca acctccacct 960
cctgggctca agcaattctc atgcctcagc ctctggagta gctggaatta caggcaccca 1020
ccactatgcc cggctaattt ttgtattttt agtagaaact tggttttacc atgttggcca 1080
ggctggtctt gaactcctga cctcaaataa tccacccacc ttggcctccc aaagtgttgg 1140
cgttacaggc atgagctacc gtgcctggcc tcctgccgtt ttcttgaaag gcagtggttc 1200
cctttgttac cagagtccca cgccacccgt tgttgctttc cttaaactct cctcgctagg 1260
ttcaggtttc cccagaagca gagcctgaga caaagatttc aatgcaagta gtttatttgg 1320
gaagaggaaa catgggaagg atgtgggtgc gaaacaagac aggaaagggg aagaagctga 1380
catgagcagg tcaccacact gagcacctgg agctctatcc ctgggcagca ctctgggaga 1440
tgatgaatat gttgcaggct taacccagca gaggagcgag gaagctgggg aatctaactg 1500
ccccctcccc tctggcaatg cttccaggac attaacttcc tggcactctt agtttgttca 1560
acatgaccgg ctgagtttct tgcatggcta gaaaatattt gcagcaatga gagagagact 1620
ctgttagcag taagtagcta ttgccatgta gaggtgattt tgagggcata tgggcagcta 1680
caccagccca cacctatgta aataactccc atattaaacc ctcttcaatt actcagtttg 1740
agtgtggcac ctggttcctg ccaggacccc gagtgataca ggctggtctt gagcttcttc 1800
atagcaatac agagtggacc agtgactaca gaaagcttga gaggggctgg agagagatgc 1860
cttccccaat attcattatc cacacagcac gccactcctg tgagaagaca acagagattg 1920
tgtatgtttg agaatgtctc tctacctcca atgtagccct cctgaaaaat ctagttcaag 1980
atctattcca ggccaggcgc agtggctcac acctgtcatc ccaggacttt gggaggccga 2040
ggcgggcgga tcacctgagg tcaggagttt gagaccagcc tggccaacat ggtgaaaccc 2100
catctctact aaaaatacaa aaattagccg ggcatggtgg catgcacccg taatcccagc 2160
tactcgggag gctgaggcat gagaatccct ctgggccaca gagggagact ctgtctcaaa 2220
taaataaata aaaatcaaga tcaaaatgta tatgatcagg agcctcagct ccaccactta 2280
cagctctgtg gctttgggaa agttgttttg agccttgatt ttctcatctg tgtagtgggg 2340
ataacatata catactaatt aataggataa accatagaca cgcctcgctc ataggaggag 2400
aagaacatcc tcacacaatg ggagaggtgg ggattgtgga aaggagagag caaatgcctc 2460
gtcaagatgc tgctgtgctg aaacataaat ccagtgttgc cagatcctcc aatcatccaa 2520
aaaagccgga gacccatctt ttaatgttta aactgtattc aaatgtgtcc taatgtttaa 2580
aactttgtat aagccaaaga aaacatctgt gggccagatt ttgccccaca cagccaaggt 2640
ccctgctgat tctgatcttc taagatctct gaataagaaa gaggacaagg gacaggttgc 2700
cctttcactc acatttatca gacaggatta ggatcagttg cacacaacag aaaacaccca 2760
aataatagtg gctgaaaaaa gacagaagtt tatttctctg ttgtgtaaaa aggccagagg 2820
caggcaatgc cactgatgtg acaactctgt gaagatgcct ccttctatct ctctgctctg 2880
ccatccctag catccagccc ctatcctcat tgtgcagtat ggctgctggg gcaccagcct 2940
tcacatctgc agtccagaga gcagggctga ggaaaggatg cagcagctag tgcttgtctc 3000
tctttttttt tttcttgaga cagagtctca ctcttttgcc caggctggac tgcagtggca 3060
ctatcttggc tcactgcaag ctctgcctcc ggggctcacg ccattctcct gcctcagcct 3120
cccaagtagc tgggactaca ggcgcctgcc accacgcctg gccacttctg tcttttaaag 3180
atctagatac ctggttttcc tcacaacaaa ttctgcttat atagtcacat ggccacatct 3240
aatcgcaaag gaaactagga aatgtcttat acctgtaagg caaggtaccc agctaaaaaa 3300
aaggagattg tgttactaaa gaagaggata gtaggcccac tgcagtggct catgcctgta 3360
atcccaacac tttaggaggt cgaggtgttc gatcacaagg tcaggagttc gagaccagcc 3420
tcacgaacat ggtgaaaccc cgtttctact aaaaatacaa aaattagctg ggcacggtgg 3480
tgcacacctg taatcccagc taattgggag gctgaggcag gagaattgct tgtacctggg 3540
aggcagaggt tgcagtgagc catgattgtg ccactgcatt ccagcctggg tggacagagc 3600
aagactccgt attgggggaa aaaaaaaatt agaggatagt agatctagaa ggctgctcat 3660
ttctgccaca tcaaatagcc tggtaggtga ggagggtata tggataggtg gaaagagtgt 3720
taccaggaag ccagattctg ctgtccatat catatgtctt taagcctctt tctgaccagg 3780
agaagaaaat aagagagcaa gatagaaaga ggcctgagta taatcataga gacaacttac 3840
caaggacctg ttgcatgcca ggcccagcac tgagtcttgt gccaacattg ttttagtcca 3900
ttttgtgctg ctatagcaga atacctggaa ctgggtaatt tttatggaac agaaatgtat 3960
tggctcatgg ttctggaggc tggaaagtcc aatatcaagg tgctggcatc attcaagggc 4020
cttcttgctg catcattcca tggtagaaga tgagagagtc cgagagggta agagagggag 4080
caagagattg atctcacggc ctcaagcctt tttatactca gcattaatcc acccatgagt 4140
gtggagcccc catgacctaa acacctccca tgaggcccca cctgccaaca ctgttgcatt 4200
ggggattaag tttctaacac atgcttgttg gggaaccaca ttcaaaccat agcaaacatc 4260
atctcagatt attcttttca tccagcctat ccggtgggtg ggcctcgtgt tattgtgggg 4320
tggggtcaca tcttgcctgt gccagctggg gtaggaggcc tggacatcca attgtctccc 4380
agattgataa ccaacccacc cttctgtctt ctgccctacc tgacaccact tggtcttcag 4440
agatttctgg tccctccaat ccctgagcct gagattctgc aatttgcttt gtcctaaagg 4500
ctccccgtga gcagccaggt ttcaacttcc tgggtttctt gtcagtcccc actcaccatc 4560
tgccttccag cttccggaat ttggttgatt cttctcatct gctattttct tcctcatacg 4620
ttttctttgt cccagtagat agatgtgcat ttaaaaaaaa aatccctgtg tcattttctt 4680
ggaatttcag agaacaatgg agagaaataa gtgtgttcaa cctgccatgt ttaaacagca 4740
gtctccagcc tcagttcttg actgggggaa tcctcagccc tcaggaggat tgtatggtat 4800
ccccatcctt cccccattcc ttccttatcc tgctccagga gtccatggga gccctcggca 4860
cacaggactc tcttccccac tctctgaacc tggggcatag ttctgtcctg cctccatagc 4920
ccatacctgc ttctcaagag caggggcctt gtcttcttct ctctacttcg acaggtctgg 4980
gcaggcctca ggaagataga tatgagctca tggtgtgggt cattcctaag aagtcacttt 5040
ggactttgag gagttaaaat tcaaagctgg ggatgagagt caggcatttc taaattagaa 5100
tatcaagtgt attcccactg tatttacaat ggaggccagc atcaacactc aaggtgaaag 5160
cctgatagag tcacattggt ccttgaaaac ctcttaggaa gatgccaggt ggagacagag 5220
gcatcgtccc tcactgaatc tgatacagcc agcattttct ccggggcttc ttccccatgt 5280
cttgagtaag tgcctgctgg agatcctggt ttgggttgag aagctgtgtt atgtagacaa 5340
agtgcatctt cagatcctag aatcttcctc agtgggtcat gagcctcatg ttgctcatag 5400
gaaaagaggc caagaactag ggtgaccaac catcctggtt taccaggtct gagtagttta 5460
ttgaaataca gagttttcag tgctaaaacc aaaacagtcc cagggaaatt cccaattgtg 5520
gtcaccctac agaacaaccg taacaacagg attacctctc acacaccctc ctggacatgt 5580
gcatgttaca caatttgtcc actttctgtt gctgtcatag aacccatggg actgggtaat 5640
tgacaaagaa aaggggtttg ttttttacag ttctggaggc tgggaagtcc aagacagggt 5700
ggctggatct ggtcagcttc tggtgagggc ctcgtgctgt gttgtaacac agcagaatgc 5760
atcgtagggt gagaggaagc aagagaaagc cgaggaagca agagaaagcc gaggaagcca 5820
aactcacttt tgtaatgaac tgctctcaat aactcaccca cttctgtgag aattaaccca 5880
ctcctgtgag aaaggcatta atccctccta atgacctaat cccctcttaa aggccccacc 5940
tcccaatacc attacattgg ggaccaagtt tctacatgca ttttggagga gacaaaccac 6000
atccaaacca tagcacacac acaacataaa atcgttatct cctacagttt accacacccc 6060
tcaacctcca cgcccctctc accagccttt tttttaatac gaattcttgc tgttgttggc 6120
ctgggctgga gtgcaatgac acggattcgg ctcactgcaa cctctgcctc ctgggttcca 6180
gcagttctcc tgcctcagcc tcccgagtag ctgagattac aggtgcccgc caccacgccc 6240
acctaatttt tgtattttta atagagatgg ggtttcacca tgttggcagg gtggtctcaa 6300
acttctgacc tcaggtgatc cacccacctc agcctcccaa agtgctggga ttacaggtgt 6360
gagccactgc gcccggcctc accagccctt ttaagggaaa tagatggtag acttgttcgg 6420
agagtgggct ctggaactag gctctggaag cttcagttgc agcattcatt agctgtatgt 6480
gtttgggcaa gtcactttac ctctctctgc ctcagtttcc ttatctataa aattggaaga 6540
ataatagtaa gttctactct gtcaggtcat tgtaaggatt gaatgaatta atattatgga 6600
gagcagttag aacagtgcct gtcatggagg aagctacaca ggtcacaact ccttaactga 6660
aactccagtg tctcaggatc ctgatgcatt ttggaattta gggagttttg ggattttgga 6720
aagcacatga cttatataac acactagtgg gtagtgggat ctggcttagc atcccataac 6780
gaaacacatt aatatttctg cagaaaacaa tatacgagta ttcatacatc tgttcaggtt 6840
aggttttggc tacccaatga gttttggtgt tacattattt tgttcagaaa cactgggatc 6900
tctgaagtgt ggataagggc ttgtaggtct gtgtaaggtt ttgctattat tattgttgaa 6960
tgtgcatctg atataactgc catgcagttg cttcttgagg acaactctga gcttttatgc 7020
ccaaggccct cctggactct tggagttttc tagcagggcc ttcctgcacc aagagctctg 7080
aataaccttt gaaggctgac aggacactct cttcttctct ctctacctag gtcctcaatt 7140
tagtgatgtc tccctgttcc tctcagtgtg gtaatagagg ttggcagggg aggggtaggt 7200
tgcaaatgca atctccagga gccttcccca gcctgaccct caccccctca accccagctg 7260
gtcccagtgg gggaggggca caggttgtgt ggaagtgatg agtaagcccc tcttctggtg 7320
aagctattgt gggttcaggc aatcgtctgg cctgcacagg caagataatg gagtcaaagg 7380
aggcttatgg cccctcagcc gcccctgggc atgcacagat gtctctatgg cacacactag 7440
cacttgcaga aaagcattgg tgccaggtgc ggtggctcat gcctgtaatt ccagcacttt 7500
gggaggccaa ggcgggtgga tcacttgagg ttaaaagttc gagaccagcc tggtcaacat 7560
gcaaaacccc gtctctacta aaaatacaaa aattagccgg atgtggtgac gggcacctgt 7620
aatcccaact actcgggagg ctgaagcagg agaatcactt gaatctggga ggtggaggtt 7680
gcagtgagcc gagatcgcgc cactgcactc cagcctgggc gacagagtga gactctgtct 7740
caaaaaaaag aaaagaaaag tgttggaggg gaacgagaaa gttcccctt aattctcagc 7800 cagtatttac tgagtgtgac cctgggctgg gccccaggct aggtgctggg gacacacagt 7860
gaggaaaacc tggcccctct gagataaacc cacaggccag gggcagctgc cttctgacat 7920
tgggggtatg gggctggccc tcaccctgac catggtggca ggtgcccacc cacccttcaa 7980
agcaagagga gggagggaga agtgcctgta tgttcaagag ttactttaca aggacaaatg 8040
ggtccatcac cttggttgac gtcagcaaag aagcatcagc caaagccttg aggtgacccc 8100
aaaagactgg ggtgcaggtt agggggttga gacaggctca gcatggagag aggagggtaa 8160
agctcctgca gaggccccag ctcccaaaga tgaagctacc gcttgatgat gctgtctcca 8220
gggccagaga tcttcctctc atcccgcact atctgcagtc ctctctggtg tgtgtggggc 8280

```
gcagtcatta gacccatctt ccaggtgaga gatctctgcc tcagggctca gaggacctcc   8340
tcctggggtt tcagatcagt cttccaggat ggaggatggg aagcaggcca tcaagagttc   8400
tggtaagaaa tgaggtttct agtcaggtac ggtggctgac gcctgtaatc caagtacttt   8460
gggaggccga ggcaggagga tcacttgagg tcaggagttc cagaccagcc tggccaacat   8520
ggtgaaatcc catctctact caaaatacaa aaattagcca ggagtggtga agtgcacctg   8580
tagtcccagc tatttgggag gctgaggcag cagaatcgct tgaacccaga aggcggaggt   8640
tgcagtcaac tgagatcgca cactgcagtc tagcctgggt gacagaggga gactctgtct   8700
caaaaaaaaa aaaaaagaaa gaaagaaaga aatgaggttt ccctgactga gtctgggaag   8760
ctggcattca ttcgttcttt cactcattca ttctggctga tcccgagctc tgacagttcc   8820
tatctgcatg accctggcag ctcacctcag ccctgagcct aagattctac tatgtaccag   8880
gcactcttca gtctacttag gatacagaag gagccaggta gtcatgacct ccagcctcat   8940
gacgcagata atggggtggg ggtaggggca actagcttat tctggaggct tcctgtaaaa   9000
aacaacgctt aagtggaggt ggacagaatc tccccatcac gctggggaaa ggcagaaatg   9060
gatttagcaa acttactgtg aaagtcacag cttaagcctt agagcccctc acttgccagg   9120
ggccttccag gggcctggga ggggccaagt aatgcacact caggatcaca tgctttagta   9180
gaatttgcca atgtaagatg ttttaactgt aatttattaa gactgctgcc cctctcactc   9240
caacttccct ctctgtcata cttccccttc ttttgggtat tgccccagtg cttctggcat   9300
tttgggggat ctagctaagg agaagttgtc acggaatact gacattgatg aaaataacaa   9360
aagtcaaaat acaccactac aaaaaggatg taatagaaag catcaattca aaaaaatttt   9420
aagattagtc atcaaggaaa cataataagt ccggaaatct tacagctccg atatgaaaga   9480
aacttgatag aggttcttcc aaatttgaca acaatcctag aattttatga ccttccagta   9540
gtcccccctt atcctcgagg gatacatttc aagaccctca gtgggtgcct gaaaccgtgg   9600
atagtacgga atcctattta gactatgttt tttttgatcc aatagccaag acaactacta   9660
agttgacgaa tgggcaggta gtgaagatgc tggacaaagg ggcaattcac acccctggtg   9720
ggacagggtg gggtagagtg gggcagcacc aaatttcatt acgctactcg gaacagcatg   9780
caatgtagaa cttaatgaat tgttgatttc tggaattttt catttaatat tgtcagactg   9840
tggttgtcca tgggcaactg aaacctcagg aagcaaaacc ttgcagaaga gggggctact   9900
gtaccagtaa taagttgcaa agctgaaaga aactttatcg accataagaa atttggggcc   9960
aggcacagtg gctcatgcct gtaatccccg tattttggga ggccaaggtg ggagggtggc  10020
ttgaggccag gagttcaaga ccaatctggg caacatagtg agactccatc tctacaaaat  10080
cttaaagtat tagttgcatg tggagacaca tgcctgtagt cctgattact tgggaggctg  10140
agacggggag atcctttgag cccaagagtt tgaggctgca gtgtacaaag atcagacaac  10200
tgcatgcctg cctgggcaat ggagcaagac cctgccttaa aaaaaaaaaa aatgggggcc  10260
gggcacggtg gctcacacct gtaatcccag cactttgaga ggccaaggtg ggtgaatcat  10320
ttgagaccag gagtttgaga ccagcttggc caacatggtg aaaccctatc tctactaaaa  10380
ttacaaaaat tcgccaggcg tgcctgtagt cctagctact caggaggctg aggcaggaga  10440
atcgcttgaa cccaggaggt ggaggttgca gtgagcctag attgcaccac tacactccag  10500
cctgggcgac agagcaagac tctgtctcaa aaaaaaaaaa aaaaaagaaa aaaaaattag  10560
tcaactgtgc tagagaaaag attaaagtat cttcttattc tctctaaaga aatgacatt   10620
```

acaaaatcaa tgtcacatga agaggttaac gtaaaagtat acaaacacaa tgtaggaatg 10680
aaataattat agatatgtat catattgatg aaaatatgaa tgtaaatgta aattttaatt 10740
tatgtaatta tgaacaaaaa tgtaatgcta ttatgtaaat aaatatattt attatgttac 10800
atgtaactta acatgtttaa taacttatta tgttatgaac tgttgctgac tatgtggcca 10860
caacagggga gggaatcttg ggacccttat tcagagagat caagaccaaa taaaggacct 10920
aataagtcat ttccttcaac ctgtcaccag tgcaggaatc ctcttcctga tgacagctgt 10980
ccactgagcc tcggctctgt acatttcctg ggatgaggaa ttcacccctc ctccaaatcc 11040
tgtactatct tgggtcaaaa ctctggttgt gggaagttct ttagtcaagc tgatcactag 11100
ctgtcggtgg tttccccttg ggtcctcatc ttccccagca cccccagaaa tcatgggctg 11160
ctgcttccca ttttattata gctctgcagt gctacaatgc agctctagta tcttgccctg 11220
gcctgggata acctgccctt cttcaaagtt tccttttatg tcttgacttc caaagtcttc 11280
ctcatccatg atcgcagaga ttgatcagcc actcatacat atatgaggac gacaatgatg 11340
atgatgataa tgagaacagc tagccagcac tgagtgctta ctgtgtactg ggctccgtgc 11400
tgggtgctgt atgagcacct gctgttggtc tcatgcacac ctatttatgt tggttttgag 11460
taacttgtgc aggtatacct ttgatttaaa attttggttt ctatttagac tacgatagga 11520
atttttgttt tgtttagcct tctctcctaa gcttaatgaa accacatatt cagaaagaaa 11580
ggacacattt aattaaaaca tttcaaagac acacagctta aaagagtgat taccctagac 11640
ctcttacaaa caaatatgcc cctcctccaa aactcttctt aatgtaaatt tcagagagga 11700
aaagccaaaa acaaaaacaa aatcgagaat gtgtgttaat ttatctggct aaaacctgat 11760
aaaaagattt tcttggccgg gcgcggtggc tcacgcctgt aatcccagca ctttgggagg 11820
ccgaggcgag cggatcacga ggtcaggaga tcgagaccat cccggctaaa acggtgaaac 11880
cccgtctcta ctaaaaatac aaaaaattag ccgggcgtag tggcgggcgc ctgtagtccc 11940
agctacttgg gaggctgagg caggagaatg gcgtgaaccc gggaggcgga gcttgcagtg 12000
agccgagatc ccgccactgc actccagcct gggcgacaga gcgagactcc gtctcaaaaa 12060
aaaaaaaaaa aaaaaaaaaa aaagattttc ttaagagctc tgtagttcaa agtcaactta 12120
attaaaagca ggtattaaga ctataatttt taaaatagag cctttctgct tcttctattt 12180
tggatcttgt tttggggaat ttttttcag gtgactgaaa cccctctttt aattatatgg 12240
tgagtccctc tctctgttcg cttcctttct tgttggtgtg attttttgct gaaggaaaaa 12300
aaaaatgtaa aacttaagca gctttctgga aagcttaaat ttattctctg tgctttgaaa 12360
tgtaaatttc ctaccttgtc taaaattcag tgaggtactc gcttcgcagc acatatacta 12420
aaactggaat gaaggccggg tgcagtgact cacgcctgta attccagcac tttgggagtc 12480
tgaggcgggt ggatcacctg aggtcaggag ttcgagacca gcctggccaa catggtgaaa 12540
ccccatccat actaaacata aaaaaattag ctgggcgtgg tggcacatgc ctgtaatcct 12600
ggctacttgg gaggctgagg caggggaatt gcttgaatct gggaggtgga cgttgcagtg 12660
agccaagact gcaccactgc actccagcct gggtgacaga gagagactct gtctcaaaat 12720
aaataaataa acaaataaat aaataaaatg aaattggaat gatagagaaa agattagtag 12780
catgtcacct gtgcaaggat gaaatgtaaa ttctgaagcg ttccattaaa aaaaatatgt 12840
tatttaataa aattaattaa ggccaggtgt gatggctcac acctgtaatc ccaacactgg 12900
gaagctgagg tcaggaattc aagagcagcc tggccaacac ggtgaaccta gtctctattg 12960
aaaatgcaaa aattagctgg gcatggtggt acacgcctgt aagcccagct actttggagg 13020
ctgaggcagg agaatagctt gaatccagga ggtgggaggc tgcagtgagc cgagattgtg 13080
ccactgaact ccagcttggg caacagagca agactctgtc tcaaaaacaa acaaacaaaa 13140
aaatgaaaaa aaaataagtc acaaagggat caaacttcat tttggctact cctgctttgg 13200
cgatggccac aaaagggaaa aagtttttca aatttttttg gtaactatgc ctttagagtt 13260
ttgccaagct aaattaaact atgaatattt attgaagatc tagatcattt ccaaataaga 13320
tataatgcta agacattaat tactacatat aagtttaagc tcatatactt ttggtttctt 13380
atttcagaga aacaaaagat atttaggggc tgggtgtggt ggctcatacc tgtaatccca 13440
gcactttgga aagctgagat aagaggactg cttgaggcca ggagttacag accagccagg 13500
gcaacatagt gagaccttgt ctctacaaaa taaaaatttt aaagttagcc aggagtggtg 13560
ttgcatgctt gttagtccta actactcaag aggctgaggc aggaggatcg atcactcaag 13620
cctaggagtt tgaggctgca gtgagctata atcacaccac tatattccag cttgggcaac 13680
agagcaagac cctgtctcaa aaaaaaaaaa aaaagagata ttaagatccg ctagtaaaag 13740
tatcctattc cacactgaaa aattgttcca ttagaaagcc tgtgtttcta aatattataa 13800
aatgtgtatt aatcaattgt tagtacatag tgacaaaatt acttctggct gggcggtggc 13860
tcacacctgt aatcctagca ctctgggagg ctgaggtggg cagatcacct gaggttagga 13920
gtttgagacc agactggcca acatggtgaa accctgtctc tactaaaaat acaaaaaatt 13980
agccaggcgt ggtggtgtgt gcctgtagtc ccagctactt gggaggctga ggcagaagaa 14040
tcacttgaac ctgggaggtg gaggttgcag tgagctgaga tcgcgccact gcactgcagc 14100
ctgggtgaca gagtgagact ctaaaaaaaa aaaaaaaatt acttcttaga ttttcagtat 14160
aaattaagat tactaagatt taaaattctg actaatatat ggtaactaac actagagacc 14220
agaaggaaga caattctgta ttcagaatat gtaaggaaag taagacatct ttttaggaag 14280
gaagattata agaaagacat aagcatgtgg tttttgttaa agagaaagtg gttttgccta 14340
gtttagaggt tatttaaagg ctgtatgaaa ttgggataaa agaaggaaag aataaaatag 14400
attaactgaa tggatataga aagttgggaa aagaaagagg aatggaaaaa ttgtaagaag 14460
ttataaaagg tttatagaaa tattatctcg tgtggtcaaa gctgattgag attagatgat 14520
ttataaggtt ttattaaaat taggctttat atttataatg cattgatgca aaagtagaat 14580
catttttcta ttttgaacta gatagtcaca tagttttttt tttgttcttt ttttttttt 14640
tttttgagat ggagtctcgt tctgtcacct aggctggagt gcagtggcgt gatctcggct 14700
cactgtgacc tccacctcct ggattcaagt gattctcctg cctcagcctc ctgagtggct 14760
gggattattg gcatgcgcct ccatgccagg ctaatttttg tattttgagt agagaaaagg 14820
ttttgccatg ttaaccaggc tagtcttgaa ctcctgatct cagggtgatc cgcctgcctt 14880
ggccttccaa agtgctggga ttgcaagcgg gagccaccgc accctgcctc atatagtatt 14940
aataagagat agcaaaagat ttttttgttt accttttgag taaactgctg ctaaaaaaaa 15000
aaaaaaggag aaaagaaacg ggggagaggg agagacattc tgttggtctc aagttgtctt 15060
tttcaggtct tttgtgtcag gcctctgagc ccaagctaag ccgtcatatc ccctgtgacc 15120
tgcatgtata catccagatg gcctgaagca actgaagatc cacaaaagaa gtgaaaatag 15180
ccttaactga tgacctttca ccattgtgat ttgtttctgc ccccacccta ctgatcaatg 15240
tactttataa tctcccccca cttaagaaag ttctttgtaa tctcccccac ccttaagaaa 15300
gttctttgta attctcccca cccttgagaa tgtactttgt gagatccacc cgctgcccac 15360

```
aaaacattgc tcctaactcc actgcctatc ccaaaacctg taagaactaa tgataatccc  15420
accacccttt gctgactctc ttttcggact cagcccgcct gcatccaggt gaaataaaca  15480
gccttgttgc tcacacaaag cctgtttggt ggtctcttca cacagatgcg tgtgacattt  15540
ggtgctgaag acccgggtca gagggactcc ttcgggagac cagtcccctg tcctcaccct  15600
cactccgtga agagatccac ttacgacctc gggtcctcag atcaaccagc ccaaggaaca  15660
tctcaccaat ttcaaattgg gtaagtggtc ttttcactct cttctccagc ctctcttgct  15720
acccttcaat ctctctgtcc ttccaattcc agttcttttt cctctccagt agagacaaag  15780
gagacacatt ttatccgtga acccaaaact ccagggccgg tcacagactc aggaagacag  15840
tcttcccttg ccatttaatc actgcgggga cgcctgcctg attattcacc cacattccat  15900
tggtgtccga tcaccgcagg gacgcctgct ttggtcattc acccacattc ccttggtggc  15960
aagtcaattg cggggacgcc tgctttggct gctcacccac attgcagccc agggctgctc  16020
cccacccccct tctccatatc tctacccttc tctttaaact tgcctccttc actatgggca  16080
aacttccacc ctccattcct ccttcttctc ccttagccta tgttctcaag aacttaaaac  16140
ctcttcaact ctcacctgac ctaaaatcta agcatcttat tttcttctgc aacaccactt  16200
ggccccaata caaactaaca atggttctaa atggccagaa aatggcactt ttcatttctc  16260
cgtcctacaa gacctagata atttttgttg aaaaatgggc aaatggtctg aggtgtctta  16320
cgtccaggca tttttcacac ttcgttccct ccctagtctc tgttcccaat gcgactcgtc  16380
ccaaatcctc cttctttccc tcccacctgt cccttcagtc ccaaccccaa gcgtcgctga  16440
gtcttgtgaa tcttcctttt ctactgaacc atctgacgtc tcaccttctt cccagactgc  16500
tcctcctcag ctcgctcccc accaggctga atcagcctcc aactcttctt cagcctctgc  16560
tcccacatcc tataaccctt ctattacccg ccctccccac acccagtctg gttttcagtt  16620
tcgttctgcg gctagctctc ccccacctgc ccaacaattt cctcttagag aggtggctgg  16680
agctgaaggc atagtcaggg tacatgtgcc tttttctcta tcagaccttt cccaaatcag  16740
ccagcattta ggctctttct catcagaccc cactaaatat atacaggaat cccgatatct  16800
aactctgtcc tacagtttaa cctggagtga ctgaaatgtc atcctgactt ctaccctctc  16860
cccagatgaa cgggaaagag ttttttctct agcccaatct cacgctgata accgccggct  16920
tcatgaacct gacctccagg aaggcagtag agcagttccc cgagaggacc cccaatggaa  16980
ctatcaggca gattccccag gtatggctag gcgagattac atggtttcct gcctagttga  17040
agggcttaaa aaggcagctt acaaagctgt taattatgac aaacttagag aaactaccca  17100
aggtaaagac gaaaacccag ctcagttcat ggcccgctcg gcagcaaccc ttacacactt  17160
taccgcccta gacccagagg ggccagaagg ccgccttatt cttaatatgc attttatcac  17220
ccagctcctg acattagaaa aaagctttaa aaattggaat ccggccctca aaccccacaa  17280
cacgaattaa tcaacctccc cttcaaagtg tacaataata cagaggaggt agccaggcag  17340
caacgcattt ctgagttaca gctgctcgcc tccgctgtaa gacagcccac aaccacgtct  17400
ccagcataca agaacttcag aacatccaag ccacagctcc caggggctcc ttcaaaacat  17460
cctcgtggac cttgcttcaa atgctaaaag cctggccact gggcctcaga atgcccgcag  17520
cccgggattc ctcctaagcc gtgccctgtc tgtgcgggcc cccgctggag gtcggactgt  17580
ccgactcaca tcactgccac tcctaaagcc cctggagccc aaaccctatg ttccttggcc  17640
gactccttcc cagatctcct cggcttagca gctgaagact gacgtagccc gatcgcctca  17700
gaagcctcct ggaccatcac agacgctgag cttcgggtaa ctcttaaagt ggagggtaag  17760
```

tccatcccgt ttaatcgata tgggggctac ccactccaca ttatcttctt ttcaagggcc 17820
tgtttccctc gcccccataa ctgttgtggg tattgatggc caagcttcaa aaccccttaa 17880
aactccccca ctctggtgcc aacttggaca acgttctttt atgcactctt tttcagttat 17940
ccccacctgc ccagcttcct tattaggctg agacatttta accaaattat ctgcttccct 18000
gattattcct gtactacagc cacatctcat tgccccccttc ttcccaaccc aaagcctcct 18060
ttgggtcttc ctctcatatc ccccgacctt aacccacaaa tatgggacac ctccactccc 18120
tccctggcaa ccaatcacat gcccattact atcccattaa aacctaatca cgcttacccc 18180
actcaatgcc agtatcacat cccacaacag gctttaaggg gattaaatcc tgttatcact 18240
tgcctgctac agcatgggct tctaaaacct ataaactctc cttacaattc tcccatttta 18300
cctgttcaaa aaccggacaa gtcttacagg ttagttcagg atctgtgcct tatcaaccaa 18360
attgttttgc ctatccaccc tgtggtgccc aacccgtacg ctcttttgtc ctcaatatct 18420
tcctccacaa ctcactattc cattcttgat ctttaaaatg ctttttttca ctattctcct 18480
acacccccttg tcccagcctc tctttgcttt tacctggacc gatcctgaca cccatcagtc 18540
ccagcagctt acctgggctg tactgccgca aggcttcagg gccagccctc attacttcag 18600
ccaagctctt tcttatgatt tactttcttt ccacccctct gcttcttgcc ttattcaata 18660
tattgatgac cttctacttt gtagcccctc ctttgaatct tctcaacaag acaccctcct 18720
gctccttcaa catttattct ccaagggata ttgggtatcc ctgtccaaag ctcaaatttc 18780
ttctccatcc attacctacc tcagcataat tcttcataac aacacatgcg ctctccctgc 18840
ggatcgtgtc cgactgatct ctcaaacccc aggcccttct acaaaaacaac aactccttta 18900
cttcctgggc gtggttggat acttttgtct ttggatacct ggttttgcca tcctaacaaa 18960
accattgtat aaactcacaa aaggaaacct agctgactcc atagattctc aatcctttcc 19020
ccactcctct ttctgttcct tgaagacagt tttagagact gctcccacac tagctctccc 19080
tggctcatct caaccctttt cattacacgc agccgaagtg tagggctgtg cagttggaat 19140
tcgtacacaa ggactgggac cgcaccctat aggctttttg tccaaacaac ttgaccttac 19200
tgttttaggc tggctatcat gtctccatgc ggtggccgct gctgccctaa tacttttgga 19260
ggccctcaaa atcacaaact atgctcaact cactctctac agttcttata acttccaaaa 19320
tctattttct tcctcacacc tgacacatat actgtctgct ccccggctcc ttcagctgta 19380
ctcactcttt gttgagtctc ccacagttac cattgttcct ggcccggact tcaatccagc 19440
ctcccacatt attcctgata ccacacgtga cccccatgac tgtatctcta tgatacacct 19500
gacattcact ctatttcccc acatttcctt ctttcctgtt cctcaccctg atcacacctg 19560
gtatattgat ggcagttcca ctaggcctaa tcgccacaca ccagcaaagg caggctatgc 19620
tatagtatct tccacatcta tcattgaggc taccactctg cccacctcca ctacctctca 19680
gcaagctgaa ctcattgcct taactcgagc cctcactctt gcaaaggaac tacgcactac 19740
gcatcaatat ttatactgac tctaaatatg ccttccatat cctgcaccac catggtgtta 19800
aatgggctga aagaggtttc ctcactacgc aagggtcctc catcattatt gcctctttaa 19860
taaaaactct tctcaaggcc gctttacttc caaaggaaac tggagtcata cactgcaagg 19920
gccaccaaaa ggcatcagat cccatcgttc agggcaacgc ttatgctgat aaggtagcta 19980
aagaaagagc tagcattcca acttctgtcc ctcacagaca gtttttctcc tcctcatggg 20040
tcactcccac ctactctcct gctgaaactt ccacctatca atatcttccc acacaaggca 20100

```
aatggttctt ggaccaagaa aaatatctcc ttccagcctc acaggcccat tctattctgt  20160
catcatttca taacctcttc catgtaggtt acaagccgct agcccgactc ttagaacctc  20220
tcatttcctt tccatcatgg aaatctatcc tcaaggaaat cacttctcag tgttccatct  20280
gctattctac tactcctcag ggattgttca ggccccctcc cttccctaca catccagctt  20340
ggggatttgc ccctgcccag gactggcaaa ttgactttac tcacatgtcc cgagtcagga  20400
aactaaaata cctcttggtc taggtagaca ctttcactgg atgggtagag gcctttccca  20460
cagggtctga gaaggccatc atggtcattt cttcccttct gtcagacata attcctcagt  20520
ttggccttcc cacctctata cagtctgata acggattggc ctttattagt caaatcaccc  20580
aagccgtttc tcaggctctt ggtattcagt agaaacttca taccccttac cgtcctcaat  20640
cttcaggaaa gatggaacgg actaatggtc ttttcaagac acacctcacc aagctcagcc  20700
tccaacttaa aaaggaggac tctgtcaagg atacagccca aaaactcaac aaccaagcaa  20760
gtaattacgc tgaacagcct tgggcactct ctaattggat gtcctgggtc ctcccacttc  20820
ttagtccttt aatacctatt tctctccttt tattcagacc ttgtgtcttt catttagttt  20880
ctcaattcac acaaaaccgc atccaggcca tcaccaataa ttctgtatga caaatgctcc  20940
ttctaacaac cccacaatac caccccttac cccaaaatct ttcttcagtt gaatctctcc  21000
cactgtaggt tcccatgctg ccccaatccc actcgaagca gccctgagaa acattgccca  21060
ttatctctcc ataccagccc caaaattttt cgccactcca acacttcacc actattttgt  21120
tttgcttttc ttattaatat aagaagacag gaatgtcagg cctctgagcc caagctaagc  21180
catcatatcc cctgtgacct gcctgtatac atccagatgg cctgaagcaa ctgaagatcc  21240
acaaaagaag tgaaaatagc cttaactgat gactttccac cattgtgatt tgtttctgcc  21300
ccaccctaac tgatcaatgt attttataat ctcccccacc cttaagaagg ttctttgtaa  21360
cccccccccc gacccttaag aaggttcttt gtaattctcc ccacccttga gaatgtactt  21420
tgtgagatcc aacccctgcc tgcaaaacat tgctcctaac tccaccgcct atcccaaaac  21480
ctataagaac taataataaa cccaccaccc tttgctgact ctcttttcgg actcagcccg  21540
cctgcaccca ggtgaaataa acagctttgt tgctcacaca aagcctgttt ggtggtctct  21600
tcacacagac gcacgtgaca ttttgattgt ttggaaaatt cagtctcctc tctatgaaag  21660
agtaaaagtt tgctttttga aatatttgaa tcatcacttt ggctagatga atgactacaa  21720
ttttaaactc actttgccaa cacactgaca ttggcagagt gcaaagatgg caagaggctg  21780
ggtccatggt gacactgtta gggaaacagg agcataacag agtcagggtg acaccatttt  21840
aaaatcaatt gtggctgggc acagtggctc atgcctgtaa tcccagcact ttgggaggct  21900
gaggtgggcg gatcacctga ggtcaggagt tcaaagccag cctggccaac atggagaaac  21960
cccatctcta ttaaaagtac aacaattagt tgggcatgat ggtgggcacc tgtaatccca  22020
gctacttgag aggctgaggc aggagaattg cttgagcccg ggaggcagag tttgcagtga  22080
gctgagatcg tgtcactgca ctccagcttg ggtgacagtg tgacactctg tctcaaaaaa  22140
taaaataaaa taataaaata ataaaatcaa ctgcatcttc aaactagcaa ggcacattcc  22200
ttggcagtca caactcatgg ccatgatatg ttttgggtga aggaagcgat ttagtaatgc  22260
ctgcaagggc aaactcctat ggtggcaggg tgtccagata tcctaatagc acataacaat  22320
atctgctttt gagataggta aagtcatgct ttgaagtatt tcctcactaa aataccaagg  22380
ataattttat ttaaatcaac aaagcactaa attttctttt ttcttttttg agatgctcac  22440
tctgtcgccc aggctggagt gcagtggcac gatctcggct cactgcaagc tccacctcct  22500
```

gggttcacgc cattctcctg cttcagcctc ccaagtagct gggactatag gcgcctgaca 22560
ccatgcctgg ctaatttttt gtatttttag tagagacggg gtttcaccat gttagccagg 22620
atggtcttga tctcctgacc tcgtgatcca cccgccttgg cctcccaaag tgctgggatt 22680
acaggtgtga gccaccacac ccggcctaaa ttttctttaa aaaaaaaaaa ttattgtatt 22740
tatggctggg cactgtggct catgcctgta attttagcac tttgggagac tgaggcaggc 22800
ggatcacttg aggccaggag tttgagacca gcctgggcaa catggcaaaa tcccatccct 22860
aataaaaata caaaaaaaaa ttagctgagc atggtggcac atgcctgtag tcccagctac 22920
ttgggaggct gaggtgggag gatcacttga acccgggagg cagaggttgc agtgagccaa 22980
ggtcgtgcca ctactctcca gcctgcacaa cagaaaggac tccatctcca aaaaaaaaaa 23040
aaaaaaaagt atttatttat ttttcattta ttccaggcag aagaaacagc aaatgcatag 23100
gtcctgaggc aggcatgcat ttggcatgtt ggaaaacatg tggcactggc cagaccaagc 23160
aaggccttgg agaacatgaa gagcagtctg gcttttgctc cagttgccac agaagtcact 23220
ggaagaggcc tcctctgaga taagacacta agaaagcagt gtcaggccag ttagacaggt 23280
ctggacttgt cttctggagt caaatgcagg cggcagacat ttaaatggcc agtcacagag 23340
agggtgatgg gggccatgat gggtgaccca cagggccgtg agagcacaga ggagggaccc 23400
tgccccatcc tgagggccca agggtccttc ccaggggaag agagagctca gctgagacct 23460
gaaggctgca gcagagttag ccagcttgaa agagaacgac aagggatggg atgggaagtg 23520
gattccaggc agaggaagaa gcaactgcaa acgcctgaga agagaaagcc tggagcattt 23580
gggggaccag aagggggtta atgtggctgg attgtagatg caaacagggg ttggcctggg 23640
gggcaggcgg cagcggctag gagggctctg cttttctcac ttgatatact gtgaacattt 23700
ttctatgtca gaaaggatcc ttctgctata ggatttttaa gggctgagca ttacgtcgtg 23760
gaataactgg ttctccagtg tcagacattt aggttctttc tagtttttcc ctcttagaaa 23820
caatgctatg ttgaacatct ttgtctgtgc atctttgtgc acacgtatta ttatttctgt 23880
gcggtaaagt tgggaagtct cggaggctac ttggtggaca ggattgagag ctgccttgga 23940
gaggcctgag tcagatctgt ttgccagatc agcctccact gggtttctac tggaggggcc 24000
atacacaggg agatgcaggg agaaggcctg agggagagat agagagccct gattgtgagc 24060
tgtggctgcc caggccagat aatggcaggg gagagaggag gccccgatcc tgggcccctg 24120
tctgtgctgt cggcctggtg cgttagctcc tggtgccttc taaagaggca acaaaagtac 24180
ttcaaattga gcatgagctt gggttcaaat cacacctcta ccgctaaaaa actaagtgcc 24240
gttgggccag ttacttagtc attctgaatc tcagcgtcct tatctgtaaa atggggaaaa 24300
taagccaata gggttattgt gaaagataca tgagattaat gagtcttggc gatagtccct 24360
gctcccagta aatgacggcg tgcattttta ttgtcatctt gggtctccat cctttttaaa 24420
aaaatacttg attataacag ctttattgag ataaaattca catgccatac aattcaccca 24480
tttaaagtgt acaattcagg cagggtgtgg tggctcatgc ctgtaatcct ggcactttgg 24540
gaggccgagg cgggcagatc acttgaggtc aggagttcga gaccagcctg gccaacatgg 24600
tgaaacccca tctctacaaa aaatacacaa attagctggg catggtggtg ggcgcctgta 24660
atcccagcta ctcgggagac tgcggcagga ggatcgcttg aacccgggag atggaggttg 24720
cagtgagcca aggtcatgcc actacactct agcctgggca acagagcaag actctgtctc 24780
aaaaacaaca acaacagata aagtgtacaa ttcaatagtt ttttatatat ttgtcacaat 24840
caattttggc actttttcat tatcccccac agaaaccctg tacctatcag cagtcagtcc 24900
tgcagccgac ccccctctgg ccccaggtaa ctgccaatta ctttctgtct ctatggattt 24960
gctctttcta gatgtttcat agaaaagaag tcatgcaaca tggggtcttt ttttttttct 25020
tttgagacag ggtctccttc tcttgcccag gctggagtgc aacagtgcaa tcacagctca 25080
ctgcagcctc gaactccagg gctcacatga ccctccctgc tcagcctccc aagtagctgg 25140
gaccacagtg caccgccatg cccagcaaat ttttaaaaaa ttgtttgtag agatgggttc 25200
tccctatgtt gcccaggcta gtctagaact cctgggctca agtgatcctc ccaccctggc 25260
ctcccaaagt gctgggatta caggcatgag ccagtgcgtc caggcctgtg gtcttttatg 25320
actggctttg ttcacttttt tcatccctgt cagcaatgta tgagagttct gatttctctg 25380
attccttacc aacacttatt attgtttgtc ttttttattg tagccatcct cgtgggggtg 25440
tgtagtggga tctcattgtg gctttgattt gcatggcctt gacggttaat gtttctggtt 25500
tttttcagtg gaatcccctt tataaattct gggacaccct attcccagtg tggaaacact 25560
aacctgttcc aaagaaagaa aaaaaattct agatggaaaa agatgttcat tactgcgaca 25620
taacatttct taatacaagt gactcgtcta tagcagtagg tagttcctaa tttttttttt 25680
tttttgagac agagtcttac tttgtcacag gctggagtgc agtggcatga tctcagctca 25740
ctgcaacctc tgcctcccgg gttcaagtga ttctcctccc tcagcctccc aagtagctgg 25800
gactacagga acataccacc actcccggct aatttttgta tttttagtag agatggggtt 25860
tcacaatgtg gaaacactag gccacattgt gaaatgtggc caggatggcc tccatctcct 25920
gacctcatga tctgcccacc tcggcctccc aaagtgctgg gattacaggc gtgagccacc 25980
gcgcctggcc tattatcttt aataattata aatactgggc tgggcgtggt ggctcatgcc 26040
tgtaatctca gcactttggg aagccaaggt gggcagatca ctggaggtca ggagttcaag 26100
accagcctgg ccaacatggt gaaaactcat ctctattaaa aatacaaaaa ttaccctgtc 26160
atggtggtgc atgcctgtaa tcccagctac tcagaaggct taggcaggac aatcgcttaa 26220
acctgggagg cggaggttgc agtgagccga gattgagcca ctgcactccg gcccaggcga 26280
gagagtcaga ctccatctca aaataataat aataattata ataactataa agaccagcta 26340
tcatatggaa aatgtccctg atgtgtgaac aaatgcagga tggaaaaata ctcagtgtag 26400
tcattttagc taatatatat ttgttaaaac atccaaatat ttttttcgag ctcggcgctg 26460
tgtgccaagc tccatgctgg ctcatggaca aagtcaggaa aagaacaagc aaaaatgaaa 26520
ttccttcttg tgtcgggagt ggtggggttt tgggggacag gtatctcccc ttccccatgt 26580
tttcttctca aacttcctcc actgttgtta tattaccttt gcagtgataa aaccaagaga 26640
acagaagaaa tacttctgga cctaaggatg aaagaatgat gggagaaaca tttcttgagc 26700
cagtcccttt ctgcgttctt attttgtgga atccgcacac atccccgaga agcttaataa 26760
aaagggctac tatcatgaca cttactgtgt gccttgccgg ttccacctgt taggtgccat 26820
tgttgtcccc attttacaga tgaggaaact gaggcggggc aaggagatgc ccttctgctt 26880
ggtggtctat ccttcagcat tacccacaca catgcagagc tacatataag ctcacgttca 26940
cactcggatt cacgtctgca cccatgggca catggaggat cgcacaagcc acactcagac 27000
acacatgtgt gctcacacac agggctgccc atgtccacag gtatgtgcat ggggacacgc 27060
atgtatatat gtgcatattc ccatatgcac acagcacagg tcaaacactt ttggacacac 27120
atctgcctga gaatgggaaa aggggtgcaa gataaagggg caaagtctgg cttttgcctc 27180
ctccctgcac ctgctaccag ctgtgtgcag gactgggtgg ggcagaaata ggtggctctg 27240
agctcagagg gcagaggtgg ccttgcacta gaaatccacc tgccaaactt ccaaatgggc 27300
tacagcgact aaggggcctc acctgctggg caaatccccc agctggaggg tgtgctccag 27360
atcctccagg ggtccccagg gggttgagaa gatgaggggc acacccagca gcccctaagg 27420
gaggaagcgt ggccatactg gctaaggggg cgcactcttc ttgcaggccg cctgatcaga 27480
tgcctgtaaa ataagacagc tttacaaaga gggtgtcgga atgtgaggag gcagagggac 27540
aggcatgagt agaaagacct tcctcaggac ctgaagtcca atgatcctgg tcctgcgtcc 27600
cactagctag gtgatattga acaagtcaca taacctcttt gaacctcaat ttcctcattt 27660
gtaaactttg cacaaatcat ttctttgact gctaaacaag tatgttttga ggaccaacga 27720
catgccaggt acggtgctgg gcactgggaa aacagcagca agcaacacag acatgggctt 27780
gccgtgtaga gcctgcagaa ttagggaaag gataaatgga aacatctcac acatagtaag 27840
tgctcagtta cgttcctcct ggtctctctt ttctaccatt gtaaaggcga tgcaataaca 27900
tagaaagttg ggagaatggg gtggcggttg ctgagggggg aactctgtca tccagaatcc 27960
caccacccca acacaatgac tagcttcatt tttgccaatt tcatcagctc atgcaggggt 28020
tgacctgctg tagggcactc aaaatattca aaccaattaa tgcattgcat ttgtgatcag 28080
aagaaaaaag ctaattacaa tgtaacagat ttacctgatg caaagcaacg caagcatggc 28140
catccctctg catatatgga agcttttcct tttgggggaa acagcaatat ttccatttta 28200
cggaaaaaga aatggaggca cagagaggtc aaggcacttg cccaaggtca cacagacaga 28260
aatgcgaaga gcagctccag aggccagaac tcctgcccat cctgtccagg actgtgggat 28320
gcatccaggg acggacactg ggctgtgggg ctggatgact tggctgcctt tgcattgatt 28380
ggagctgttt agggaaccta ccccagccac tagcatccag tcctagagac acagaaaatt 28440
cactggccag cctcactttt gagcccagaa accccttacc cttcctcctg cctcttgaga 28500
ggccagtgtt aggtgttagc cggggtgcaa agctctggaa ggcaggtttc tgctttctgc 28560
tgccctccag tgggcaaaga aagcaaacct ctggatccat ctggaagcag gtagcaggtg 28620
ttgcccaagt cagctgcggc taatagtaat aataatggct gccgctcaat gagcacttac 28680
cacgtgcaga cgtttttaca cctaatctaa tgtaacctaa ccccttttaag caatttaatt 28740
aacatttaat tcctctctca aggtaggaat cacttcctat atacccattt acatacataa 28800
tctgagactt agaaaaatga cttcccaaag tcacaaagct ggtcagtggc agagccgaga 28860
gtgcaagtcc ttggagatca gaggaggaag agaccatgat cctggaccag gagacagccc 28920
tgcattcttg ggcacagagg tgaatttact gtgaggctgg tgacgcatca gggctcctga 28980
cttgcatgtc ctctcccagg gccatggagg aactttccaa cgcattcgca tgggcatatg 29040
tttcacattt gcaaaactaa cacatttcag ttgcaattgg ctgagaccac tatctctctc 29100
cactgcctag aataatgtct tcacatagta ggtaataaat atgtgctaat aaatccattt 29160
tgtgtttaat aaatcatgtt gaatgaatgg gtagagaaat gaaggaagga aggaagtggc 29220
atttagttca atcttgaagg aagggcagga tttgagagag cgttcctcat gtagcctagt 29280
gggcccctcc acacacagac catccaaggc catgagtggc cttgaatgcc agggtgagga 29340
atctggcctt aggtggtagg cactggggag ccatggaagg ttgcagagca gaggaaggat 29400
atgagtgtaa ttgtcaatta ggcaagagtt gaatgtcaaa taagaggaca gggccctaca 29460
gcggggggcc agagtggctc agataaaact cccctcatcc agcaccacac agagagctgg 29520
tgctcagcca gtgtgatcac agaagcctct gctggggtgt ctataagctc cctggaagaa 29580

-continued gatatccaaa tgctttgcat gtgtggcttt gtgtatgtgt gtgtgtgggg gggggagggg 29640
aggtgctgag tgtggatttg ctcagcactc tagtgtgccc agcccaacgt gggggaaagg 29700
tcaaggccct gtctggctta ggcagggagt tctcagcatt gcagtatgac tgagcctctg 29760
gctggaaagt aagggagcca agagaaaaca ggtttagaag ttggctaggc agaagtggac 29820
ctatgaaatt ccagctgcac cagctgcttc ttttgctaag ctcccgtcat cctttctctc 29880
tctccactgg gtctttctga atgtcaagaa tcccagccac tgtttagtta gcacttgttt 29940
tttgccacac tctgtgaagc accttcaagc ccgatcaccg gattattcct ccaacaacgc 30000
cgagagtgag aagaatggct attatttcga ttttataggt gaggaagtag aaagcccaga 30060
gaggtgaagt tgcttacctg aggtcacata ggagtcaatg gtatacgtga gatcaaaccc 30120
agactccaga ggcagccccc ctcagtcgcc agccgtcctg cctcctctcc tggtctaagc 30180
tggggaggaa aaacccatct tggccagcag gggcggtgt gccctcaagg ataagccctg 30240
cttcccagaa ctcagacaga atttgccagc aagacaacag cacgattctg aaatatctgg 30300
ctttgagccc tcatttagtc ccaactctgg tggggcctgg agaacgggga gaggggtgag 30360
agaagtataa aatagccctc aaattggtga gccaatggtt cacagaaagg aaagcgcagc 30420
ggcattttaa catataaaaa gattctcatt ttcactccta ggaagagaaa cgtgttaaac 30480
ccacaccacc tgagcaggca ctgttttgct atcaaactgg caaacttatg caggtgggga 30540
tatggagaca cactccttct tacattgttg gtgggattaa aacttggttt tggccaggtg 30600
cgatagctca cacctgtaat cccagcactt tgggaggccg aggagggcgg atcacctgag 30660
gtcgggagtt caagaccagc ctggccaata tggcgaaacc ctgtctctac taaaaataca 30720
aacattagct gggtgtggtg gcacacgcca gtagtcccag ctactcggga ggctgaggca 30780
ggagaatcac ttgaacccag gaggcggagc ttgcagtgag ctgagatctc gccattgcac 30840
tccatcctgg gcaacagagt gagactccat ctccaaacaa accaaaaaaa aaaaaaaaaa 30900
aaaaccagaa aagaaaactt ggtttaacac ctatagaagc taatctggta acatctatca 30960
aaattaaaaa tgcacatatc taacaggtat gcatgataca ttcatcaaaa gacttgaact 31020
agacctgcat gatctgatgt ggagccaccc accacatgtg gctgctgagt ccttgaaata 31080
tggctgatcc aagcctggct gacatggcaa aaccctgtct ctactaaaaa tacaaaaatc 31140
agccaggcgt ggtggcacgt acctgtagtt ccagctactt gggaggctga ggcacaacaa 31200
ttgcttgaac ccaggggcgg aggctgcagt gagccaagat cgtgctactg cactccggcc 31260
tgagcagcag agcgagacag tctcagaaaa aagaaagaaa tatggctggt caaattgaga 31320
tgtgctgcaa gtgtgaaata tatatgggat tttgtatact aacaaaaatg caaaatgact 31380
ccttaataac ttgctaatat tgatgatgtg tcgcaataat attttggata gattggatta 31440
agtaattttt atttttgttt tttatttttt tgagacggag tctcactatg tcgcccaggc 31500
tggagtgcag tggcatgatc ttggctcact gcaacctctg cctcccggat tcaagtgact 31560
ctcctgcctc agcctcctga gcagctggga ctacaggcac ctgctaccac ccgtagttaa 31620
ttttgttttg tatgtttagt agagatgggg tttcaccatg ttggccaggc tggtctcaaa 31680
ctcctgacct caagtgatct gcccacctca gcctcccaaa atgctgggat tacaagcatg 31740
agccactgta cctggcctgg gttaagtaat ttttaaaatt acttttacct atttcttttt 31800
cttttttgaa tgtggctgct agaaatatac atggcttgca ttgtggatca tattatatat 31860
ttttaccttt ttattgtggt aagatatgca taacatttac catttggacc atttttaagg 31920
gtccagaagt tcagctgtgt taagtacatt cccattgttg cgcaaccatc accatcatct 31980

```
acccccagag cgttttcatc ttcccaaact gacactctgc ctctataaaa caacaactcc  32040
gcttgctcct ctcctcccag cccctggcag ccactattct actttctgtc tctgtgaact  32100
ggactattct aggttgcctc atacgggaga aatcatatac aatttgtcct tggttgctgg  32160
cttatttcac tcagtatagt gtcttcaagg ttcacgcatg ttgtagcata tgtcagacct  32220
tccttccttt tttaagactg aataatgttc cattgtaagg atataccaca ttttgtttat  32280
ccattcattc actgatgggc atttcggttg tttccacttt tggctatggt gaatagtgct  32340
gctgtgaaca ttttggtaca aatatctgtt tgactcatat tttcagttct tctgtgtcta  32400
tcatatttta ttggacagga ctatgccagt gatctccata gccacataat ttgaaatatc  32460
cctaaaccag gaactaccca aatgctcatc gacagcagaa cggataaatt gtggtatctt  32520
catacaatgc aatactccag tgagaatgaa aatgaatgaa caactacaca cagcagtgta  32580
gatggaactt gcacacatat gtgtcgagca aaagaagcca cacgcaaaat aatacatatt  32640
gtgtgattcc actcacaaaa agttcacaag aggcaaaact aatttatgat gttaaagtca  32700
ggatgatggc tgctctttgg gggccatctg gggGcttctc tggggctgac aatgttctgg  32760
acaccatctt caggagcgtg gtcactccgt gaaaattcat caagctaagc acttgggatt  32820
tgtgtgcaac tttgtgtata agttagactt ccataagaaa ttccaaaaga tgctttgatc  32880
cagcaattcc actcttagga attaaacgac agatatattt tcatatgtgt gaaatgaggt  32940
gtgtacaaga ttatccactg ccgtttttat cagcaaaaga ttggaaacat gccatctcac  33000
acctactagg atgactacta tttttaaaaa atgaaaataa gtgttggtga ggatgtgaag  33060
aaattggaac cattgtgccc tgttggtagg aatgtaaaat ggtataacag ccacggaaaa  33120
ctgtacagca gttcctcgaa aaatgtaaaa taaaattacc ttatgatcca gtcattctgc  33180
ttgtgggtgt gtgcccaaaa taactgaaaa gcagggtctt gaacagatat gtgtacaccc  33240
gtgatcatag cagcactatt cacaatagtc aaaggtggaa gcaatccaag tatccaacaa  33300
tggacgaatg aataaacaaa gtgtggtcta tatgtaaatg gaatattatt cagccttaag  33360
gaggaaggaa attctgatag atgctacagc gtggatgacc cttgaggaca ctatgctaaa  33420
tgagatgagc cagacaagaa ggcacaaata ctgtattatt ccacttagac aaagtatctg  33480
tctaaagtag gctggatgcg gtggcttacg cctataatcc cagcactttg agaggccaag  33540
gtgggcagac cacctgaggt caggagtttg agaccagcct ggccaacatg gtgaaacccc  33600
atcttaacta aaaatacaaa agttagccag gcgtggtggt atgtgcttat aatcccagct  33660
actggggagg ctgaggcagg agaatcgctt gaacccggga ggcggaggtt gcagtgagcc  33720
gagatcgcgc cactgcactc cagcctaggc gacagagtga gatccgtctc aaaaaaaaaa  33780
aaaaaaaaag tagcccaatt catagggaca gaaagtagaa tggcaattcc aggagctggg  33840
aggaggggga ataggatgtt agtgtttaat gggtacagag tttcagtttt gcaaggtaac  33900
attttggaga ggtttggtgg tgatggttgc agaacaatgt gactatattt aatgccacaa  33960
aactgtacac ttcaaatgat taattagcta atttttggtt tttttttttt tgagatgaag  34020
tctcgctgtg tcacccaggc tggagtgtag tgacgtgatc tcgactcact gcaagctcca  34080
cctcctgggt tcatgccatt ctcctgcctc ggcctcccta atacctggga ctacaggcac  34140
ctgccacaac gcccagctaa ttttttgtat ttttagtaga gacggagttt caccgtgtta  34200
gccaggatgg tctcgacctc ctgacctcgt gatccacctg cctcggcctc ccaaagtgct  34260
gggattacag gcgtgagcca ctgtgccctt cctaattagc taaattttat gttatgtata  34320
```

```
ttttgctgca attaaaattt ttcaagtgag gtatctataa ggaaaggtga gaaaatatgt  34380

aagatacaaa gataataaaa tccagagcaa gaacagtata taagtcctg             34429


<210> SEQ ID NO 5
<211> LENGTH: 13567
<212> TYPE: DNA
<213> ORGANISM: Homo sapiens

<400> SEQUENCE: 5

ctgccccacc ccgcgcggcc cgcgccctgc gcggctctcc ggccccggcg cgccccggag     60

gaacccggcc gccgcttccc tggggacggc cgagcctgcc cccgtcggcg cctccccaaa    120

aagaggcccc cccgcagtgg ctcccgaatg tcgggctcgc cagcctcggc ttcctacatg    180

gaaggtccgc gggggcaaaa aacgaaaggc gttcggctgg gctgttggaa gaaggaaaaa    240

gcctctttcc cccttgctaa gcaacttaat ttgggggtgg ggagaagcag gcaattaaaa    300

aaaaaaaagc aagcgattta tttttttcct ctatatcctt agtaaccgga tctcctcgaa    360

ttccgcgcac acgaagactc aggggagggg gccgagtgga cttcaccccg catgagacgt    420

ctggcaaaat aagaaggctc tcgcaaaacc taacaaccaa atatgcaaag ccccaaatga    480

aaaccaccac ctcctcgaac ctcagaggtc tgggggcgtc cggctggaac tggggtttaa    540

aaaaagaaaa tgtttacaaa gtataacaag atgtttgatg ggtggaaaaa tgtatccacg    600

agttacatcc ccccgtttcc ttgcaaagcc ccgctggtct tcctctcctt ttcttctgcc    660

aaaaaaaaaa aaaaaaatcg tgtatttttt taatccacag aaagctttgg ctagaccgct    720

tcaatcctgc gcatctgggt ggtttagggg agtctctggt ctttccccct gcgctcctgg    780

gggcccaggt cctcggcggg gacttcctcg aggctggcgc gggcgcaggg gcagaagatg    840

ctgcggcggc ggctgagccc ggcggggctg acagcgcggg ggagggtggc gcggcggcgg    900

cggagggccc cagacgggtc gcgcgttctc gcccccccccg ggcacaagct gcttgctagt    960

gcaggggccg ccgatgtccc ttcccctggc cgcggctggc cgccgaggct ccccgcatgg   1020

gctgctcgcc tcgacccagc tgcggcggca ggaggccccg gtgtcctctc ggcgcctcct   1080

cctccgagac tctcctcgtc gcgcccggga gcctccttgt ccccggtccg ccctctcctg   1140

gcgctccggt ccttctgccg ccgccagggg ctcgccgcgc cgcactcagg ggctcagggg   1200

ccgggcgctc ggcggctcgg cgccgacgga ctggctctgt ctcgggcagc tctctcccgc   1260

gcggcgagcg gaccgagcac ggcgcccggc tggctcggct ggcgcggctc ggggacagga   1320

tcttccgtgc gccgagcagc aagcgagtgt gcccggggct caccgcctcc cgcaaggcct   1380

cccgcccccg cccccttccc tcccccttcc tcccccttcc ctcccccgcc cccagccgcc   1440

gcagccgcgc cgcctcctcc ccgccccccc gcaccccccc tccggccctc tgctcggctg   1500

gttccactgc gcagtggcgc gcccggctcc ggcctcgtca cgtggccgtc tagacaccct   1560

gtcgctttaa aaaaaaaaaa aaagcgattg tgtttcgcaa acaacagatc gggtttctaa   1620

aagctatttc tccccccaac cccccgccac cgccaccccc tcccgggtct gtagaggggg   1680

taccgatgga ggggagagag ataggtgggg ggcagagaag ctcccagaat ggattgagcc   1740

ccggccggag ccatggagaa attggaaaag cagggagcac cgagcgggct tcgccgcgag   1800

ttttggagct gagcgagcgg gtcggtggcc cgatttcgac ccggctgggt ttcgcggtgg   1860

ccatctcgcg cgcgctcgcc ctagcgcttc attcattggt tttgttttaa aggccctggc   1920

ggtggatccc ttggccgcgc ccgagggcaa ggggaggaga gcgctgtctc ggtttaaaag   1980

acatttatac cggactggac cgaggccctg ggaagtgtgc gctgagggga acagccgccg   2040
```

agggcgggga ggcggcgtga atatgacctc agcggcggcc gcgcgctccc tcccgccctc 2100
tcagctccgg gctccggttt ctaggactgc ctggagaagt gtgtcttgtg cacagctctg 2160
gaatgcattt ggccggctga cgagctgtga ggggcagcat cccggcggga gaaggggagc 2220
gggggtgggg gctcgcctgc gcgccgcggg caggtttcct cccgggcccg gaagacctcc 2280
gccacccgcc accctgcctc ccggcgcggg aaggttaccc agcgagcaga cctgcctagg 2340
gcattcattt gcatgcaggc cctgtttctg ggcctcgtag ctttcaaggt gcttagagtc 2400
agagagttta ttccttgacc ccaggtcccg aagaaacata tacccaagct ggcgggttac 2460
tgcatagaaa cgggcatggc attgctaggg cataaacgca tttacagcgt gaaagctgat 2520
ggctccgaga aacgtaatga tttaaataca cacacatcag tattgatgag gccactagtt 2580
ggcatggtga tctaacctca cttcatattc agtgaaatac gatttttttta aaaagccatt 2640
gagaattgtg agatcaggcc agcagtgaaa ctcgttgggg gctttaaaga atcttttttt 2700
ctttctttct ttcttttttt tttttttttt agagtctcac tcttcacccg ggctagagtc 2760
cagtggctcg atttcggctc actgcagcct ctgcctcccc agatcaaacg attctcccac 2820
ctcagcctcc ggagtagctg ggactacagg cgcgcgccac cacatctggc taatttttgt 2880
attttttggt agtgacgcgg tttaaccatg ttggccaggc tgatgtggaa ctcctgacct 2940
caagtgatct acctgcctca gcctctcaaa gtactgggag tacaggcgtg agccactgca 3000
cctggcctta aaataatctt tagaaaaggt gaaatgtgcc caggtgcgat ggctcacgct 3060
tgtaatccca gcactttggg aggctgaggc aggtggatca cctgaggtca agagtttgag 3120
accagcctgg ccaacatggt gaaacccgtc tctactaaaa atacaaaaat tagccaggcg 3180
ggtggcgcgc gccagtaatc ccagctgaga caggagaatt gcttgaaccc gggagacgga 3240
ggttgcagtg agctgagatc gcgccactgc actccatcct gggcaacaga gtgagactct 3300
gtctcaaaaa aagaaaagaa aaaaagaaaa gtaaagatga aatgtacatc ttgccggcta 3360
aattatatgt tcttaaaagg aaaaggcagg aatgaatctt agccgccttt agagctcaag 3420
tcctctcccc ctctagcaat taaaaagatt tctaacatat tagtacaata gtagatgctt 3480
aataaatatt tagaaatcaa cacttagggc ttaaggggca tttggaccct tcctccaccc 3540
caccaaaagt acctttggta atataaattc aagaggaaat cagcaacatt gcttacatga 3600
tcatttccag gcaaggagat cctaacactt attgacttgg aagatagtag gatgccaagc 3660
agtgcagaac cctactggac ggacagaagc tgccattctg aacatttact gtgtaaggcc 3720
acataagctg cagttgtata acatcataat tttgttgtaa attaaaatat ggcttgtata 3780
aaagggcatt gaaaccttgt gtgtgtatta aaaaaacatt ctaagaagca acctgtgaag 3840
acagcagctg agaaagcaca ggagagaatg gagaaggagt gtaatcccag cactttggga 3900
ggcctatcat gataggcaag ggaagacgaa agagacagaa gtgggatttt tttttttttt 3960
tttttttttg agatggagcc ttgctttgtc acccagccta gagggcagtg gcatgatctc 4020
agctcactgc aacctccgcc tcctgggttc aagcaattct cctgcctcag cctccctagt 4080
agctggaact acacgtgcac tccacacctc gctaattttt ttgtatttta gcagagacaa 4140
ggtttcaccg tgttgcccag gctagtctcg aactcctgag ctcaggcgat ccacccgcct 4200
cagcctccca aagtgtggga taacaggcat gagccacagc gcccggccca gaaatgggat 4260
ttttaaggtg tctgggaaat gtatcatatt ttcaccttag aaaggcttag aaagagtacc 4320
agactagagg tcagaaaacc tgattccagg ctggggcgtt gccgctcact ggttaagcaa 4380
ctagggccaa cagcaatccc cacgttaggc gagcacttgg cagagtttat aagatttttct 4440 gggcaagttt ccgctctcta gggtcccatt ccctctctgt tctggatctc cctaaaagat 4500
cttcacttat tgagagtggt cagaccaggc ttcatagcaa cagaaaggac ttaaataagc 4560
agagaaagta gaggtcataa ttctaattca gtttcttggc taaatggaga atctgaagaa 4620
tcttttggag atctggccag tagtgctaag gctctgtaat gagaggccgg agcacacaca 4680
gggcaggtag gtttcatggg tgtttcaaga gtggagtctg acgtcacggt ttgtctgggt 4740
ggaacatgca tgtacttgca gagatatgtt cccgtatagt gtaattgtag gtgtattaat 4800
tcaggtgtca cccctctcta cacggctttc ctcttccatt ttgctaccct aggtagaagc 4860
tgggtgcggt gctgagcaag tagctacaat gattggtgct gctttatagc tccctggcat 4920
cccctgaatc agttaacatc ccagctttcc tgatagcccc accccatcac attcttatcc 4980
ctctcctctc caagaaagaa gccagaagcc tggcagtaga ggaattccca gcaggctggt 5040
gtgcctagaa aggtagtttc tttctttccc ttccacaggc acaaaggagg ccaacaaaca 5100
cgcagtttca gactattctg acccttaaga aaaaagttta agagttcacc aaactattgt 5160
gaatgagttt gattctaatc atttgctggc agggaatatg gaataaaata gctcatttgc 5220
agttgtttat ttcctgttgt ggcttctatt ttcatctttt agtcgctttg gtgatagtaa 5280
tcaaacccta atcatggtgc cgccacaagt cacagagacc aaaataactt gcagcagagt 5340
tatgacaaac aaggatggaa tcagctaaag acctggctac ttaatcaccg gccactgccg 5400
cccagaggac tgtggggctg cctcttgacc ggctgctggc taggaatcta gaggagagag 5460
gaagtcgagg gaagttgctc caaggcccat gttttctgag cagccaggga aggcagtaga 5520
gtgcacagga agtgaccgaa aaagcaggtg aattctccac acctgccaag gggagaggca 5580
ggcttctgga ggggcctgac ttgagagaga aagaggaggg gaaaaaaatc tccaaaactc 5640
ttgacacctc aaaacaatga taagtaaaag ctgaaaagtg cctgtctaga gaagacagga 5700
ttctgccttt cagttctttg ctcattgtca gtggattcca gaagagaagg gcagagagag 5760
gccccaaagc atgtatggat gtgtgttgat gggagtgagg acaggggtaa agattttttt 5820
cttgcacaag ccaaaagaag aaaccattga ggagaccaaa aaagtactgg aaaacatcaa 5880
catttcttgc acaatcatcc cctgaaaaat gtgtgagtga gccctaaacc atgcacaact 5940
ggcaacaata caaatggaag tgatggctta tgaaaagaag acagtacaag gaaggctgat 6000
gggacaatca acgcttcttg gcttctcttg gaagaacagg aacataagtg aatgaaaatg 6060
catctaattc actatcaaac aaaaatacta taagcccgga ctccacaaat attcttggat 6120
tacagacaag ctgtcagctg atccccaaca tttgccaggt gcctatccag agcatgcaac 6180
taggtatcag ggattggaat gggggcagga tgaaatgaat gttgctatgg aggagatgag 6240
aaacatccag aaaaggtaaa gagtgaggac aatagagaca ttcaaatcta cagtcacatt 6300
tagatgccgt ttcctccaag gagggcccct ggacagctga agaacagaac tgggagggga 6360
attttactct gtataatttt gtaccttttg aattgtgaac cgtgtgaatg tgttacttat 6420
tcaaaaataa acagatttaa attgttttca aatctctgct tgcttttctc atttcctgaa 6480
attcgttgtt ctgatgtcct tgtagaaaag gacaagttgg caaggtccca cgtggaaatg 6540
atgctataga cagcttctct ctctgtgagg cagttgctac aggaagaggc tggtaacaac 6600
agaggccaat gtctcatccc agacagcaag ggtggaggct gcttcgtcat gagcctggcc 6660
agagtcagcg aggaaacatg cccatcctaa tcaaaagtca ttccagatat cagtcaggtg 6720
caagtcctaa cctgggatgg acagcctaat aaatactgct gtcagggccg ggcgcagtgg 6780

```
ctcacgcctg taatcccagg actttgggag gccaaggcgg gcagatcact tgaggtcagg   6840
agtttgagac cagcctggcc aacatggtga aactccattt ctactaaaaa tacaaaaaaa   6900
ttagccaggc gtggtggcat gctcctgtaa tcccagctac ttgggaggct gaggcaggag   6960
aatcacttga acccaggagg ccgagggtgc agtgagctga gatcaccaca ctgcactcta   7020
gcctgggcga cagagtgaga ctccatctca aaaaaaaaaa gataaatacg gctgtcagga   7080
tgacacaggc acaggaagga gcctgcccaa tctgagaaaa tgagagcttt gctttttgga   7140
acagaaacgt gttcacatga ttttcaattc atttagccag cactgattca gagctgattg   7200
gagtcaggat ccaggagaga cctctgaggg ttataaatgt gaggattaat cagcctttgc   7260
cctcaagaag tccacagtct aggagagcca caaactctca tgaaatggga tcagtgttac   7320
cccagcagca agaatggagg cactggctct aagaacagaa agtcaaggga ctcattctgt   7380
ctgggagagg cctcaaaagg tttcccaaag gaagaaatat tttagactag attagctgag   7440
ttgactagcc aggcaaaggt gatcagagtc ctaattgtcc tatcaaaaag aaaaaaaaaa   7500
aagaaaggat tacaaatatg agccaccaca cctggaacaa tgcctggtgt gatggctcac   7560
gcctgtaatc ccagcacttt ggacagctga ggtgggagga ctgcctgagc ccaggagttg   7620
gagaccagcc tgggcaacat agtgggaact cgtccctaca aaaaatacaa aaattatggc   7680
caagcgtggt ggctcacgcc tgtaatccca gcactttggg aggctgaggc aggtggatca   7740
cctgaggtca agagttcgag accagcctga ccaacatggt gaaaccctgt ctctactaaa   7800
tatacaaaaa ttagctgggc gtggtggctg gcacctgtaa ttccagctac tcaggaggct   7860
gaggcaggag aatcgcttga acccgggagg cagaggttgc agtgagccca gactgcgcca   7920
ctgcactcca gcctgggtga cagagagaga ttctatctca ataataataa taataataat   7980
aataataata atacaaaaat tagctggggg tggtggtgcg tgcctgtagt cccagctact   8040
ctggaggctg aggtgggagg atcacttgag accctgaggt agaggctgca gtgagctaag   8100
actgcaccac tgctctccag cctaagtgac agaaaaaaaa ggaacgaaat tttgttttct   8160
ttgagctaac ttttcaatac ccaagccaca cttatcactt aagtgtataa ctttataaac   8220
actcccaagc cataggaagt cagtgatgaa agtgaggtcc ctgcagtggg tggtctggga   8280
gggcatctcc ctcagaaggc agttttctct gtagaaaaca ttggaggaaa aacactagat   8340
cgtctacggt tacagagaag tttctcctca aataactata gagatcgcca cgatctccac   8400
ccctcagatc aagagcaggc cttacttgag tcaaactggt tcatgttagg aagttgtgcc   8460
agttttaaga caagtggaag ggaagtaccc tcagcaggga agttggctga gatgcctcag   8520
taatgggggt acttaaataa tgctctcaaa tgccaacaac aaaaaattat tatttgccat   8580
tatcgtatag acggtgagac atacagttgg ctgatcccta caggtactaa aaaattgatt   8640
ttaaagacag caaagcaagg aaatcagtgt tgagcctaac ccagatggac cctgatgggt   8700
cctggtgtta tttctcactg gccatgttgc agacaagttc ttcattccag cttccagcca   8760
ctcaactggg cagctccaag ttcctggtca cattgggcta ccaaattatc cttttctgtt   8820
ttctgatttt tttcctattt ttatctttcc cattcctctg ccaaaagtcc ttaatgggtc   8880
acttaagtgc tgaattctgc ctagtaagtg ctggttagga tctgagctat gagacatgct   8940
ggtaatcgtg attcagaaca gaaagcctgc ggaggggtga atgatgtttt atctgtagta   9000
gggaattggg actagagcaa aggggtcata caggtgaccg cacatgctgc ccctggcacg   9060
tgctgggacc caccgaagga gtgagggcca aggcatcttg ctcattctcc caacgcagac   9120
```

ctaggagaat agaaaggccc tcagctcggc tttaggattc aatagacttt tctgccattg 9180
ctagctataa gaccttaggg aagtctgttt ccagtctgtc taccttcctc atacaacaaa 9240
cactgaatta acaatgtctt gtgtcttctg tgtgccagac tcagcgtgag gctccaagaa 9300
caaagtcctc acggtggggt tgctgggagg agacgttcac accacaagag ccccagtgct 9360
atgtaaacca agtggtatac agatgctaat tatcatatta tcatggattc tgaggtccta 9420
gctgcccaat aagcacattt tgcctaatct tccgtgccta ggaaatgaat ttttagagga 9480
gataattgtc caagtgatag ggtaatgaag aaggaagcta ctttttctag tggctgggat 9540
tttgtttgtg tgggggtttt ttgttttcag ttttttgaga cagagtctcg ctctgtcacg 9600
caggctggag tgctgtggca ggatcgtgac tcaccgcaac ctccgcctcc cagattcaag 9660
cgattctcct gcctcagcct cctgagtggc tgggattaca gtgtgcacca ccacacttgg 9720
ctaatttttg tatttttagt agaaacgggg tttcaccatg ctggtcaagt tggtctcgaa 9780
cctcaagtga cctcaagtga tccgcccgcc tcggtctccc aaagtgatgg gattacagcc 9840
atgagccacc atgcccggcc ccttgtgtgg gttttataag gaccagttag aactctgtca 9900
aagaggtaag gctagcgtct gagtttaaaa acaaacaaat aaacctaggg aaatcttttc 9960
cctgttggaa taagagaggg ataagtgagg aaacaatgta agtgttttta gttcttttct 10020
agtactacta tgagtcatac atattttcct gtgtcctgga gatatctccc ctggtaatta 10080
tgagatacaa ggaggaagtg aagagggatt cattttcatg gagaggagtt acccagtggg 10140
caggattctg ctgtgcccaa tttagttttg atccccctct atcccataaa catttctttt 10200
gaaggctttc aaagttgggg gaagatgatg ttatttagca ttgttagagt ctggtagacc 10260
ataaaggaaa aatctggaga aatgcagtaa aatgaggttc aagccagaag ggattataaa 10320
cgttacatag cccagagagt ctccatcttc agtccatctt atttggtact ttttctttgc 10380
tttttctatt ttattgattt ttgaataggc aatgcatgca caatggtaca caattccaag 10440
aatacaaaag gggaggaaga aaaagataag gcttccttct acctgggctg ccagccaccc 10500
atgcctctca taggcagcca ccattacagc caaagaggca gaacatgaac aggcctcggc 10560
tcggcgcgat ggctcacgcc tgtaatccca gcactttggg aggccgaggc aggagcatca 10620
cagggtcagg agatcgagac catcctggcc aacatggtga aacgccatct ctactaaaaa 10680
tacaacaaat tagctgggtg tggtagcacg tgcctgtagt cccagctact tgggaggctg 10740
aggcaggaga atcgcttgaa cctgggaggc ggaggttgca gtgagccgag atcgcgccac 10800
tgcactccag cctgggtgac agagtgagac tccatctcaa aaaaaaaaaa aaaaaattag 10860
gtctctgctt tgctctccag tcccacttgc ctggtcaata tctcaaaggc accctgagct 10920
cattaggtcc cagataggcc atcttcctcc tgttacaaga aagtggtccc gagccagacc 10980
acaagagaga gttctttgga tctcgcataa gaaagaattc agggcaagtc cacagtgcaa 11040
agtgaaagca agtttattaa gaaagtaaag aaatggcagg gcacgatgac tcacgtctgt 11100
tatcccagca ctttgggagg cggaggcggg cggatcacca ggtcaggaga tggagaccat 11160
cctagctaac acggtgacac cctgtctcta ctaaaaagaa aatgaaaaac taggcgggca 11220
tggtggcaca cgcctgcagt cccagctact cgggaggctg aggcaggaga atcgcttgaa 11280
cctgggtggc agaggttgca gtgagctgag atcgcgccac tgcactccag cctgggtgac 11340
agagcaagac tccatctcaa aaaaaaaaaa aaaaaaaagt aagtaaagga ataaaagaac 11400
agctactcca tagacagagc agccccaagg gctgctggtt gcccattttt atggttattt 11460
cttaatgaca tgctaaacaa ggcgtggatt attcatgtgt ccccttttt tagaccatat 11520 agggtaattt cctgacatta cctggaatct gcaaactgtc atggcgctgg tgggagtgta 11580
acagtgagga tgaccagagg tcactcttgt cgccatcttg gtggattttg gccagcttct 11640
ctactgcaac ctgttttatc agcaaggtat ttttgacctg tatcttgtgc cgacctccta 11700
tctcatcctg tgacttagaa tgccttaacc ctctgggaat gcagccagta ggtctcagcc 11760
tcattttacc cagcccctat tcaagatgga gttgctctgg ttcaaactcc tctaacactc 11820
ccaaacaggc ttttcctcca gagctccacg ctcagaaagc tcactcctca ccatccagtg 11880
atcacaacca gaaaccaagg acaacaaacc tctcccttac cccttatcct accagcccca 11940
aagcctatcc attttatctc caaaatgcct ctccacttat ctgcttttct ccagtctcac 12000
ccaccacaac cacccagcat ctgtccggga ctggtccaca ccttagcctc tgctgtcttc 12060
ctcagaccca cccagtccct ctcccctgcc aggtggtcgg gctcagtgct gatttgagtc 12120
ctcagaccca cccagtccct ctcccctgcc aggcggtcgg gctcagtgct gatttgagtg 12180
cacaaccacc cagcggggct tctgcacgcc cttggatcaa agacaaattc ccttcctggc 12240
catacaaaac cctgagtgac ctggagccct ctccctccct cccgcgtccc ctcagtactc 12300
ttccttccat cccactgagc gcgttcactt acacagggtg cttaccagtc agcttcccag 12360
ctgtggaatc tctgccggct gcatttttttg agtaaatggc tgtatgtaca aaaagagttc 12420
acattcattc ctcttttttt cttggaatgg gcagagcatg ttaagtagaa tttgatgatg 12480
gagacgatga agaaattcct tgacgttaat ctgaaattga tcacttgttt aaaattacac 12540
aaacacatct tgcttttgaa agaaccaaag ggaaatacca ttcaatgcca aaagaggcct 12600
aggaaagcag ggatgagctc atttgaaaaa gccccaggag cctgatcaat gtctaggttc 12660
tggctttccc agaggagcct cacttgcctt gcttatgctt tctgcatgca atacctccca 12720
gtgcaaagag agggtagtca caggctctgg gtggaatggg agatccccat ttgcccccac 12780
atccttcctc ctcctggcac attggtctac tgggtagcag ccctcaggct ggggggagct 12840
ccccaagggt tccctaccca ggcctctgcc tcactctcca cttccagctt agttttcccc 12900
tcttccgagt ccctggattc caggggacac cagctctgtg agcatgaaca ctcagactag 12960
gggagaggcc ccgacagttg gctgtgcgtg cccagaactg cctatccaag tagacttctg 13020
ctgtcaagcc agagacacta aggaacacct actcaatgag cagtaaatcc ctcatgacgc 13080
taggagaggg tgggcacacc cattccatct cccgcccacc ccactccaca ccccaccaat 13140
cgcactcacc cttgatctca gccagctgtc ccctggtgtc ctccactggc cttggagatg 13200
caggagtacg ggagaagcgg aataaatccc accccagcaa gaaaaataca ggtcccagag 13260
gcactcaaca gacatatgtt cccttcctcc ttctctcctg gtgacagtga cagatagggg 13320
cccccctgggg cgggtggata ttttcatctt ccaagagaat gcactccatt actccaggac 13380
ttttctgtcc tctccgcctc cacacagcct tccagcctaa cactcagtct ctcaaggaat 13440
attcttgaca ctttaaagga tctggccagc acataagcca atgtggctgc attctttaat 13500
taatatttat tgagtgtccc tattaggtgc ctggcaagct cagagtgttg tatgtggcta 13560
aaatatc 13567

<210> SEQ ID NO 6
<211> LENGTH: 13151
<212> TYPE: DNA
<213> ORGANISM: Homo sapiens

<400> SEQUENCE: 6

```
ggcactagat ggcactagaa cccacacctg ccacccccag gcagggcttt ttccttggca     60
ctggtgcagt caccaatctc agtagctttc acgagcctac aattgaaagc acttttctct    120
atggctttac atcttggcct ttagggcagt aacccacagc ctagttagtt ctacttcttc    180
tgccaccctt cccttgtttc tgttggaaag tggtgcagct attggaggat gtgcttgact    240
gaatgtgctc cctcagcttt tcagtccata ggatgggccc cagctatacc ctttcactcc    300
ttccctgctc aaagatcatg gaagaattcc tgaggtaaca ttttcatctt gggtgagact    360
cattctttac aattcacccc tgtggtgagc tcagcctagt gcagcctctc gtttgctctg    420
ttcacacaca cacacacaca cacacacagt catgcatgta tgcacatacg cacgcacaca    480
tgagaaacac aagaaagcac ctttaaaaaa aattagcgga tgatactttc cctttgtgga    540
tggttgcacc tcataccaat catgggttta agcttggtga ggaaagagat ggacggagat    600
agaagctggg gagaaagatt tgtaattatt taaacttatt gaatagctat gtgcctgctc    660
cgctctgaaa atagcgcctg ggttaaaagt ctctgtacct cagaaggtca ccatctgtag    720
gagaggtaga tcaaaacata tcattttaat caggaagagt ttgaggtgtg ggaggttaca    780
aggcccaggc ctgagatgga actagcaccc acatctgaca cccccggcac agggctcact    840
cctcaacctt ggagctgttg ccaacctcag taggtatgaa gaatgtattg ggcacacatg    900
ttgaaagcaa tgtttttcta gggcgtttag gagtgagaga agcaagcgca attccctgtg    960
gtgtcccaac cacaaagcct cttctacctg tagcagacag aggaggtgac acatgagctg   1020
agtctgggat gacaagctca caagcatttg ggtcaagca ttccagggag aggagtcagc   1080
ctgggcaaaa ccaaggcagc gctctcggta ggcctgggcc tctggctagt ggtttccttc   1140
aacccacaca ctgcgcatgg aaccacagaa ggcagcacag cagagcatct gccctcacgt   1200
tcttcctggt ggggggcctc ccaaggacat tctgcctcag gttcttattg tctgaggtca   1260
ctgagcctcc tgaaagtatt tcaggaatgt ggaggcctga ctcactctct tccttgagtt   1320
cacagtctga agttcataaa acctcttccc cctttagtca ttcttattca aataccggcc   1380
cacaagtttc acagatggag ctggcaggag gaatcttggg aagcattttt ttgctcagga   1440
tgtgaaagta tatgaagagt ttgggagatc caggagcaat cattcactaa gagccagacc   1500
cctgtggcag gcgctggcta aacgcagaga ctggctggct cgctcacaga gtggagatca   1560
ctggcagaag agaaatgcca tgaaagcatc cactctgtgc ctcagtttcc tcaactgtaa   1620
acagagacaa taaccacacc ttcttcagag aactggatgg ggagtgagtt aatccacata   1680
aagtagttag aatacagcct gacacataat aagtgctcaa taaatactag tttattgttc   1740
atactattgc ttattgttgg cagagtgagt tgtctacaca ctaagtggtg tggggaagag   1800
gaggcattcc tggaatagga ctgcgtggga taaacctgaa aggaaaatgt ccaatgccgt   1860
gggtgagtgt ccagatgggg aggcctttag acatcacaca cacacagcag gaggggcagc   1920
ttgggagaga agaaacccga gtggcacatc tagcctgatg ccaaagtatc aattcatgca   1980
cttcttccgg ttggaaacag ttataaaaat gtccagggaa ttaacaaagg ggatgcagga   2040
gagatatttg gagtacggga tgggcataca catagccaag catggggttt caaattggtg   2100
ttattcacct tatttctcct gctgccgtgc aggcaatgaa attctcagtg aggcaggcca   2160
cagacagatc agatgctctg ttttcctcct ttctgactgt agctcagttt agaggattga   2220
aaatgctagg agacatctag cctaccctct ccctgctcac accgcacctt gcctcagagc   2280
tggttttgac atctgtccta gaagacatca tccattgcct tgattcatgg gtatgagtct   2340
aagcaatctt aaccactgct gggattccat ttggacaagg aaaagctttc tctgcttttc   2400
```

```
agaacactct acagagaaac cctaacttta gtaaggctct ggggacccca ggggagatcc   2460
agagaagtaa agcacccagc ccaatggagc ttccagaatg cattttgagg gacagtgctt   2520
tagttcttcc tttgacctca gtctcttttg gtcattcctt gtccccattc tactccaact   2580
ggaaaggctg agtagctgct cctgcatatg tctgttattg cagtgaccca aagtaagaat   2640
cttaaatgaa tttgaaatcc cttaaaaaaa gagtaaaaat agtcctagtg gaaaagatgg   2700
ttcaggagtt tcacagaagg gaattagaag aagccattac tgactcaaag aaaaagatta   2760
ctgaatagat agcagaaggt aacctctgcc ctactttcag accaatgagt agatataaat   2820
gacattacac tctcgcttca tgaaaagtaa ctggagagtt gagatgaggt gattcttgaa   2880
agaaggaaag gctattagat ttcttactat taatgattaa ggttcctcaa tttttatta    2940
accagccttt ttttctaatg acaaaataca tccttatggt acataattca aactgtagag   3000
aagggaataa agtaagaagt aaaattcctt ttctccactc cacaccctcc ttcccacacc   3060
tccctgaata cttccctgcg gaaaccacta ttaacagttt cttctccatc tttctagaat   3120
tgcctatgta tattccaacc tcctctgaca atcctctttt ttactcaccc acaagaggcc   3180
ttccaacttg gcatctcaca tcatgatacc gcctttgtct gggaagctct tctcctcttt   3240
gcatggctcc ctcatggctg ctacaacctt ctcggaattg tcaactactc agagaggtct   3300
cctgtgactt ctctatttaa acaaccccac caccatcacc attctccacc ctgacaccac   3360
cagtgtctgc ccaaccctta gcacaatgtc cagcacacag tatttgatca atacatgacg   3420
gatgcgtgag tacattaggt acgtgcgcat gcacacatat gcatgtattc tccccacaaa   3480
gtataaaggg gatggtatta cagagataat tctgtaattt gctttcctac ttcacaacat   3540
ataataaaaa acaataatga taatatttct taagcactta tgttccaagg actattctaa   3600
gcattttaca tgtattcttt catttaattc ttacaacagc cccttaaggt ggtactaata   3660
ctacccgact tgccagataa ggaaacaaag aaatggagac atggggaggt taaaacacag   3720
cttgcaagtg gtagagccaa tacataaatt tacactaatc gtaaaatggc tgtttagcct   3780
taattcacat attaaaatat tttgtggcaa aatatactca acataaaatt tatcttttta   3840
ataattttta agtgtacagc ttagtggcat caagtatatt cacattgttg tgcaaccatc   3900
accaccatcc atctccagaa ctttctcatc atcccaaact gaaactcagt acccattaaa   3960
cattaactct ccatgctccc cttcctccag cccctggcaa tcactatgtt atttcctgtc   4020
tctataaatt tgagcactgt aggtccctca tagaagtaga ataatatagt atttgtgctt   4080
ttgggattgg tgatgggttt gttgcactta gcaagtcttc cttattaatt aattaatatc   4140
taatgaataa ttttattgag taaaatattt gagtgcatga tacaaaattc aaaaggcata   4200
gaataaaaga gcaagttctc cttctacctc tgtctctagg taccccaggg gcaaccactc   4260
ttcctagtgt ccttccaaag atgttctatg catgtacaat tacattattt gtatgagtca   4320
tatatgtata atatatgtat agcatactat acatactgtt ttgtttcttg catttcccat   4380
ttaactctat accttggaga tagttacatg tcaatgtaca tggaactgcc cctcagtaaa   4440
cataatttac ataatgtatc cagctgtaca cttatagtat attcactttg tatgtatgtt   4500
tcaacagaaa cataatttac agttcaaaac ataaattatg tttttcttga aatatacata   4560
cagaaagtga acagctggat acattttcac aaactgaaca tacccctata aacagtaccc   4620
tgaagaagaa acattaccag cattactagt ttcccaagtc tctcattttt tattccagac   4680
gttactcact gtcaccaatg gtaactactc tcctgactta acagaataga ttagttttgc   4740
```

gtattcctgt agttttgttg ttgtggtggt ttgtttgtct gtttgtttgt tttttagaga 4800
caggatcttg ctctgttgcc caggctgtag tggcacaatc atatctcact ataacctcca 4860
actcctggga ctcctgggct taagtgatcc ttctgcctcg gcctcccaaa ctgctggcat 4920
taaaggtgtg agacactgca ccaagccctg ttcatgtagt ttttatgaaa ataatcctgc 4980
tgtatacact cttatgtttg gcacatttca ctcatcctta cacctatgag attcacccac 5040
gtcgctgacc ttcagttgat ccttaacaac atctttggat aggtgaaggc ccttgcagct 5100
gtggatgagc ccagctggca tgaggtctta catgtcatac ccaccttctc tcagtcttgc 5160
cctcacaacc tttgaatttc tataaagtgc tttgtaaatg ccttaaagag tccacatgta 5220
tccaaaattc atctccagat gtatctaatg atgaaaacca gcagcccgga gctgaggttt 5280
gtgtaaagtt acatcagagt gaggaggggg gaaggagcac agccttccca ttctgatcag 5340
tgtctctgtg gccacagctc aataagactt gctttttgag gcctcatcca ctcagcccag 5400
aactcaaatc tcaaattccc caaacatgag gaatcatgac aaagcactgg tttgcattct 5460
cttggcaaat gttactttaa aagtagagtc aaaactactt ccaagtaaag agcaaagcag 5520
ctttaaccaa tatcagcaaa gggtctaaga aaaaagatgt ggctaatgta ttccgtctgt 5580
ttgtttgctt tcttgtgccc taagactcag gagaaaatat cagtttggga aagaagtcat 5640
aacacatggg gcaggaacaa aataccaaca gagcgaagtt gcacacgctg tccaacctgg 5700
tggcctgctt atgaatttga aatcccagac cttcacatga gtccccagcc tcaccccatc 5760
cctagcctgg cacagacagg aatatctatt tccagatatg agctgttaca tagcagaacc 5820
aatctgtaca tccgtgtggg gccaatcgtc agtgctctga ttggctcatc agccaacatg 5880
cagggctgca ttcctgtggt tcacccttcc agaagggcct ttcccaacac cacatgctgc 5940
ctgtgctgtg tccagcagga gagggggagg caaatgatgt gtctcatggc accacaggct 6000
ctgttttacc agaataatac tgttctttgg cccactgcat ccgttctccc cacatgggcc 6060
ttttcctcac gtggacccta aaagaccact tctctattta cctgccaacc tgtaacagat 6120
aattatagtg gctgccagat atcccttcaa attggtcatg atctcattcg gttattctag 6180
cagcaaaaaa gttacagaaa acccaagata atattaaaaa aagaaaatca tcccctggct 6240
ttcacctttc ttgtggcagg caagaaaagg taggaagaat aagcatagga aaagaaaagt 6300
aagagcttgt ggggcaagtt gaaaacaaac cttaccaagt ccagaaagaa ttttccattt 6360
aaatgcttta taacaatttt ctctgatgag tagtagaatg ctgaataaga catgttactt 6420
tttagtgact tttcaatctg gcatctattg aaaggtgttt tatacccact gcagccaaga 6480
ggagagggtg caggggagat cacatactct cccagcaagg cagggataga aagcccctgt 6540
caccaggggc tgccgtttct ctggcccagg aacctgtgga ggctactcct ggataactac 6600
acactgttca gctgtattgc atgcaattat atcacattcc ttcctggaaa cttctccaaa 6660
aagagagcag agatgagaaa cactcataga gaaagctttc actggggcac acaagctgaa 6720
ctggcaggaa tctgaagaag gcaaagcaat ggaatgttaa cctcgaatga gtgaacagga 6780
gataagaaaa catcagctga cagagcaaac accccggaaa tgtgacctgc ctaccctggg 6840
aatggctaga gctcttgaac tagcctttaa atggaaagtt cttcctgact cgggttttga 6900
aaccaagact gagcaaaagc ctcagtcttc attcctgaga tgaagtttag agtgcaaaag 6960
atttcgaatg caaaagattt tgagagttgg ttagagcccg aggacaagcc tcttgtgaac 7020
agaagttcca agagtcaaca gtagctggca gcagacaacc tcttcaggct gaagggtggc 7080
agaacccaag atggctagtg cagaagacat ctgagagatg gcccaaggct gtcctttgct 7140

```
tttcaaatga ggaaaaggtc cagaaagggc tgtctaaggt cacatagctg gttaatgaca   7200
gagctgggag tagagccaca ttgagctaag ttgtattcct acatctctac caatgtgtaa   7260
cccaaatcaa aataattggg gggcagaaga aaggggaaaa gttatggtct ttgaaagtca   7320
ttagtaatcc tatcattaga cacataatta atatcatttg ccaagatact aatgtcttaa   7380
atgtgagagg caatgtctat tgcactaatg aggtgactgg taccatggcc atttatggca   7440
gatatatttt ttcaaattta agactttagc atacacatat acatatggag agagaaagag   7500
agagttgatt tacatatata tttcccatct aaacacacac cttgaccatt ttgccaggaa   7560
aataaccaaa caacttccat tgaggtatac aaagaatgat gacaaagtta cgtggcttat   7620
agtttaaaaa gaaagtttag gctgtgtgcg gtggctcagg cctgtaatcc cagcactttg   7680
ggaagccaag gtgggtggat cacctgaggt tgggagtgtg agaccagcct gaccaacatg   7740
gagaaaccct gtctctacta aaaatacaaa attagctggg cgtggtggca catgcctgta   7800
atcccagctg ctcgggagac tgaggcagga gaatcacttg aacccagaag gcagaggttg   7860
cagtgagctg agatcgcacc actgcactcc agcttgggca acaagagcaa aacacagtct   7920
caaaaaaaaa aaaaaaaaaa aaaaagaaag acagtttaaa aacaaaattg cttgggtccc   7980
tccaccttgc cttttcactc tctattagtt tttaaagagt ggcttgagtc acagtgaagg   8040
tggagaaaaa gcagaagcaa agacagaagc ccattcaatc aggactacat atgccctcgc   8100
aggtgaggaa cagttggccc aattgtgaag tctccaggct ggggcaagga gggaaggcat   8160
gcccaggaaa agcatgggtg agctgggata gtttctatgc ttatttctga aggcccatca   8220
aggaaccaag agaaactaga atgtcctgtt gagggaggat gcagactttt tccctcattg   8280
tttcctaatg taggttagaa cactgatggt ctagaacact gaaaaagatc ttttgtattc   8340
tattcaagat agatgaatga cagtacagtc acagccagtt agagctagaa ggacctcata   8400
agtcacctag tctgacatct tcattttcca gatcaaaaaa tggggtgcag atagatctag   8460
caacttgatt aaggtggcca caagctctca gagtgtgttt tgccaacctc tagtgggtat   8520
attggggctg gggggtgggg tgcacagaca gcaagcactc caacaggtct gtagatcttt   8580
caaaatgcaa gccaaaatgc acaaaggtgt gtgcagagta cctccctggt tggtttcata   8640
aattaacttg aaaattaaat tgttacaatt ataataatta tccagtcttc caaaagtatt   8700
catctggagt gtaagcactt taaacatgat cttctgttct cctaaaggtg ctggagcatg   8760
ggaaggctag cccgctgcca gccacatgga gtgggaggat cacggagcct gaagctgaga   8820
ggccacagca ctgcacctga catatattac caacttgcca tgcaacttca tctcattgac   8880
tccgcattcc catttttgg agtggatcac ctgcagttcc cttgacaact gagtgtctgt   8940
atttttctgt atcgtccagt gtgatgacaa ctgtctacac aaccaagtct ggccagcact   9000
gaacacactc agcttcccca cagtgctcca agtctcaaag cccaaactgc agccaaatct   9060
tggcagtgtt gtcctctggt caggccagag cacctttctg aaggaccttt ctgaacattt   9120
ttagaccatt cgatgaatga ccctaaattc ttggcgcata attgggactg ctgccatcac   9180
gccagaaaca tttattaagc acttactgtg tacagtgctc aagacctgcc atcttgtttc   9240
catcttgaca acaatgatgc acagtagggg ttgtcattcc ccgtttcaga gaagagtaaa   9300
gctcagcagt ggcccagtaa cttgcccaag gccacacagc tactgggtgg cagaactgaa   9360
ttaaaccctc cactttttga ctctaacacc tttgcctccc tccttagggc gcaggcacac   9420
ccagccaggc tgagaggcac tcaggcactc tcgaacttca tgtttgtcat gcatacatat   9480
```

gacttccttc gacttctctg caaatttcca ccatatgcat ttccatagca acattgcaac 9540
acaaacacgg tgtaatcttt gtccactgca gtacatagct tgaaaggttt ttttgttttg 9600
ttttgttgtt ttgttttaaa taaaaaggag ctgcatatgt ttacagctga cctagatccc 9660
atggcaacaa ataacagata taaacttggg ttcttttcct ttcctttcct ttctctaaat 9720
ctttttattc ttttctcttg tatggtaata gtttagaaca tcaaaaactg ggttgcacca 9780
tttgcgatta agcagggccc ctattcggtg accgctgcgc cgccagcctg gcgcgggcct 9840
cctgcaagac aatggccacg acctgacgcg cgagcgccag ccccagcccg ggagtcacgc 9900
cgctggcgct tgacgcacgc ggagacccgg gggccgtgcc ccagctttgt ggaacctgag 9960
ggcggctcgg gtcaggtcgg tccccgcggg aggacaggcg cgacccgtcc ctcaggaccg 10020
acggcgtgtg gctgcggggg catggggtgc ccctctcggc ccggtcgctc cagcgagggg 10080
acgctggtaa gtcccacccc tgccatcgcc gcgggcctcc tgggcacgcc cggccgcggg 10140
ccccagatta ccctcccggc gaccctccag gcggtattgc tgtcagacac attttacaaa 10200
tgcaaccctc cagcctaacg aaggccagca cctggcccac gcccacaggc tgggaaggga 10260
gagtgcaggg attagaatcc agcacttttt aaagattttg tttcactcta cttcccgtgg 10320
ctcctcgccc caagggcact gtggaactat ctctgcccag gatcacttat ctgaagccgg 10380
tgttatgctt ccttcccggg cagtccctgg gtgcagcttc cggacgggct agcttgggag 10440
gcattccttt ccctggctga tgcaggaagg tgggtttgtc tgtctgtggt ccctggttct 10500
cccctctgat tctccctctt cccagagccc cagcttttaa aggcttcata ttcctgacaa 10560
atggagatcc actgacatga agaaattctc aagcaactag gcaactggga ttgtgcaggg 10620
gcttgcccct gatcctatag taaaaggtcc agccctcact agctgaaggt gaggaggaat 10680
ttcattgggg aaatgtcatt ctttgtttca ctgtcatgaa tccagtgaaa cttattatca 10740
ccagaaatgc cccttggctg cttcctcgct gaaattgtgc tgaggtatct gatggcccac 10800
tgaggtagtg gataggaggt tggacagcca agtggtgata agaaaaccta ccatttcggt 10860
agtactcact cggtgccagg tgctctgagc agctctctat aacactgcct cctcacaaac 10920
cccaaaggca ggattattat actattatat agtcataata ttaatatgaa tatgatacta 10980
ttaataataa atttattctt gcttaccacg tgagggatcc aaagcttgaa gaggtcacct 11040
atcctgtcta gatcccactt ccgactctag agcctgtcca ggagtgattt ccccatagaa 11100
gggaaagggg gctgctcagc agagaaacag aaataagatt gtgccaggag agatcgcatt 11160
attcctcaga ctcaaaggcc gatttgcaca cctttacgat aggtagaggg agaagagtgg 11220
aaacacccct atctctttgt ccaaacccac agcgagatcc aaggctcagt caggaaggct 11280
cttcatttag tcaattgttt tctgttttca gaactaaagt ggaaatgacc cagtgaggaa 11340
ggaaaataag cacagaataa gcatgatctg ccttggtcac acaattaaaa tacataacgc 11400
tgctaaaggt acaccactct tccacccacc ccttcagagt gagaaaggcc ctttttgccc 11460
tggaagccta ctgaagcatt ctactgggga agtattctac tgaaatattc tagtggggaa 11520
gtccctgccg cttctgaagg aacactgaaa gaaaccttat tccttagagt acagtcaccc 11580
agagggttta ttctagaaat gcagagaggc attagagatg gtatgtgaac aaaagcaggg 11640
cagaggatgc acgcccagat gctgtcttgg ccaggttgca attcgaatga tctaatgttt 11700
tctggcttct tattgctttg cttttccaat ttggtttgga tatttgcatt actgtattat 11760
tttccctgta caattgctgt tgtctgtaca caattaggtc attttcacag ttgggtgagg 11820
acacacttca gaagtgagat gagctacagc tgctagctgg ctctctcctg ggatgtgtac 11880

```
ttagatccct ttcttgttgg tcccaaagac tacctgtacc caggacctga aaattttaat  11940
ctaagtcatc taatgagtgg aaagaactac agcatcccct tgtaatggta ggtaagagat  12000
atcttgtaag ttttgggttg atttgctgat caatggttcc ttgggcctaa ccccatattg  12060
ttaagctcca aacaaaagaa aggactgttt cccagttgct tgtggcttct tggtccatga  12120
agttctgctg aaatggaccc tgggcaagga aaaaaaaagg gaagttatag agcggaggaa  12180
gcgtaagctg cccctagacg tgagcccaga attttacaag caagtataga agctggcctt  12240
tgaacaagga ccttgaagag tgagaaaaaa gggatcccaa aggaatggag gcttattgtg  12300
cagatgaata ctgattatgg ccatgttcac aaagtacact gcaacacctc aacagtgtaa  12360
aatctcacta atacataccc cactaattca gccttctcaa ctctctggaa tatgtggcct  12420
tttgggtaaa gccagggcta aaattcactt ttgtgctatc tccaaaaatg aagttgggct  12480
aaacaaatag aaaggacagg ctgctattaa agtcactggg gaagcccgtg actctttaag  12540
ttcataatca gacatgatag tatccacctc attaaatgcc ccattatggg caggaccatc  12600
tctctggctc agcttgtttc ctatttgctt cctctcgtgg taccttaggt ctgcatctat  12660
gacattgacc ttgtttctcc tctcctcttt tctctctctc tcttttttt  ttttttttt  12720
tttttgagac agagtcttgc tcagtcaccc aggctggagt gcagtggcgc tatctcagct  12780
cactgcaaga tccgcctccc aggttcacac cattctcctg cctcagcctc ccgagtagct  12840
gggactacag gcacctgcca ccacacccgg ctaattttt  ttgtattttt agtagagaca  12900
gggtttcacc atgttagcca gtatggtctt gatctcctga cctcgtgatc tacccgcctc  12960
agcctcccaa agtgctggga ttacaggcgt gagacaccac gcccggctct tttctctttt  13020
tatctaaatt attcattcat catttatgca atagatattg tgctccttct ataactcaag  13080
catgtgctaa atgctggagt tacaacaagt aaatacggaa cgtttgctct cagggaggtc  13140
atagtctaat g                                                       13151
```

<210> SEQ ID NO 7
<211> LENGTH: 12693
<212> TYPE: DNA
<213> ORGANISM: Homo sapiens

<400> SEQUENCE: 7

```
cctttttagg cctgatctca aatatataat tggcatagat agtcttagct tctggcagaa     60
cccttacatt agcaacttga cttgtagagt ctggtaggaa aagtcaagtg gaagtccttg    120
aaactacacc ctttcctcca cttcaaggca gtagatcaga agcaaaatca cctctcagaa    180
agtattgcag ggttagaac  ccctatcatg acttaaatga tgcagggtat ggtagatccc    240
attacatttc aattaattag cttgtatagg cccctgcgaa agccaaatct attatcagat    300
gatagtggat ttccaaaaat cagatgatag tggatttcca taaacttggc cagatggtag    360
catccattgc agctgccatg ccaaatacgg tatctttact ggaatatacc aacatagcct    420
ttggtgtgtg ggatgcagag tgacctggca aagtggaatc acaaggaaga taaaaaccag    480
ttcactttta catggcagat acagtagtat atattcactg ttttgcccca ggagtatcat    540
aacagctctt tgttataata tagtccataa ggaccttgtc attccaacat gccatggact    600
atcctgctgg tcccttatac tggtgacatc atgctgactg aagatagtga gcaggaaggg    660
acaattgcct tagatactct gttaagatgc atgaataggt cagaagctga gagataagct    720
ccatcacctg tctcatcctg ggttattcag atagtagcat ctgaggctaa gtcttgtgtg    780
```

```
cctctatggc attagggagt gtgatcttag agagcagaag tgaaaaggaa agggaggcga    840
ggtaggagga agagcccaat aagaggcaat agacatgacg gactgctctg caagcattgt    900
gtgaccatct tctgagatgc cttataaatt actttcttgg cacagtgcat ctggaagagg    960
aagggagaaa aatacatcta ctggcttcca ttggctgaaa ttttgcccca cagggtgtta   1020
tttgcactgt acttccaggt tgctcattgc aggcactaag gatagtgctg aggatgtcat   1080
gccttagcat caacagggaa gccctggggt ggaagtgaaa ggtgatcaat gtggacatga   1140
ggccaggggc tgtgagttgt atctgcctga agttggtgag agtccaggta gagttggtct   1200
ccacaaaggg gactgctgtt agaacaagtg gccagagacc ctggagacgg gtgagactaa   1260
aagaatttca agcagctatc ttaatttgga ttcccgcagc aaaagactca gaggcaagga   1320
ttccactgcc agcagttcac ttggtcagtt ttcttaagaa gcactggaag gggagtgggg   1380
aaatgaggtg gccaataaag agtgagtgca caatacccct gtgggaaacc ggagctcagt   1440
cctgtggaaa ctctggatag aagtatagaa tgtgtgcctg cctaggtgtt cccaccagct   1500
gggtaagggg gctgagattc tcatccacca gctcctgacc atcactgatt gagagctgct   1560
tggggaaggg gttgctccat taatttccca acacttctgg tcttctgtgc ttgtgggcag   1620
agcaggctcc aggggccaga gaaagcgctc aggtgaaggg atgcaggtgc tggcagttgg   1680
aagacagcca ccctgcacat aaatgatcaa gatggagggg atctggacag gatgttgcag   1740
tggcacataa aaggtgtctg atacattctc cctccttttt cttttcctct tggattgtca   1800
gattttcaaa tccatcattt tctcttatgt tgaaccaatg actcttgtct cagcctgtgg   1860
cccctctttg catatccaaa cacatcaaga tgctcagcag aacaaatgag tcctccttgg   1920
aaggtagttg tgggcttaaa cagtcattat tttctcttgg ttatcccaaa ggcagctatc   1980
tctttagtta ttctagtaaa ttctattcta gttagctagt taaatctatt gcactttttc   2040
tgcacattaa atcagatgat atgcaagctc taactacctc ctgtagacgt tctcatcaca   2100
actccacaag ggaggcattg tacccatgta gtgaataaac tgaggtctag aatgacatgc   2160
actatattct tggtaacttc ttcagaaacc aaagttttag atgatttcca cagatttttg   2220
tgccccttcc agctgcttga gacagtatgg agaatgcttt tggatattga gttatcaggg   2280
acattgggta gattatggga aaatggaaca gcctattaat ttagtccagt tctgtaagag   2340
ttgggacata agatccccag tcttcacaca tcccaatctc acagattaca ctgaacggtg   2400
gtaaacaatt tagatcagct tgggtatgac acgaagcttc ctcttggcta tttctacaac   2460
ttaacattga atggaaggaa atcacttaag ccctaaaaac actgtctggc aggaggtaaa   2520
atgtcttgct tggcttcctg ccccatccct cccacaccca cagctgggac catttggccc   2580
ccacttcagc tcccaggcct gagaccctcc ctgttcttca tctgcctgag ttcagggaca   2640
agctgcaaac tgagagccct tcttgaatat gaacatggtc tggcttccca ggagaaatag   2700
gtgcaaaatc aacaacctta acacgagtct atttccagtc atttgtagat gagaagtgtg   2760
ctttgggaaa cttcattttt agattccagt gaattgggta tcatcagtta cagagaacca   2820
acaaaatatg aaatgtgcac ataggacttc cctgcaagag tagaaaggaa tctgttgcct   2880
tatgcatatg tatcttggac tgataaattg gatcacaatc aagtcttcac ccttcatgtt   2940
atatatgtaa ctgaggaggc caggtttgtt tcataatggc accttcattt ttattttttt   3000
caatgtacac actttatttg tatattaaac aagtagaaat atgtttttcc ccatctttct   3060
ttaaacatgt tcttctcccc atatatcttc tgtttaccca tttttaacag gaacatgagc   3120
attcaaccta ttccattttt tcttatatgc aaaggcagag tgcaactgtg ataggggcaa   3180
```

```
ttgattctta gctttggttt tggggacaat atggggtggt gggaactacg gcaaactgga   3240
cagtactgcc ttagctgaag gcagcagccc ctattcaatg ccaatcaatt gttggcacag   3300
agaatgcagg ccttatgtcg ccaggttttc caaaatttca aaaagaatcc agaagtctca   3360
attttactgt gcaattctct aattatcaaa tattgctagc caatttaatt tggaggttga   3420
cacccagcag accagataaa acatatctat gggcaaaatt gaaggctggg catggtggct   3480
tatgccttta atcccagcac tttagaaggc tgagatgggt ggatcaactt gaggtcagga   3540
gtttgagacc agcctggcca acatggtgaa accccgtctc tactaaaaat acaaaaatta   3600
gccgagtgtg gtgatgggcg cctatagtcc cagctacttg gaaggctgaa gaggagaatc   3660
acttgaaccc gggaggcgga agttgcagtg agccaccatt gcactccatc ctgggtgaca   3720
gagcggcact ccatcctggg tgacagagcg acactccatc tcaaacaaaa acaaaaacca   3780
aaatcaaaaa tgaaacaaaa ttgagcctat ggctgccagt tcacaatctc tggttttaaa   3840
actgtcaaac agaaccctag atctactatg tagccataac tgatgtggtt tttctaagca   3900
gtatagaaat atagttctaa gaaagtcaat tatattccta gttaatgtgg tactttacaa   3960
acaatagaga aatatagaat tatgaaagca aattccctat ggttagtgaa tcaaaataaa   4020
ataaggttag gcccatcaca gagtggctgc aagtgggaga gaatttacat tcacagggaa   4080
tgtgaacaga ttaggaaaga ggcctcaagt ggacaatttt gtcgggatgc agttcgcctt   4140
atgtgttagc tccacatgag gccaacctgg ttctcgagct gctttggcta ctggagcctc   4200
aatcccttaa gaggttgatc tagggtcccc cctctgtctt gccagttgtc cccctccaca   4260
ggccgcagcc ccgatgagaa tatccacaac ctctaataat agaagccaaa atccaatgga   4320
cagagagcac tgtggtgtac cagtaggtgg tcccatcaag ggactcacag ccaccattca   4380
attcaaggta gttgtgtcca ttatccaggt ggagaaataa aaaatcagac caagggcaag   4440
atttgcccaa cttcaccctg cagccagggc cagcattgga ctggaaccca gactcctgat   4500
ctccaggcca accatccctc ctctgagccc tcaccgccca ggctggcatg aaccctttca   4560
tatccgagtg ctctgtgtct ccactgcgat tttgctcttg agggtggaga gtgagtctaa   4620
tcttcttgct tactggcagg cagcatggct gagtggggag gagcatgggt gttgcatctg   4680
ccattcatta gccttggaat gttttgaacc tcagctttct tatctatgaa atggggatca   4740
tgacagtatc acctttccat ggctgttgtg ggtattaaat gagataacac agctaaagca   4800
tttagcagag ggcttgggac ataatccaca ccaagtaagc attagttgct tatatccatt   4860
cccatgccat ctcctctgca aggctaactc acttggcaag aggtgaccca tcctctagag   4920
tggaactgaa tcaaacacag gaactgacca cagagccacg gcccactgtg gctacttggt   4980
gcttcaggaa gagaggtttc tagtgtttac ctggcttcag agctgtccag gtctcagcca   5040
acttcagcgg tgcctcttct cactccaaga tctcacacta tgtgccgggt ggtaatctta   5100
ataaaaagcg accattgagg gtttacccag tgccctgcga taagctctgc acagatgggt   5160
tagtctgccc tgaaccgcct cactcccact gagggctttc ggaggcagag cctggttcat   5220
gacccccaca tctcatcaca gggcctggtg tgatgcctca cccaagactg tgctccttca   5280
ttcatccagc gtttattggc atctcctact acctgagctg ttttaggcag ggaacaaagc   5340
acagataagc cctcctggag cttacattct gatgaagggg gcaggcaagg tatacatagg   5400
gaggaaagcc ctggaatcca gtacattaaa aacttttatt aggattatct ctgctgcatt   5460
tagttgtatg tatcccttat ggcccccagg caggtccact cctgggcatt caagtcggtc   5520
```

catgtgtcag gcgtgcaggg tggtcacag catctaggag ctcagtgcag cttgggactt 5580
tgggacatac gctccacctc tctgagcctc agtctccttg tccatcatat aaggaaatca 5640
ctgattccag ccttcctggg ctgtggagag gattccctca gcggctgtga aagagtgctt 5700
tcttgcgggt cagccccgac aggacagact taagggcggg agggagccca tcccgcttgc 5760
cccaacgaac gcgggcgcgg ggctttcctc gcaggttaca taaggcagcc gcgggtggag 5820
gcagcagagg cgagcgcacg tccgtcgagg gggaaagggg cgtggggagg cggccggggc 5880
ggccggtatc ccccgggcgt gagtgcgcag cgcgcggggg agcgcagggc gcggcggagt 5940
cgggtttcag agcgcgggtg actcggggcg cgggccggga gccgggattc tgcccgccgc 6000
cgccgctgcc gagcgccgcc tttgttccct gcaggaaggg cgagcgcggc ggccagcgct 6060
cagcgaccct tcgtcctccg ctaagctcca acgctctgct cgactagccg cgcgccttcc 6120
ggggctccgc agacccgcga gatggcacca aggtaagacc cgcttctctg cttcctcgcg 6180
tcccgggccc ctccaatact cttgcccgcc tcacctttc tccctcgggc acatcttgca 6240
ggaggaacaa cgggcagtgc tggtgtctgc tgatgctgct ctcggtctcc acgcccctcc 6300
ctgctgtcac ccagacccgc ggtgcgacag gtaagcaacc cggtcggagg gtggcaccgg 6360
ctgcctccgc gcccgtgggg gaagtcggtt ttggcggcgg acgcggctgc gatgcgtgcc 6420
tcattcctgg acataaaagg gagtcttgcc actcagtgcg cactggcggt cccgcgggcg 6480
gctacctcct ggcagtgcag gggttatagc tgtgaatggg atccctgggc agctggggcg 6540
gttggagcgt tgtctgggca cccgagatgt ctgagctggg tgcggagcct ccaatcttag 6600
gcagagaggg acttcagaaa cagcgccagc gccagcgcca acagcctcag cgcacccagc 6660
gccagcagct taggttgtgc gtgctggctg gcttctggta agggcaggtc tggtgcctct 6720
ccgcacacag gtgcgaagca tgaacaccgg gagggacatc tggggctttt gctgctcaag 6780
aaataacgga actgaattgc tcggttgctt aacccagctc tgagttacct aagcggtcac 6840
gtctatcatg ggcagtggct ccaccggtgg tggaaagagc tgtggcctgg aagccagaga 6900
tctgatccct tccgttcccc gggcctcagt ttctccagca gaactcaggc ggttggctga 6960
atagtaagat ataagttaaa gtagacctaa gttaaaatgg gcctcggtta aggtcagact 7020
gcctgggttt gaactgtggc tggctgagtg atcttgggca atggatttca tcgctctgtg 7080
cctcagtttc cccatctgaa aaaggcgatt aattagacca ttttaccttc ctagaaatgt 7140
tgtgaatatt agagaaatta gaaataatgt gcttcccatg attccagtat atactaggca 7200
caaaataagt gatagaaatt actgcttgat tcttgcagta actatgtgtt ggaaagcaat 7260
gcaagtattt ttatttttat tttagattca gggagtggtc atgtgtggtt ttttacaagg 7320
gtatattgca cggtgctgag gtttgggctt ctattaatcc catcgcaatg caggtatttt 7380
tataacattg aggttgagag aagcttagaa agtggccagt ccaaaagcca ggacttgaat 7440
ccaggtctgt aggctcttgc ccttgctcag ctctttctcc atgcagtttt gcagaagagc 7500
catgctttct atagcttctg acccccctccc ctttgaattt gggggattag tacacatctt 7560
caattgaata agggaacaga aagtctagga aacaacctct agtcggccca aaggaaacgg 7620
gattgagaag gtggccttgg ttaactcttt gtttgcctga agaagcccaa gacagcccat 7680
tgtctcctgg gcaacaagac ccaaatccga tgatagcttt tcctgccaga gtgtccagcc 7740
tggcatttat tgcagatcaa agggcagctg gagtatagtt ttagcttctc agccccatgg 7800
ctcatgtcag aaagttgcaa ttttgcatat gatatagggc cctgccaact cagtggcaga 7860
ggccaacttt gggttccatg gtcttttgtg aactttgctg caacttccag tttcccaaaa 7920

```
ggaagatgga tctggggata ggaactttgg tgtttctttc tcctcctgtg tgtgtctctg   7980
ggatccctca gtgtcagggc tgttgtttct aacacaaagg aagccctatt cccatttata   8040
atgtaaaaag ggagggccag caaaccttca ggagctgaga acggtctaag gagggccatt   8100
tgcaactgat gggttttcag tgcccctttg gggatgtgaa acgattccta aaaatgtaaa   8160
ctatcctcct gcaaactgca tttgtaatgc aatttaatat ccctaatact tataaaacac   8220
tttgtatatc caggtggagg tgtgaacatg ttcatatttc attcatccaa tccttacaac   8280
cactccagga ggtgaggact gagaacagtt actatctctg tttttcagat gaagaaacag   8340
aggtccaaag tcacaagact tctaagtggc tggggtggga tttgaaccag acagtctgac   8400
tccagagtcc ttgctcttaa ccatcctagt gtgtagttag aagagcttca cggatggaga   8460
aggctttagg ggttccatgg tctccaatga gccccacaat ctgaatgtca caattgtaac   8520
atgagtccat tgcatggcat tgtgcagtct tcaaagcaca atgtcacctt caccacgtcc   8580
ctggaatcac cacccagcag tgctgagaag taaattgggc tctgtcttac agaggggatg   8640
tgacttcctc aaggccgcat gactgtaact gggtagatcc ataatagccc tctcacgtct   8700
gtgaacttct gggctggtgc tgttccttcc ataggaccac tgcccaactg gctataaaaa   8760
acaattgcca agacttcata gcactatgaa ccagcagtgt tttaagtgcc ctgccatgaa   8820
tgagctcagt caatcatcac aacaacccca tgtcttatcc ccttttacag atgaggaaac   8880
tgaggcacag tcttttgccc aagggcatgt agccttcagt aatataagca caatttgagc   8940
ccagagggtc tgactccaga atctgtactt gtaaccacta tgctgtatgc ttaagtgggg   9000
tggcttctga aagcatgttt gtaagtgggc tgttatgagc ggaaatacat gttcccaacg   9060
atttggcagt ttcttaaaat gttaaatata tacttaccct acaatctaga acttccactc   9120
ctaagtatct acttaaggga aaggaaagca tatggccacc caaaaactca tatgtatgtt   9180
catagcagca ttatttataa tgaccaaaac tggaaataaa gttaaattca ccattagctg   9240
gtgaatagat aaacaaatga ggtgtatcca tttaatggaa tactactcag caataaaaag   9300
gaatgaagta ttgatcaatg ctacaacaac atggataaac cttaatacca ttaagctaag   9360
taaaagaagc cagacattaa aaagcaatac attgtaagag tccctatata tgagatttct   9420
gtaaaggcag aaccacagag acagaaaaca gaagcagaga ttgactgcaa aggggcatga   9480
ggaaactttt tggggagtgt tctaaaactg gattgtggtg gtagttgtgc aactctataa   9540
atttactaaa ataatctaac tatacattta aaatgggtga attttatgga atgtaagcta   9600
tgcctcaata aagctgcttc ttaaataaaa gaatgtattt tcccagagca tctaggcccc   9660
agatctggtg gggcttcaag gtggggttcc tagccagcct ggtacagagc tggcacacag   9720
ctcacaactt aaaagctgct ggcctcttag ggcattgatt ctctcagaaa atgggtccag   9780
agttctgcct gcacctccag gtctctggat cgactctccc tactatccct gaatgccatt   9840
gtgggcccag gacagggctc ctcaggtagg ggtagaacac atgcatatgg gttttttgca   9900
ggtagttgat ctgttaaaaa gtgggtcttt gtaaacttcc tgatatcctg cacgccctaa   9960
aacagcacaa gttcaggtat tggaaaacct gggttccact cactgacttc ctccatgaac  10020
ttagatgagt tgcttttccc actctgagcc tgttttccca tctacgaagt ggagaggcaa  10080
gagtcactca tctctgtagt cctaatttaa aatgttggga aacaaaacaa aataatattt  10140
ttctagtttg aggtttgatt atttcacata gtttagttca acaaacccat tctgtgctgg  10200
ccctcatgct ggctgggtac agaaaggatt tgggcacaga gctgccccaa aggggtcata  10260
```

```
gttcacagga agaaagaaag ggccacagac aactgtaatg ccatttttcc tgaagtcttc  10320
tcatctacca tgcagaatgt cctgtgtgca gccaatccca tccttctaca ccatcctgtt  10380
taaagacaca cttgtcggcc gggcgcggtg gctcacacct gtaatcccag cactttggga  10440
ggctggggcg ggcagatcat taggtcagga gattgagacc atcctagcta acacggtgaa  10500
accctgtctc tactaaaaat acaaaaaatt agccaggcat ggtggcgggc gcctgtagtc  10560
ccagctactt gggaggctga ggcaggagaa tagcttgaac ctgggaggcg gaggttgcag  10620
tgagccaaga tcgcgccact gcactccagc ctggcaacag agggagactc tgtctcaaaa  10680
aaaaaaaaaa aaaaaaagag acacttgtca gtgggtgtca cccacatggc ctcttgtacc  10740
tccaatggtc agggttgagc tggaggacaa caccaatcct tccttttcct ggtaaagttt  10800
cagggtcatt ggaataccca atattttaga agataagggg gctattgtcc aggtagggat  10860
ggtggtgtca caagtaattt gctcttgcta ataaagtgtt gatgattgca aattatttgc  10920
ttatgtttaa actgttttat tgtgaaatac aacatccatt cagaaaagtg catgctaaag  10980
gtacagtaca atcttgtatc acagagcaaa catgtaatcc agatgaagat ataggataat  11040
ccccagaagg tctcctaaac ccctttgctg tggttttatt ttcccttctt tctctctgag  11100
gtaaccatta ccttgacatt aacagtcatc cctttcttgc tttttaaaaa tagctttact  11160
atctaagtgt gtatcccaaa attctgaagt tctgttttac tcgattttga actttttaaa  11220
tgcagaatct attctttcat gtctgattct ttcaatgaat aataagtttt tgagatttat  11280
tcatgctgct gtatgtggct gtagttcatt gccattgctg tataatagtc cattgcatta  11340
gcatagcata tgttacttat ccattcttct ccaacatttg ggttgtttcc attttgggct  11400
aatgtaatag tgtcgctctg aacattcttg tacatttctc tcagtgcaca tgtgcatgaa  11460
tttctgttgg ttctatacct acgagtggag tgctgaatca gagtgtgcat atccccccaac  11520
tgagtagaca atgccagcat gtcttctaaa tggttgtaca gatccacaca gctaccaaga  11580
aatgagggcc tccatttctt cacatcctca ccagcacttg atcttgtcac tgagcttaac  11640
ttcagcattt ctaatgggtg catatttgat cttactgtag ccttaatttc cattttccta  11700
attattaatt accttttcat atgtttattg accatttaga tatccagact tactttttat  11760
tgaggtgaaa tttacattat ataacagtaa ccattttgaa gtgcacaatt cagtgtcatt  11820
tagttccttc acaatattgt gcaatcaaca tctctatcaa gttccaaaac attttcatca  11880
ccccaaaaga aatatctatg cccattaatc aattgctccc cattccctca ttttctcagc  11940
ttcaggcagt cactaaacta ctttctgcct ctatggactt gcctattcta gatatttcat  12000
gaaaatggaa tcatacagtg tatgacctat tgtgtctgac ttcttccatt taacataaag  12060
ttttcatggt tcactcatgt tgtatcatgt gtcagtactt catgcctttt tatgactgag  12120
taatattcca gtgtatgtat ataccaaatt ttgtttttcc attcatttgt tgatggacat  12180
ttgggttatt tctacctttt gttttttgtg aatagtgctg ctctgaacat ttgcatacaa  12240
gtattcggat gcttgacggc ctgtttctac ttctttgcac ctaggagcag aatttctggt  12300
catatgataa ttctgtgttt caagtatgac gaacccccaa actgttttcc acagtggctg  12360
caccatgttt acatccccac cagcaatgta tgagggcttt aattatgcac atcatcgcca  12420
atgcttgttt tcagttttta aaattatagc cattttagtg gatataaaat ggcatctcat  12480
tgtggttttt atttgcaatt ctttctttct ttctttttc tttctccttc cttccctcct  12540
tccttccctc cctcccttcc ctccttcctt ccctccctcc cttccttcct tccttccctt  12600
cccttccttc cttcccttcc cttcccttcc ccttccttcc ttccttcctt ccttccttcc  12660
```

ttccttcctt cctccctccc tccctctctc tct 12693

<210> SEQ ID NO 8
<211> LENGTH: 12803
<212> TYPE: DNA
<213> ORGANISM: Homo sapiens

<400> SEQUENCE: 8
gaagcagatt gttgaggcct gtccataaat tcctcacttg aacctgtagt gactaattct 60
ctcgggagtg tgggatcaaa cccaccatgg ctattaagaa tttaatatga agccccagtg 120
cctggggccg tgctttctca tcagccccga aacagggcga agcctgcatg tcaggcgggg 180
ccaagaatgc aaagtctgga gtccctttcc tgagaagctt cctgggacag cagccttccc 240
tctggggaaa ttctcagggg accttctgaa caagaagtgt ctttttttcct gcaccagtcc 300
taatcataga caaagtggga agccccttgg cagagagaag tctggataaa caccacctcc 360
tggcaatgta cccttgcccc taacatctcc cacgtacaac tgacactcca cccttcatgt 420
acaacaggct cccagtctcc aaaggtcttt gtgaacgcag cgtgacccac agaaaaagaa 480
gcagaggtgg ggggtggtgg aggaggttgg gggaacagat ccagtctatt ggtgaatttt 540
aagcaatgaa catatttttg acctgagaaa gtggtcagag tgcatcaaat tgagagcctg 600
ggctcctgca gccagtgagg gggcagaggc ccaggaagag ggctctgggt gacccgggac 660
agcagtgggt gatggggcaa agctgtctca cctactgggc ttggttactc atgggactga 720
tgggactatc agagagcatg tggcttgtga acccaggaat gccttcttga aacagcctcc 780
catccttcct gtgagatccc tgagagagat gaagcttcag ggacaattta gtgactgagt 840
gccactccgc ctgggattgt gttaggcact taatgtgaca aataaaatac acacggttcc 900
tcccctcaag ggcagtgaca ggtgagaaat acggaggtca tcctattatt tcagatgtgc 960
ctgaatccca aagttgagct ctttggcaaa ccagagcccc acaggatccc cgggccgtgt 1020
ttgtaattta ctagacatgt accaactgca tcccacatat ctgtccgtcc ctcacaagtg 1080
catctcaccc atcagagagt gctcacagct ctacctccga gacacatgcc ctgaatttca 1140
ccacttcttt cagcccctcg ccctacaccc agtcaccact ttttctttcc tggatgactg 1200
ttcttgtagt ctcttctcca aggagcagcc agagtgattt gctctaagat agtaagtcac 1260
tctcctgcta aaaccctcca tggacttccc atggccctta gtgggaaacg cacactccct 1320
accatggccc ctggacaaga ctttcgccat ctgtctcctg cccacaggac gtccttcccc 1380
tccactttgc cccttatgca cacgccttct ttccactaca agaagatgac gcacttgttt 1440
gtttccctgg gtctctgaaa ttgttgctcc tccttggaat gtttgctccc agcttcccat 1500
ccttcagatt tcagctcaaa agtcacttcc tcgcagaggt cctccttgac aacactaacc 1560
aaacccctgc atcactcatt gcccatcata ttcccttact tttatgtgca gagcacttat 1620
caataacaga aatcatctta tttctttgtg tgtatgttta ctgcctgtca gtctcctccc 1680
gccatgcccc ttgaggttcg tgtttctctt ttatttcctt actactttct acttagcacc 1740
cagagctcag tgcatagtag agtctccaaa catctttgtg gcctcattca ttgactagca 1800
caatgctcag acatcaaata tccatgtgaa aagagcatag agattgaatc catctactca 1860
cttgtcagag gggaaaatgg agattccaag agggactggg acttgcccac agccatacaa 1920
ttccttcatt tattcatatc agctgataca tgcaggataa gaaggaggta tccgtttgaa 1980
gatatggggg gaagagctag tgcaaagggc ctgaggcacg acctttacgg gaaagcaggc 2040

-continued aggaggtgag tgtaacagag caatccaagg aggagaggtg tgaggggagg tggccaggca 2100
ggcagaagcc aggccatgca ttcgcaactt ggatttagtt ccctctaaac caggggtgtg 2160
aatttctctg cccacttgtg taagatgctc agacagcatg ggacctggga gactagttgg 2220
gcacccataa gaagccaaga gtgaagatcc tgtggttgag caagtcccat gggtgtgttt 2280
gccaggacat caaaggtgct gcaggcagcg gcagccgcct gtctgagctc cattaccgtg 2340
tgggaactgc acaggaccca cccagttagt atgagtgcag tactcgctgt gcaattacgg 2400
ctgctactgc tggctgacca cgtgccaaat cgctgcacag ttagttactc atgccacagg 2460
ctttggacca attaagtgag caaagagggt ggttaacgag gagtaaacaa tccaaatgcc 2520
catgattaca ctgaggcttt gctctaatgc atccaagcca ggagatgagg atgggcagca 2580
gggaacatgg ggtctcctgt cctttgtttt gtatggttgg cccactgaaa tctctttcac 2640
ccagcccacc ctgtcccata ctctgctatc actgtctgct gattattttt ttcttgtctc 2700
ctcccctcgc ttttttttt tttggtggag gggcgtgtgt gtgccaagtt ctaagcactg 2760
agattacagc aaaacaaagc agcacttatg gaactgacat tttaaagtca aacaatcagg 2820
taaatcaata tgatgcatca ggtggtaata catgctatga agaacactga tgctgggtaa 2880
gaggaataga gagctctcag ggcatgggtg ctaattcata tagtgagtct agagaaggcc 2940
tttttgggtg agtgcagtgg ctcctgcctg taatcccaga atttggggaa gctgaagcaa 3000
gagggtcact tgagcccagg agtttgagac ctcctgggca atatagcacg acctcatctc 3060
tacaaaaaat atatgctttt taaggctggg tatggtggct cccacttgta atcctagcac 3120
tttgggagcc cgaggcgggc agatcacttg aagtcaggag cccaagacca gcctagccaa 3180
catggtgaaa ccacacctct actaaaaata caaaaaaaaa aaaaaaaaaa ttagccacgc 3240
gtggtggcac gtacctatag tcccagctac tcaggggggct gaggcaggag aatcacttga 3300
acccgggaca cagaggctgc agtgagctga gatctcgcca ctgcactcca gcgtgggtga 3360
cagagtgaga ctccatctaa aatatgtata tatatattat atatatatat atgttagctg 3420
ggcatggtgg tgcatgcctg tgtcttagct atatgggagg ctgaggcagg aggattgctt 3480
gagcccagga gggtcaaggc tgcagtgagc tatgatcaca ccattgcact gcagcctggg 3540
caacagagtg aggccctgtc taaaaataaa aacttttttt aaaataaagg tttttttgat 3600
aaagtgacac ttgaacagag acctctctga aggaagtcag ggagccagcc atgcagtcgc 3660
tggggaaggg catcgcatgc aaagggaatg gccggtacaa aggccctgag atttctgttt 3720
gcaggggtag accagtgtga ctggagcaga gttagcagta tcgtaggatg atttgggatt 3780
atacagctac agggaaggat gagggcaggt tccaagtatg gagaacagca ttctcgaaag 3840
cctccagcga tgacaagtgc tttctgtttt tcaaagtatt ttacctcatt tgatcctcag 3900
aacaatactg taagggtaag aaggatagat ttcttttttct attgactgct gaggaccgaa 3960
gctctagaat gtctaacagt tcagccagga tcacatagga atattccgat tcagaggcag 4020
aaatctgtgg tctgcactat gctttcaggt cagattagag gctcattcct tttgacacca 4080
tgccattgtg agcttccaaa acaagatccg ctctcaggca agcctctgaa tgggttacaa 4140
agttcaaaat ggagccaagc acaagaagag ttgccaagag tgatacagaa cgctctgtgg 4200
ggagctggtg tggaaaatca gcacacccag cgcctgtagt aatttaacca atacagcaga 4260
aaaacgtagc ttgcgtgtct ttcgaagaaa cctttacaga aaccctgaaa agctagaatc 4320
ctccctgtgt ctgatcataa tttaatattt ctggaataaa atccttctag aatatatgtc 4380
ctttagaatt cctccaagaa gcttcctatg gagctccaga taaagaggac aatctaaaag 4440
ttaatatgaa agattaaatt aaaaatgcca tccagaaaac aagattcccc tgcaagggac 4500
gcatataaca gattttgcaa atgtgtggta gatcttactc ctgccatcag cacctactga 4560
attcccgatg ctattgttat cgtcattttc actacttagt ttctagtggc cacaacatca 4620
actgagagtg acttgatggg ctgtcaccaa atttggaagg aatgtttgca aacatttgta 4680
taaatgtagg aaacaaaatt tactttgcag ggctcaggtg ggagtgcgtc ccaaattgcg 4740
agggagtcat cttagacact ggaggggctg ctgaccaaga gaggcctgcc atagctctca 4800
ggaagctgta gaaagtgaag tacagagata gattcaaaat ttaagtccca tattgcaagt 4860
cacaaagaca gatgctctga atcaccagca ctgattttcg agggagctgg ttctgacacg 4920
ggctgctctg tgcacagtcc agaaatctat gacttcatca tgttaatgag actggcagtc 4980
aacgctggga ccacacctca agtgggcttc tcctggagca ttagctccca catgccaaag 5040
agcggggagc gtttcccttt aggcttatgc ggcagttctc aagccactcg atctcaggac 5100
ccctttacac tctgtcttta tcaggaatcg aaactgagaa gatggccggg tgcggtggct 5160
cacacctgta atcccagcac tttgggaggc ggagcggggg ggtgcgcaga tcacctgagg 5220
tcaggagttc aagaccagcc tggccaacat ggcgaaaccc catctttact aaaaatacaa 5280
aattggccaa gcatggtggt gcatacctgt agtcccagct actcgggagg ctgagccagg 5340
agaatcgcct gaacctggga ggtagagggt gcagtgagca gagatcacgc cattgcactc 5400
cagcctgggc aacaagtgcg aaactccatc tcgaaagaaa aaaaaaaaaa actaagaaga 5460
gtgttctaaa tatttacgtg gtagtttaca tactgggtac aattgtatac tgcttgggtg 5520
acggtgcact aaaatctcag acatcatcac tatacagttc atccatgtaa ccaaaaaccc 5580
ttgttagccc aaagttattg aaataaaaat aaataaacaa taaataataa ataaatattt 5640
atgtggtaat ttatttaaaa ataacaataa gcccactaca tgtttcacat aatcatagta 5700
ttttcttttt ctttttggag acagggtctg actctgtcac ccaggctgga gtgtggtggc 5760
acaatcatag ctcactgcag ccttgacctc ctgggcctga gccatcctcc cacctcagcc 5820
tctcgagtgg atggggctac aggtgcacac caccacgtcc tgaacaatac tttcgaagta 5880
aaaaaaatcg taagtgtggc gttgttttac atgtttgcaa atgtcttaaa cagacacctg 5940
gattctccta gctgcttatt atgatatcat aaggatgcag cctctggaaa atgccactga 6000
gcactcggga gagcatgaga gcaatacggt aaatgtgttc ttggtaacta tcatgaaaaa 6060
tattttgacc tcatggacca tgtacaaggg ttatgagacc gtcccgacag ggatccccag 6120
accactccat gaaaacctta gtataatggt ggaagccaaa ttgttgggga ctttgggcat 6180
attgttaaac ctcttcatgc ctcaattttc ttgcctataa aatgtagata gtaataactg 6240
tcctcataag gctcttgtga caataaaatg acttaatatg ggtaaagtgc ctgacacata 6300
gtaacagctc aataaatgct ggctagtatt atgaaccgct caagagccaa gtccatgggt 6360
tcattgttcc cccaaagcag agaatgggga aggcgtgcag gaatctttca ggaataagtg 6420
caggcacatg tgaacaactc tctcagtgag aggactttcc taggacaggg aaaagtcttt 6480
tttttttttt tttttttgcc cctattaaat aagctaaaca gatcagagag gccatgtgac 6540
tcatcaaagt cactcagcgg gtcctgtgtg tagctgctgt agctgagaat ggccctcccg 6600
cacctcccca ccccacacta ccctctgcat ccaaactcat ccgagcacac tagggatgga 6660
ggtcctggag catcgatttt gtcctgttgt ggaacatacc tcatgtgcag tctcaggggc 6720
caaacgaggt ctacagaacg ctgtagctta agacatccaa gctctctcct ccctctgtca 6780
tgccatctag aacacacttc taaattgtaa ttacatacta acttatgtga ttactcactg 6840
acttcccctc cttagtcctg ggaccctctc agtctttttg gtttcaatgg ctgtcatgtc 6900
agggatgtgg cagaaactct atcaatattt agatgtctgt tttaggaaag aaggaagaaa 6960
taaaaccatg tgttttcatt gatgaaaaga aagcaagcaa cagacagctg aatgttttct 7020
gtagataatt aggtgtttga gatagtgcag aaaggaggag agtacggtaa aatgttaaaa 7080
cagaaaatca accaagagtt aaggtgtttg tctaccaaga gtgctggttc tgcttagttt 7140
tagaaacaat aacaacaatg ataaggacaa gaagggctca cggttactga cagcttaccg 7200
tgggcctggc atggcgctaa gcattctgca tgtatcgtct cactgaacgc tccttatctg 7260
ctgtgatgtt atttccattt tacacagtgc ttgaatgact ccagaagtcc cacagccagt 7320
gagtaacaca gtgcatcatg gaggtgggtc atccttggaa ggcctggggc atggaataca 7380
agctggagaa ggtggaagga ggctgggatg agatggtggc aggttgaggt gccaggcaga 7440
agagtaggcc tgagtgcagg tgctagaagt tcagcgtttc tggggctggg cacaggtgag 7500
caagataaaa tgctgctgat ttcttaattg tggcaccaga cactgactgg ggcaccaggc 7560
acagagctgg agcacaccat attttataaa aagaaatact aaggctcaga gggagaaaag 7620
gccttgccca aggtcaccca acaagttaga gcccagccca gtcttgctcc cagtccaggg 7680
attttggcac tgcaacaagt gcccctcttc tgactaacag actcacacgc ttcccccatg 7740
gcaggctccc ctggtccctg gctccctgca gagaggatgg cgtgggaagg gagcaaagca 7800
gcaggcttca ttccaggatt cccctcccag ggcaggaagg agagggctgt ggggcatgac 7860
caggcctgct gtggctgact aggggttctc caccagcccc ccaaacccag aacaaagcaa 7920
ggttaatgag agcaaattac aaaggctctg aaaatggaag ggaccctttg aaggctgcaa 7980
gggtgagagc tggggtggga ccagcctgct gtctctgtcc tcttgtgcaa tgcgcttccc 8040
ccgggaacaa gctggcacag gacggtgctc acagaaacat ccatccctgt ggtcattgct 8100
ggaactctgg ttgggcttct actctgaatt tttctacatt ccaattgcca gaaaaatgaa 8160
gatttctgat tgcagacagc tcagcagagt tccccagcca ttccaagact tggggcttaa 8220
aggagatttg cggggaggag ctccaccaca cccagaacct ctggagaaca gattaaggct 8280
ctgagcatcg ctgttgatca tctctgcatt ggttcacttt tctctttgtg gtgaggggtg 8340
gatatagtaa tatgcactga catgtatgat taagttctta gtctgatact agcacagtgc 8400
taaggggcta tacaccttaa ctctgacaat aagcctatga gatgggaatc atcaaattac 8460
ccctttgggt ggcttagagc agtggttatc aaagtgcctt cttggactag caacatgagc 8520
atcacttgga aatgtgttag aaatgcaaat tcccaggtgc tattgcctta gagagcataa 8580
gaatctcccc caagttgcat agcagcaagt ggcagcccag gactgcccca ggacccacac 8640
ttctgcccac tagtcactgc tgcctgtgtc tgtgggccct gtctcccttt cacaggggtg 8700
ggtgagtgat catgggctga gagaggctga aaggaataca aaagaacagc acattcacta 8760
ccatactctt tgtaattaga aaagactggg gcccggcaca gtggttcatg cctataatcc 8820
cagcactttg ggaggccaag gcaggaggat cacttgagcc caggagttca agaccaacct 8880
aagcaacata gccagaccct atctcaataa aaattaaaaa agaaaagatt ggaaacagcc 8940
taaaccagcc ctaggctggt taaataaact atggggtgtt catgtaatgc aacaactttt 9000
tacagaaaaa gagtaggaaa gctttttata gatactatga aatggtctct acaatggagt 9060
attaagtagc agaaagcaaa gtgtagaaca ctgaatatag gaaactacca tttgtataaa 9120
aaaagagaca atacgtaaac aaatttgttt atatgcaaat acacacacac actgaaagac 9180
aattcaaaga attggcacac agagacttcc tagagttgac tgtgcagagg gatgtgagga 9240
ggacctctca tatgtgcctt ggtacctttt gcatgagtta cctactcaaa tgataaatag 9300
agtacgattc aaaagaagaa gaagaaagaa gaagggagag gaggaccagc ctgagggctt 9360
aaaaatgcca gacattgggc tgaattctta catgcatcat ctcctttaat ctcctcaaca 9420
acccctagag ttgattacta ttattagtcc cattttgttg acatggaaac agaggcacag 9480
agaggctaag tgactttcct tgagtacaga gctattgagt ggaagagctg ggatttgaac 9540
caacatatgt gtgactccag agcccaagct gtaaatcact gtattacttt atatgtgtga 9600
gttaatttca tcctaccaac tctctttgaa agaagtgatg gttttcccct ttataaataa 9660
gaaaatagag gcccaaaggg gttatgtggc ttggccaagg tcacattgct gaagcatgac 9720
caaccaggaa gagaatccct agaaaggatg tacaattgct ggggtctgta gctgcaagtt 9780
ctcactagaa gagaaccctt ctcaatagga tagaggggaa aggctgttgt cctgtgtaaa 9840
ggcagggacc atcatgtcag ctgattgccc agtttctggc atagcatctg gtacatgctg 9900
agcacctgaa aactttggaa ggaagagagg gaatgaggaa aggcaatgct gaccagtggc 9960
cacccctgga aggaactctg taagtcagct aggccagatg gacaaactgc agcctagaga 10020
tggggagggg ctaacttaaa ctggtcgagt aaggaggttt gtttgttttt ttgtttgttt 10080
gtttttgttt tttgtttttt tgggacggag tctcactctg tcacccaggg tggagtgcag 10140
tggcatgatc ttggcttact gcaacctcca cctcccggat ccaagtgatt ctcatgcctc 10200
agcctcctga gtagctggga ctacaggcac gcaccaccac tcatggctcc tttttttgta 10260
ttttaagtag agatggcatt tcaccatgtt ggccaggctg gtctcgaatt cctgacctca 10320
ggtgatctgc ccatcttggc ctcccaacgt actgggatta taggcgtgag ccactgcacc 10380
aggcccagta aggaattctg aagagagtgg acacaagggc agataatatt ttttaatgac 10440
ctacttacag gctgggaacg gtggctcacg tctgtaatcc cagcactttg ggaggctgag 10500
gcgggcagat cacctgaggt cgggagtttg agaccatcct gatcaacatg gagaaacccc 10560
atctctacta aaaatacaaa attagctgtg tgtggtggca catgcctgta atcctagcta 10620
ctcgggaggc tgaggcagaa gaattgcttg aacctaggag gccgaggttg cggtgagcag 10680
agatcgcgcc attgcactcc agcctgggca acacgagcga aacttcgtct caaaaaaaaa 10740
aaatgaccta tttaccttgg gaaattttcg tgatttcctt ctgtctccct aacagagatg 10800
gaatgggaca ggaactggcc aattttgatt ggaatgagaa gaaatatcca tcccaaggtt 10860
aaattcagtg gggaggaggg tctttcagca gctgttgagg taacagggag gcagtggata 10920
taagaaggca gctgagatat aaaggagagg ccagtggatt cgaaatcagg ggatctgggt 10980
tctagtctca gctctgcttt gtactagctg ggttatgtga gcaagtcact tcccctccct 11040
gacccttact gtcttcatct ataaatagca gagttatcgt gggacacaaa taagaataca 11100
gaaagcatgc ataaagtatg ccgggccctg tggctcatgc ctgtaatctc agcactttgg 11160
gaggctaagg ctggcagatc acctaaggtc agaagttcga gaccagcctg accaacatgg 11220
caaaacccca tctctactaa aaatacaaaa attagctggg catgatggtg cgcacctgta 11280
atcccagcta ctcaggaggc tgaggcagga gaatcacttg aacctgggag gcggaggttg 11340
cagtgagatg agatcgtacc actgcactcc agcctgggca acaaagcgag actgtctcaa 11400
aaaccaaacc aaaacaaaca aaaaaagaaa gcatgcatag agcaaatgtt aatatgggga 11460
gttattaagg acacacaaca acagtactgg tgacaaactg cgctgaacga cttgcctgtc 11520
gcatcagcca ttctcttgat tccaaatgta gtgcggagct gagtccatgc cggtctcctc 11580
cacttgttga aggggaatta actgtctggg ctccctatga ggcttttgct gaccttcctt 11640
cccccagggc agcacttacc atgttccttg cttaggtgtc tgcctctctc actgacagct 11700
aattgagggc agagaccatg cagtgttcct cacttaattc ttaaaccaag gacacagtgg 11760
gagagatgga gggaaggaag gagacatgga tgcatggatg gataatggac agttgaatat 11820
tttcagcatc cagaggaaag ataattctga tgctggtaag ttaacacttc ttagagaaaa 11880
tctatttgga ctgagactta aaagagtagg taaggtttca gtagggtgag atcgagaggt 11940
tagagaggag gaaggtggtt gggtaggtga gaacagcctg agctcaggca cagggcagga 12000
aagctcaagg catcgggcag tcatgggcag tggtctgggg tcgacggatc ggaaagaggg 12060
ctgtggcccg ctgccgctgg aaaggcaggt ttgagccagg ttgtggcagg ccttgaaaat 12120
tgagcaaagt gtctggactc ctccatcctg caggcaacag ggcgccacag aaagttttgt 12180
aagagagaag tgacctgttc tgccctgtgc tcgctggcgg cgtgtggaag ggcgggcacc 12240
gggccaaggc cagctcgggg aggaggtctc accacttgct gctctctgcc gggctctcct 12300
gaagagctgc tcaggatcag ggcgagatgt gggaggctgt ggatcctcct gcagggaagg 12360
cttccccttc agaaatggct ggattggaca gcaagccttc caggcctgcc tgctgggcat 12420
agacccatga ggccagactt accctccgca ttccccagag caccctcagc agcactgccc 12480
cagttgccag gaagtgcctt agctctgggt taaagtcccg gctcttccac ggaccctggg 12540
gtttggacta gtccctgtgc ctctctcgca gcccctgtgt ttcacaactt caggaagtcc 12600
cattcacacg ggagacaatg aaacaatgtg cccagacttg tgcaacccag cggtcctgct 12660
tctaatagca atttccttgg ctgtaccgaa aggaggacga aggttggtgt ggatcacctc 12720
tgcaggccac tccaagtctc aatttatagc agtctgagca aaatgatggg ctttggtagg 12780
aggtaggggg ccagggcctt tgt 12803

<210> SEQ ID NO 9
<211> LENGTH: 15
<212> TYPE: DNA
<213> ORGANISM: Homo sapiens

<400> SEQUENCE: 9
aacacgtcta tacgc 15

<210> SEQ ID NO 10
<211> LENGTH: 15
<212> TYPE: DNA
<213> ORGANISM: Mus musculus

<400> SEQUENCE: 10
aggtgtgcga tagag 15

<210> SEQ ID NO 11
<211> LENGTH: 16
<212> TYPE: DNA
<213> ORGANISM: Mus musculus

<400> SEQUENCE: 11
cgcaagtgcc aagagt 16

<210> SEQ ID NO 12
<211> LENGTH: 16
<212> TYPE: DNA
<213> ORGANISM: Homo sapiens

```
<400> SEQUENCE: 12

caagaagctg gagttg                                                  16


<210> SEQ ID NO 13
<211> LENGTH: 20
<212> TYPE: DNA
<213> ORGANISM: Homo sapiens

<400> SEQUENCE: 13

gtcgactctg ctatactcca                                              20


<210> SEQ ID NO 14
<211> LENGTH: 15
<212> TYPE: DNA
<213> ORGANISM: Homo sapiens

<400> SEQUENCE: 14

aggtgtgcga tagag                                                   15
```